United States Patent
Fujita et al.

(10) Patent No.: US 9,144,402 B2
(45) Date of Patent: Sep. 29, 2015

(54) DEVICE FOR ESTIMATING STATE OF LIVING ORGANISM

(75) Inventors: Etsunori Fujita, Hiroshima (JP); Yumi Ogura, Hiroshima (JP); Shinichiro Maeda, Hiroshima (JP); Naoki Ochiai, Hiroshima (JP); Shigeki Wagata, Hiroshima (JP)

(73) Assignee: Delta Tooling Co., Ltd., Hiroshima-shi (JP)

( * ) Notice: Subject to any disclaimer, the term of this patent is extended or adjusted under 35 U.S.C. 154(b) by 513 days.

(21) Appl. No.: 13/579,575

(22) PCT Filed: Jan. 31, 2011

(86) PCT No.: PCT/JP2011/051876
§ 371 (c)(1),
(2), (4) Date: Oct. 12, 2012

(87) PCT Pub. No.: WO2011/102208
PCT Pub. Date: Aug. 25, 2011

(65) Prior Publication Data
US 2013/0030256 A1 Jan. 31, 2013

(30) Foreign Application Priority Data
Feb. 18, 2010 (JP) ................................ 2010-034139

(51) Int. Cl.
*A61B 5/00* (2006.01)
*A61N 1/00* (2006.01)
(Continued)

(52) U.S. Cl.
CPC .................. *A61B 5/18* (2013.01); *A61B 5/6887* (2013.01); *A61B 7/00* (2013.01); *A61B 5/1102* (2013.01); *A61B 5/113* (2013.01); *A61B 5/7239* (2013.01); *A61B 2562/0204* (2013.01)

(58) Field of Classification Search
USPC .............................................. 600/300; 607/7
See application file for complete search history.

(56) References Cited

U.S. PATENT DOCUMENTS

| 2004/0236235 A1 | 11/2004 | Fujita et al. |
| 2004/0243013 A1 | 12/2004 | Kawachi et al. |

(Continued)

FOREIGN PATENT DOCUMENTS

| JP | 7 59757 | 3/1995 |
| JP | 2004 344612 | 12/2004 |

(Continued)

OTHER PUBLICATIONS

Fujita, E., et al., "Development of the measurement method of the prediction of sleep by finger plethyamogram data," Ergonomics, vol. 41, No. 4, Total 10 pages, (2005) (with English abstract).
(Continued)

*Primary Examiner* — Nicole F Lavert
(74) *Attorney, Agent, or Firm* — Oblon, McClelland, Maier & Neustadt, L.L.P.

(57) ABSTRACT

A technology to grasp a state of a human being more accurately is provided. The technology is provided with means for acquiring a time-series waveform of a frequency from a time-series waveform of a biological signal sampled from the upper body of a human being and for further acquiring a time-series waveform of frequency slope and a time-series waveform of frequency fluctuation and for applying frequency analysis to them. In the frequency analysis, a power spectrum of each frequency corresponding to a functional adjustment signal, a fatigue reception signal, and an activity adjustment signal, respectively, determined in advance is acquired. Then, a state of a human being is determined from a time-series change of each power spectrum. The fatigue reception signal indicates a degree of progress of fatigue in a usual active state and thus, by comparing it with degrees of predominance of the functional adjustment signal and the activity adjustment signal as their distribution rates, a state of a human being (relaxed state, fatigued state, state in which sympathetic nerve is predominant, a state in which parasympathetic nerve is predominant and the like) can be determined more accurately.

19 Claims, 70 Drawing Sheets

(51) Int. Cl.
*A61B 5/18* (2006.01)
*A61B 7/00* (2006.01)
*A61B 5/11* (2006.01)
*A61B 5/113* (2006.01)

(56) References Cited

U.S. PATENT DOCUMENTS

2004/0260440 A1 12/2004 Fujita et al.
2007/0299636 A1 12/2007 Fujita et al.
2008/0109041 A1* 5/2008 de Voir .............................. 607/7

FOREIGN PATENT DOCUMENTS

| | | |
|---|---|---|
| JP | 2004 344613 | 12/2004 |
| JP | 2004 350773 | 12/2004 |
| JP | 2005 092193 | 10/2005 |
| JP | 2006 149469 | 6/2006 |
| JP | 2006 149470 | 6/2006 |
| JP | 2007 6970 | 1/2007 |
| JP | 2007 90032 | 4/2007 |
| JP | 2011 046178 | 4/2011 |

OTHER PUBLICATIONS

Ochiai, N., et al., "The Application to Fatigue and Sleep Prediction, of the Signal of Biological Fluctuation Measured from Noninvasive Sensor," 39th Japan Ergonomics Society Chugoku and Shikoku Branch Convention, Total 2 pages, (Nov. 25, 2006).

Maeda, S., et al., "Trial Manufacture of Car Seat having a Non-Aggression Biological Signal Sensing Function," 39th Ergonomics Society Chugoku and Shikoku Branch Convention, Total 2 pages, (Nov. 25, 2006).

International Search Report Issued Apr. 25, 2011 in PCT/JP11/51876 Filed Jan. 31, 2011.

* cited by examiner (A)

(B)

(A)

(B)

(A)

(B)

DEVICE FOR ESTIMATING STATE OF LIVING ORGANISM

TECHNICAL FIELD

The present invention relates to a technique for estimating a state of a biological body using a time-series waveform of a biological signal obtained from an upper body of a person.

BACKGROUND ART

Monitoring a biological body state of a driver during driving has attracted attention as a preventive measure against an accident or the like in recent years. The present applicant disclosed techniques of disposing a pressure sensor in a seat cushion section, obtaining and analyzing breech pulse waves, and determining a sleep prediction phenomenon in Patent Literatures 1 to 3.

Specifically, a maximum value and a minimum value of a time-series waveform of a pulse wave are obtained by a smoothing differentiation method of Savitzky and Golay, respectively. The maximum value and the minimum value are obtained for each 5 seconds so that their mean values are obtained. Using a square of a difference between the respective mean values of the maximum values and the minimum values obtained as a power value, the power value is plotted for each 5 seconds so that a time-series waveform of the power value is produced. In order to read a global change of the power value from this time-series waveform, a slope of the power value regarding a certain time window Tw (180 seconds) is obtained by least-square method. Next, the slope regarding the next time window Tw is similarly calculated in an overlapped time TI (162 seconds) and the calculation results are plotted. A time-series waveform of the slope of the power value is obtained by repeating this calculation (movement calculation) sequentially. On the other hand, the maximum Lyapunov exponent is obtained by applying Chaos analysis to the time-series waveform of the pulse wave, a maximum value is obtained by a smoothing differentiation like the above, and a time-series waveform of a slope of the maximum Lyapunov exponent is obtained by conducting movement calculation.

Then, the time-series waveform of the slope of the power value and the time-series waveform of the slope of the maximum Lyapunov exponent take phases opposite to each other, and a waveform having a large amplitude at a low frequency in the time-series waveform of the slope of the power value is determined as a characteristic signal indicating a sleep prediction and a point at which the amplitude has become small thereafter is determined as a sleep-onset point.

Further, as Patent Literature 4, a system provided with an airbag (air pack) including a three-dimensional solid fabric inserted therein, where the air pack is disposed at a site corresponding to a waist portion of a person, an air pressure fluctuation in the air pack is measured, a biological signal of the person is detected from the time-series waveform of the air pressure fluctuation obtained, and the biological body state of the person is analyzed is disclosed. Further, in Non-Patent Literatures 1 and 2, trials for detecting a biological signal of a person by disposing an air pack sensor along a lumber iliocostal muscle are reported. This air pressure fluctuation of the air pack is caused by fluctuation in a downward aorta with movement of a heart, and a state change closer to the movement of the heart than use of the breech pulse waves in Patent Literatures 1 and 2 can be captured.

PRIOR ART LITERATURES

Patent Literature

Patent Literature 1: Japanese Patent Application Laid-Open No. 2004-344612
Patent Literature 2: Japanese Patent Application Laid-Open No. 2004-344613
Patent Literature 3: WO2005/092193A1
Patent Literature 4: Japanese Patent Application Laid-Open No. 2007-90032

Non-Patent Literatures

Non-Patent Literature 1: "ORIGINAL: DEVELOPMENT OF THE MEASUREMENT METHOD OF THE PREDICTION OF SLEEP BY FINGER PLETHYSMOGRAM DATA" by Etsunori FUJITA (and eight others), Ergonomics, Vol 41, No. 4 ('05)
Non-Patent Literature 2: "APPLICATION OF BIOLOGICAL WANDERING SIGNAL MEASURED BY NON-INVASIVE TYPE SENSOR TO FATIGUE AND SLEEP PREDICTION" by Naoki OCHIAI (and six others), 39th Japan Ergonomics Society Chugoku and Shikoku Branch convention, Collection of Literatures and Papers issued on Nov. 25, 2006 from Japan Ergonomics Society Chugoku and Shikoku Branch Secretariat
Non-Patent Literature 3: "TRIAL PRODUCTION OF VEHICLE SEAT HAVING NON-INVASIVE BIOLOGICAL SIGNAL SENSING FUNCTION" by Shinichiro MAEDA (and four others), 39th Japan Ergonomics Society Chugoku and Shikoku Branch Convention, Collection of Literatures and Papers issued on Nov. 25, 2006 from Japan Ergonomics Society Chugoku and Shikoku Branch Secretariat

SUMMARY OF INVENTION

Technical Problem

As described above, in the techniques described in Patent Literatures 1 to 4 and Non-Patent Literatures 1 to 3, the time where the time-series waveform of the slope of the power value and the time-series waveform of the slope of the maximum Lyapunov exponent has taken phases opposite to each other and a waveform having a large amplitude at a low frequency has occurred in the time-series waveform of the slope of the power value is regarded as the sleep prediction phenomenon.

Moreover, the applicant proposed the following technique as Japanese Patent Application Laid-Open No. 2009-237802. That is, it is a technique in which a time-series waveform of a frequency is acquired from the time-series waveform of a biological signal obtained by biological signal measuring means, and a frequency slope time-series waveform and a frequency fluctuation time-series waveform acquired from this time-series waveform of the frequency are used so as to determine a state of a human being by combining signs of the frequency slope time-series waveform, the signs of an integral waveform of the frequency slope time-series waveform, emergence of an opposite phase (the emergence of the opposite phase indicates a sleep prediction) when the frequency slope time-series waveform and the frequency fluctuation time-series waveform are outputted in superposition and the like.

The applicant proposes techniques for grasping a state of a human being using a biological signal as above, but a proposal of a technique for grasping a state of a human being more accurately is constantly in demand. Moreover, if there is plurality of methods for grasping a state of a human being, the state of a human being can be grasped more accurately by using these methods at the same time. The present invention was made in view of the above.

Solution to Problem

Here, as illustrated in the above-described Non-Patent Literature 1, it was confirmed by an analysis of a slope time-series waveform of a digital volume pulse that a frequency at which a characteristic of fluctuation is switched as a result of atrial fibrillation is 0.0033 Hz. Moreover, application of slide calculation for 180 seconds when the slope time-series waveform is acquired became a filter having a component of 0.0055 Hz as a central frequency, covering a high-frequency component (HF) to an ultra low frequency component (ULF) less than 0.0033 Hz, and it was confirmed that an amplitude spectrum indicating a sleep prediction phenomenon emerges in this ULF. A swinging waveform emerges during activity in the vicinity of 0.0055 Hz, and the swinging waveform emerges in the vicinity of 0.0033 Hz in a relaxed and rest state.

Thus, from these findings, the inventor set a signal in the vicinity of 0.0033 Hz (in a range from 0.002 to 0.0052 Hz) (hereinafter referred to as a "fatigue reception signal") as a basis and used it as a signal indicating a degree of progress of fatigue in a usual active state, used a signal in the vicinity of 0.0055 Hz (in a range of 0.004 to 0.007 Hz) (hereinafter referred to as an "activity adjustment signal") as a signal at which a degree of influence by control of brain and an autonomic nerve system emerges during activity and used a signal in the vicinity of a frequency corresponding to approximately ½ of 0.0033 Hz (0.0027 Hz or less) as a representative signal component of an ULF area indicating a rapid nonlinear characteristic (hereinafter referred to as a "functional adjustment signal") as a signal at which a degree of practice of functional adjustment indicating a transition state between each state of activity—rest—sleep (sleep prediction, for example) emerges, paid attention to determination of a state of a human being from a time-series change of a power spectrum of these signals and completed the present invention.

Moreover, as a biological signal, the applicant paid attention not to a digital volume pulse but to grasping of a degree of fluctuation of atrium and aorta. That is because a wall of an aorta is rich in elasticity among arteries and can receive a high pressure of blood directly pumped out of a heart and also, there is an aortic valve as a valve for preventing backflow immediately out of the left ventricle of the heart. Thus, by analyzing a biological signal grasping a degree of fluctuation of the atrium and aorta, an adjustment ring of a negative feedback mechanism of the brain and the autonomic nerve system for homeostasis of a biological body can be well grasped, whereby not only the activity of the autonomic nerve but also an activation state of a brain function can be grasped, and a biological state can be estimated more accurately.

That is, the biological body state estimation device of the present invention is a biological body state estimation device for estimating a state of a human being by using a biological signal sampled from the upper body of a human being by biological signal measuring means and is characterized by having:

first frequency calculating means for acquiring a zero-crossing point at which a time-series waveform of a biological signal obtained by the biological signal measuring means is changed from positive to negative and for acquiring the time-series waveform of the frequency of the biological signal by using this zero-crossing point;

first frequency slope time-series analysis calculating means for performing movement calculation for acquiring a slope of the frequency at each predetermined time window set with a predetermined overlap time in the time-series waveform of the frequency of the biological signal obtained by the first frequency calculating means and for outputting a time-series change of the slope of the frequency obtained at each time window as a frequency slope time-series waveform;

power spectrum calculating means for applying frequency analysis to the frequency slope time-series waveform obtained by the first frequency slope time-series analysis calculating means and acquiring a power spectrum of each frequency corresponding to a functional adjustment signal, a fatigue reception signal, and an activity adjustment signal determined in advance; and determining means for determining a state of a human being from a time-series change of the power spectrum of each frequency corresponding to the functional adjustment signal, the fatigue reception signal, and the activity adjustment signal acquired by the power spectrum calculating means.

Moreover, it is preferable that first frequency fluctuation time-series analysis calculating means for performing the movement calculation for acquiring a mean value of the frequency at each predetermined time window set with the predetermined overlap time in the time-series waveform of the frequency of the biological signal obtained by the first frequency calculating means and acquiring a time-series waveform of the mean value of the frequency obtained at each time window as a frequency fluctuation time-series waveform is provided; and the power spectrum calculating means further has means for applying frequency analysis to the frequency fluctuation time-series waveform obtained by the first frequency fluctuation time-series analysis calculating means and acquiring a power spectrum of each frequency corresponding to the functional adjustment signal, the fatigue reception signal, and the activity adjustment signal determined in advance.

Moreover, it is preferable that second frequency calculating means for acquiring a maximum value by applying smoothing differentiation to an original waveform of the biological signal obtained by the biological signal measuring means and acquiring the time-series waveform of the frequency of the biological signal by using this maximum value; and second frequency slope time-series analysis calculating means for performing the movement calculation for acquiring a slope of the frequency at each predetermined time window set with the predetermined overlap time in the time-series waveform of the frequency of the biological signal obtained by the second frequency calculating means and outputting a time-series change of the slope of the frequency obtained at each time window as a frequency slope time-series waveform are provided; and the power spectrum calculating means further has means for applying frequency analysis to the frequency slope time-series waveform obtained by the second frequency slope time-series analysis calculating means and acquiring a power spectrum of each frequency corresponding to the functional adjustment signal, the fatigue reception signal, and the activity adjustment signal determined in advance.

Moreover, it is preferable that second frequency fluctuation time-series analysis calculating means for performing the movement calculation to acquire a mean value of the frequency at each predetermined time window set with the predetermined overlap time in the time-series waveform of the frequency of the biological signal obtained by the second frequency calculating means and acquiring a time-series waveform of a mean value of the frequency obtained at each time window as a frequency fluctuation time-series waveform is provided; and the power spectrum calculating means further has means for applying frequency analysis to the frequency fluctuation time-series waveform obtained by the second frequency fluctuation time-series analysis calculating means and acquiring a power spectrum of each frequency corresponding to the functional adjustment signal, the fatigue reception signal, and the activity adjustment signal determined in advance.

The determining means is preferably means for determining a state of a human being by acquiring a time-series change in the power spectrum of each frequency corresponding to the functional adjustment signal, the fatigue reception signal, and the activity adjustment signal acquired from the frequency slope time-series waveform obtained by the first frequency slope time-series analysis calculating means and acquiring a degree of relative predominance of each signal as a distribution rate.

The determining means determines the state of a human being by acquiring the time-series change of the power spectrum of each frequency corresponding to the functional adjustment signal, the fatigue reception signal, and the activity adjustment signal acquired from the frequency slope time-series waveform obtained by the first frequency slope time-series analysis calculating means and by acquiring a degree of relative predominance of each signal as a distribution rate and moreover, preferably determines the state of a human being by adding a time-series change of the distribution rate of the power spectrum of each frequency corresponding to the functional adjustment signal, the fatigue reception signal, and the activity adjustment signal acquired from at least one of the frequency fluctuation time-series waveform obtained by the first frequency fluctuation time-series analysis calculating means, the frequency slope time-series waveform obtained by the second frequency slope time-series analysis calculating means, and the frequency fluctuation time-series waveform obtained by the second frequency fluctuation time-series analysis calculating means.

The determining means preferably has means for determining that a time zone in which the power spectrum of the fatigue reception signal acquired from the frequency slope time-series waveform obtained by the first frequency slope time-series analysis calculating means indicates a time-series change having a lowering tendency is an emergence period of a state change of a human being.

The determining means preferably has means for determining a sleep-related phenomenon emergence period if the power spectrum of the functional adjustment signal acquired from the frequency slope time-series waveform obtained by the first frequency slope time-series analysis calculating means indicates a time-series change having a rising tendency in a time zone when the power spectrum of the fatigue reception signal acquired from the frequency slope time-series waveform obtained by the first frequency slope time-series analysis calculating means indicates a time-series change having a lowering tendency.

It is preferable that the determining means further has means for determining the sleep-related phenomenon emergence period if the functional adjustment signal acquired from at least one of the frequency fluctuation time-series waveform obtained by the first frequency fluctuation time-series analysis calculating means, the frequency slope time-series waveform obtained by the second frequency slope time-series analysis calculating means, and the frequency fluctuation time-series waveform obtained by the second frequency fluctuation time-series analysis calculating means indicates a time-series change with a rising tendency.

It is preferable that the functional adjustment signal used by the power spectrum calculating means has a frequency of 0.0027 Hz or less, the fatigue reception signal has a frequency within a range from 0.002 to 0.0052 Hz, and the activity adjustment signal has a frequency within a range from 0.004 to 0.007 Hz.

Moreover, a computer program of the present invention is a computer program incorporated in a biological body state estimation device for estimating a state of a human being by using a biological signal sampled from the upper body of a human being by the biological signal measuring means, characterized by having:

a first frequency calculating step of acquiring a zero-crossing point at which a time-series waveform of a biological signal obtained by the biological signal measuring means is changed from positive to negative and of acquiring the time-series waveform of the frequency of the biological signal by using this zero-crossing point;

first frequency slope time-series analysis calculating step of performing movement calculation for acquiring a slope of the frequency at each predetermined time window set with a predetermined overlap time in the time-series waveform of the frequency of the biological signal obtained by the first frequency calculating means and of outputting a time-series change of the slope of the frequency obtained at each time window as a frequency slope time-series waveform;

power spectrum calculating step of applying frequency analysis to the frequency slope time-series waveform obtained by the first frequency slope time-series analysis calculating step and acquiring a power spectrum of each frequency corresponding to a functional adjustment signal, a fatigue reception signal, and an activity adjustment signal determined in advance; and determining step of determining a state of a human being from a time-series change of the power spectrum of each frequency corresponding to the functional adjustment signal, the fatigue reception signal, and the activity adjustment signal acquired by the power spectrum calculating step.

Moreover, it is preferable that a first frequency fluctuation time-series analysis calculating step of performing the movement calculation for acquiring a mean value of the frequency at each predetermined time window set with the predetermined overlap time in the time-series waveform of the frequency of the biological signal obtained by the first frequency calculating step and acquiring a time-series waveform of the mean value of the frequency obtained at each time window as a frequency fluctuation time-series waveform is provided; and the power spectrum calculating step further has a step of applying frequency analysis to the frequency fluctuation time-series waveform obtained by the first frequency fluctuation time-series analysis calculating step and acquiring a power spectrum of each frequency corresponding to the functional adjustment signal, the fatigue reception signal, and the activity adjustment signal determined in advance.

Moreover, it is preferable that a second frequency calculating step of acquiring a maximum value by applying smoothing differentiation to an original waveform of the biological signal obtained by the biological signal measuring means and acquiring the time-series waveform of the frequency of the biological signal by using this maximum value; and a second frequency slope time-series analysis calculating step of performing the movement calculation for acquiring a slope of the frequency at each predetermined time window set with the predetermined overlap time in the time-series waveform of the frequency of the biological signal obtained by the second frequency calculating step and outputting a time-series change of the slope of the frequency obtained at each time window as a frequency slope time-series waveform are provided; and the power spectrum calculating step further has a step of applying frequency analysis to the frequency slope time-series waveform obtained by the second frequency slope time-series analysis calculating step and of acquiring a power spectrum of each frequency corresponding to the functional adjustment signal, the fatigue reception signal, and the activity adjustment signal determined in advance.

Moreover, it is preferable that a second frequency fluctuation time-series analysis calculating step of performing the movement calculation to acquire a mean value of the frequency at each predetermined time window set with the predetermined overlap time in the time-series waveform of the frequency of the biological signal obtained by the second frequency calculating step and acquiring a time-series waveform of a mean value of the frequency obtained at each time window as a frequency fluctuation time-series waveform is provided; and the power spectrum calculating step further has a step of applying frequency analysis to the frequency fluctuation time-series waveform obtained by the second frequency fluctuation time-series analysis calculating step and acquiring a power spectrum of each frequency corresponding to the functional adjustment signal, the fatigue reception signal, and the activity adjustment signal determined in advance.

The determining step is preferably a step for determining a state of a human being by acquiring a time-series change in the power spectrum of each frequency corresponding to the functional adjustment signal, the fatigue reception signal, and the activity adjustment signal acquired from the frequency slope time-series waveform obtained by the first frequency slope time-series analysis calculating step and by acquiring a degree of relative predominance of each signal as a distribution rate.

The determining step determines the state of a human being by acquiring the time-series change of the power spectrum of each frequency corresponding to the functional adjustment signal, the fatigue reception signal, and the activity adjustment signal acquired from the frequency slope time-series waveform obtained by the first frequency slope time-series analysis calculating step and by acquiring a degree of relative predominance of each signal as a distribution rate and moreover, preferably determines the state of a human being by adding a time-series change of the distribution rate of the power spectrum of each frequency corresponding to the functional adjustment signal, the fatigue reception signal, and the activity adjustment signal acquired from at least one of the frequency fluctuation time-series waveform obtained by the first frequency fluctuation time-series analysis calculating step, the frequency slope time-series waveform obtained by the second frequency slope time-series analysis calculating step, and the frequency fluctuation time-series waveform obtained by the second frequency fluctuation time-series analysis calculating step.

The determining step preferably has a step of determining that a time zone in which the power spectrum of the fatigue reception signal acquired from the frequency slope time-series waveform obtained by the first frequency slope time-series analysis calculating step indicates a time-series change having a lowering tendency is an emergence period of a state change of a human being.

The determining step preferably has a step of determining a sleep-related phenomenon emergence period if the power spectrum of the functional adjustment signal acquired from the frequency slope time-series waveform obtained by the first frequency slope time-series analysis calculating step indicates a time-series change having a rising tendency in a time zone when the power spectrum of the fatigue reception signal acquired from the frequency slope time-series waveform obtained by the first frequency slope time-series analysis calculating step indicates a time-series change having a lowering tendency.

It is preferable that the determining step further has a step of determining the sleep-related phenomenon emergence period if the functional adjustment signal acquired from at least one of the frequency fluctuation time-series waveform obtained by the first frequency fluctuation time-series analysis calculating step, the frequency slope time-series waveform obtained by the second frequency slope time-series analysis calculating step, and the frequency fluctuation time-series waveform obtained by the second frequency fluctuation time-series analysis calculating step indicates a time-series change with a rising tendency.

It is preferable that the functional adjustment signal used by the power spectrum calculating step has a frequency of 0.0027 Hz or less, the fatigue reception signal has a frequency within a range from 0.002 to 0.0052 Hz, and the activity adjustment signal has a frequency within a range from 0.004 to 0.007 Hz.

Advantageous Effects of Invention

The present invention has means for acquiring a time-series waveform of a frequency from a time-series waveform of a biological signal sampled from the upper body of a human being and moreover, for acquiring a time-series waveform of a frequency slope and a time-series waveform of frequency fluctuation and applying frequency analysis thereto. At the frequency analysis, a power spectrum of each frequency corresponding to a functional adjustment signal, a fatigue reception signal, and an activity adjustment signal determined in advance is acquired. Then, a state of a human being is determined from the time-series change of each power spectrum. Since the fatigue reception signal indicates a degree of progress of fatigue in a usual active state, by also comparing it with degrees of predominance of the functional adjustment signal and the activity adjustment signal as their distribution rates, a state of a human being (a relaxed state, a fatigued state, a state of predominance of sympathetic nerves, a state of predominance of parasympathetic nerves and the like) can be determined more accurately.

BRIEF DESCRIPTION OF THE DRAWINGS

FIG. 68 illustrate basic patterns of the frequency analysis results when sleepiness emerges, in which FIG. 68(A) is a diagram illustrating the frequency analysis result of the frequency slope time-series waveform by means of the zero-crossing method, FIG. 68(B) is a diagram illustrating the frequency analysis result of the frequency fluctuation time-series waveform by means of the zero-crossing method, FIG. 68(C) is a diagram illustrating the frequency analysis result of the frequency slope time-series waveform by means of the peak detection method, and FIG. 68(D) is a diagram illustrating the frequency analysis result of the frequency fluctuation time-series waveform by means of the peak detection method, respectively.

FIG. 69 illustrate patterns of the frequency analysis results when resisting sleepiness if a state progresses from the sleepiness emergence to sleep prediction phenomenon emergence, in which FIG. 69(A) is a diagram illustrating the frequency analysis result of the frequency slope time-series waveform by means of the zero-crossing method, FIG. 69(B) is a diagram illustrating the frequency analysis result of the frequency fluctuation time-series waveform by means of the zero-crossing method, FIG. 69(C) is a diagram illustrating the frequency analysis result of the frequency slope time-series waveform by means of the peak detection method, and FIG. 69(D) is a diagram illustrating the frequency analysis result of the frequency fluctuation time-series waveform by means of the peak detection method, respectively.

FIG. 70 illustrate patterns of the frequency analysis results when accepting sleepiness if a state progresses from the sleepiness emergence to sleep prediction phenomenon emergence, in which FIG. 70(A) is a diagram illustrating the frequency analysis result of the frequency slope time-series waveform by means of the zero-crossing method, FIG. 70(B) is a diagram illustrating the frequency analysis result of the frequency fluctuation time-series waveform by means of the zero-crossing method, FIG. 70(C) is a diagram illustrating the frequency analysis result of the frequency slope time-series waveform by means of the peak detection method, and FIG. 70(D) is a diagram illustrating the frequency analysis result of the frequency fluctuation time-series waveform by means of the peak detection method, respectively.

DESCRIPTION OF EMBODIMENTS

Figure 1:
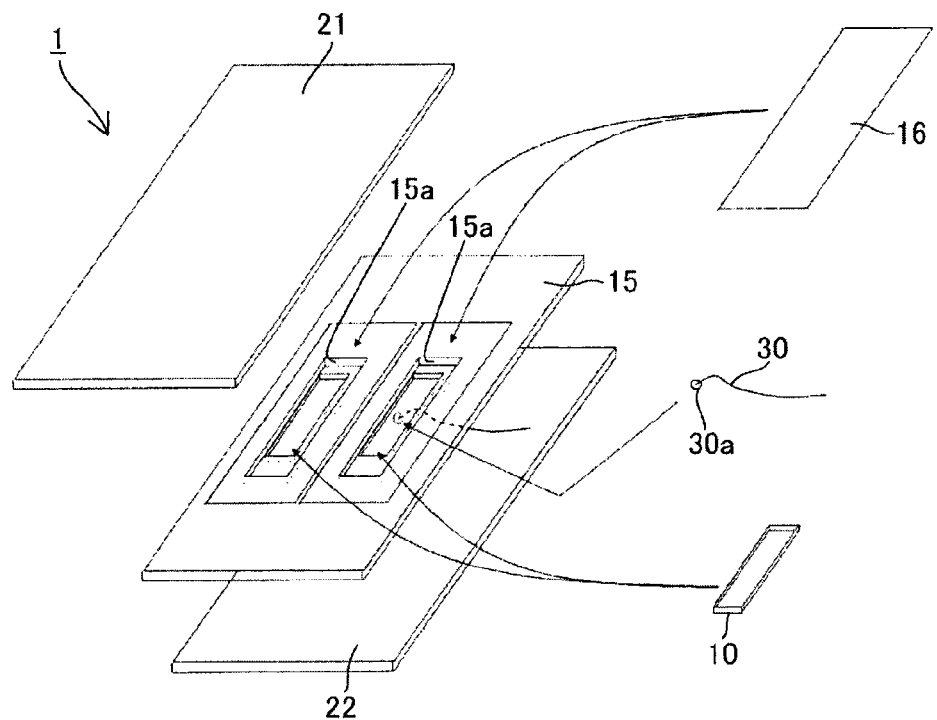
FIG. 1 is a diagram illustrating biological signal measuring means used in an embodiment of the present invention.
Figure 2:
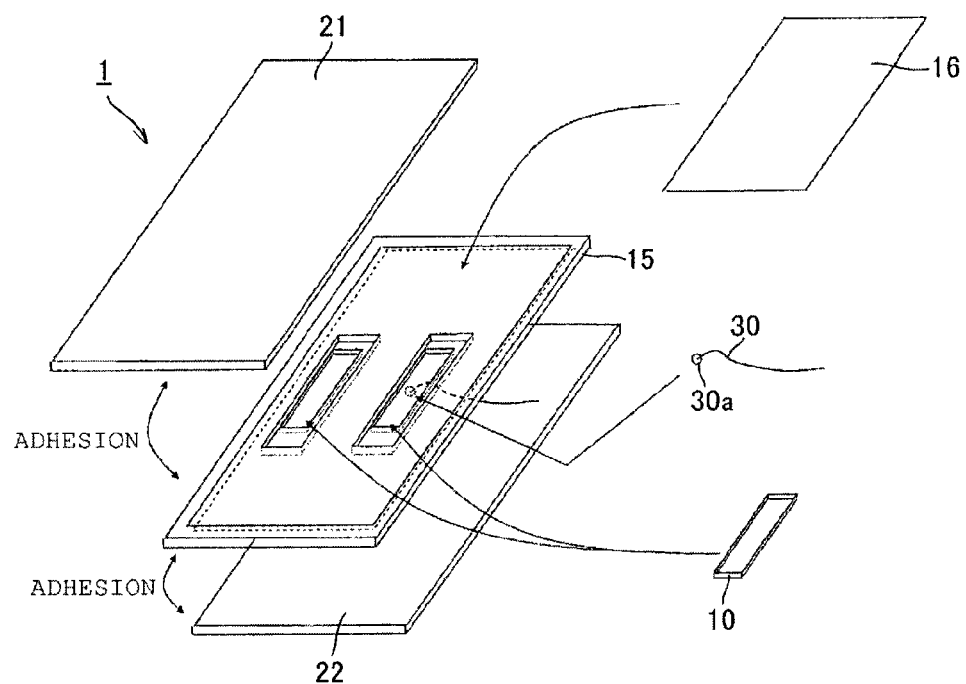
FIG. 2 is a diagram illustrating another form of the biological signal measuring means according to the above-described embodiment.
Figure 3:
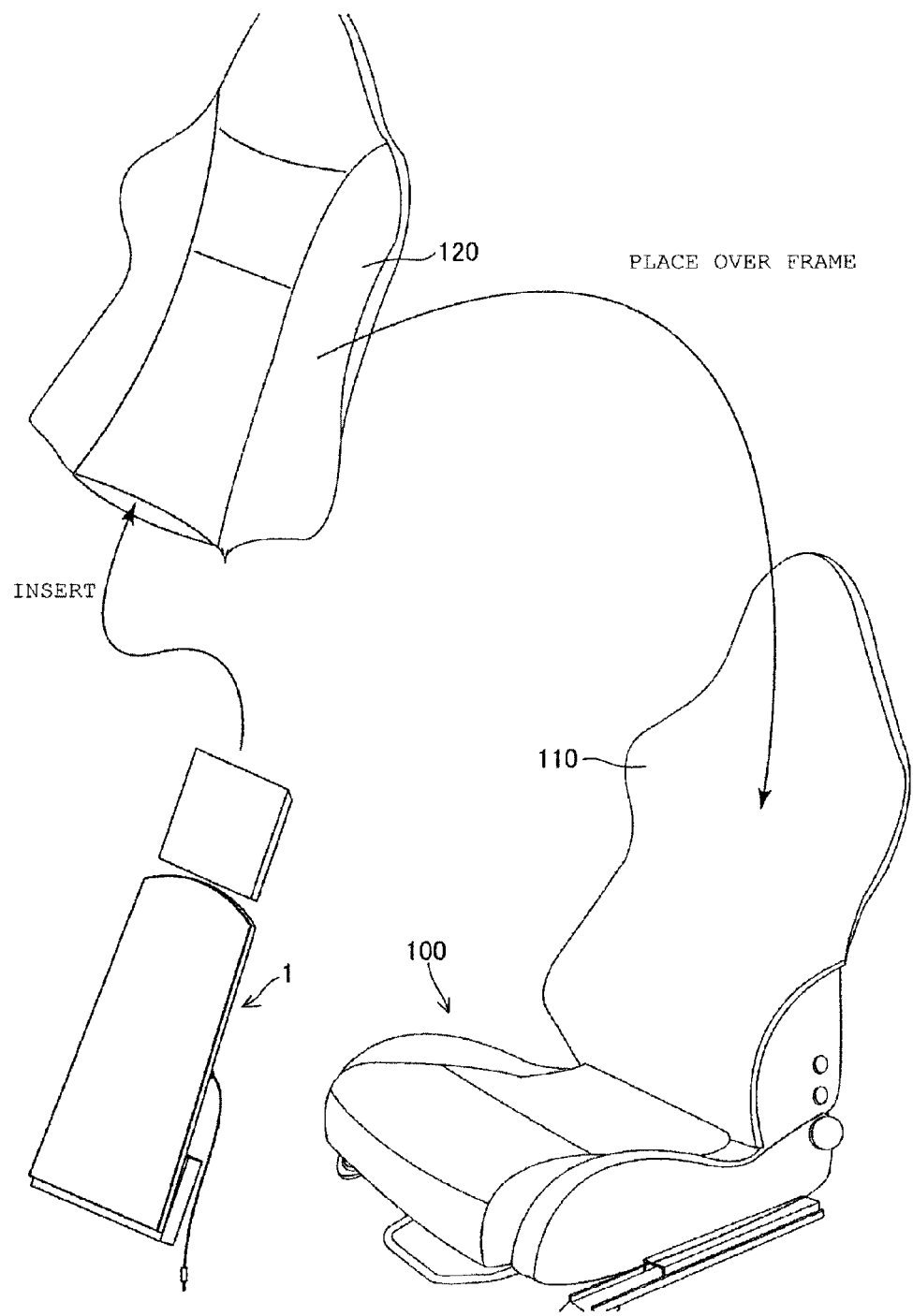
FIG. 3 is a diagram illustrating a process of incorporating the above-described biological signal measuring means in a seat.

The present invention will be described below in further detail on the basis of an embodiment of the present invention illustrated in the drawings. FIGS. 1 and 2 are diagrams illustrating biological signal measuring means 1 which samples a biological signal or fluctuation of an aorta on a waist portion involved with motion of an atrium to be analyzed by a biological body state estimation device 60 according to this embodiment, and FIG. 3 is a diagram illustrating a process of incorporating the biological signal measuring means 1 in a seat 100 for a vehicle. First, this biological signal measuring means 1 will be described. The biological signal measuring means 1 includes a three-dimensional knitted material 10, a three-dimensional knitted material supporting member 15, a film 16, a plate-shaped foam bodies 21 and 22, and a vibration sensor 30.

The three-dimensional knitted material 10 is, as disclosed in Japanese Unexamined Patent Application Publication No. 2002-331603, for example, a knitted fabric having a three-dimensional structure having a pair of ground knitted fabrics arranged separately from each other and a large number of connecting fibers reciprocating between the pair of ground knitted fabrics and connecting the both.

One of the ground knitted fabrics is formed of a flat knitted fabric composition (fine stitch) which is continuous both in a wale direction and a coarse direction from a yarn obtained by twisting a monofilament, for example, while the other ground knitted fabric is formed having a knitted structure having a honeycomb-shaped (hexagonal) mesh from a yarn obtained by twisting a short fiber, for example. It is needless to say that the knitted fabric composition is optional and its combination is also optional such that a knitted fabric composition other than the fine-stitch composition or the honeycomb-shape can be employed, alternatively, the fine-stitch composition can be employed for the both. The connecting fiber is knitted between the two ground knitted fabrics so that the one ground knitted fabric and the other ground knitted fabric maintain a predetermined interval. In this embodiment, since the solid vibration of the three-dimensional knitted material or particularly the string vibration of the connecting fiber is to be detected, the connecting fiber is preferably formed of a monofilament, but the connecting fiber may also be formed of a multifilament in order to adjust a resonance frequency in accordance with the type of a biological signal to be sampled.

Moreover, the three-dimensional knitted material 10 is preferably provided with a load-deflection characteristic in a thickness direction within a range up to the load of 100 N when being placed on a measuring plate and pressurized by a pressure plate having a diameter of 30 mm or a diameter of 98 mm and with a spring constant close to the load-deflection characteristic of a muscle in the buttocks of a human being. Specifically, it is preferable to use the material having the spring constant within a range of 0.1 to 5 N/mm when being pressurized by a pressure plate having the diameter of 30 mm or the material having the spring constant within a range of 1 to 10 N/mm when being pressurized by a pressure plate having the diameter of 98 mm. By means of approximation to the load-deflection characteristic of the muscle in the buttocks of a human being, the three-dimensional knitted material is balanced with the muscle, and when a biological signal of heart rate, respiration, atrial and aortic oscillations and the like is propagated, the three-dimensional knitted material generates the vibration similar to that in the human muscle, and the biological signal can be propagated without large attenuation.

As such three-dimensional knitted material, the following may be used, for example. Each of the three-dimensional knitted materials can be used by being stacked in plural as necessary.

(1) Product Number: 49076D (by Suminoe Textile Co., Ltd.) Material:
Ground knitted fabric on the front side: Twisted yarn of polyethylene terephthalate fiber false twisted yarn of 300 decitex/288f and polyethylene terephthalate fiber false twisted yarn of 700 decitex/192f Ground knitted fabric on the back side: Combination of polyethylene terephthalate fiber false twisted yarn of 450 decitex/108f and polytrimethylene terephthalate monofilament of 350 decitex/1f Connecting fiber: polytrimethylene terephthalate monofilament of 350 decitex/1f (2) Product Number: 49011D (by Suminoe Textile Co., Ltd.) Material:
Ground knitted fabric (warp): Polyethylene terephthalate fiber false twisted yarn of 600 decitex/192f
Ground knitted fabric (weft): Polyethylene terephthalate fiber false twisted yarn of 300 decitex/72f
Connecting fiber: polyethylene terephthalate monofilament of 800 decitex/1f (3) Product Number: 49013D (by Suminoe Textile Co., Ltd.) Material:
Ground knitted fabric on the front side: Two twisted yarns of polyethylene terephthalate fiber false twisted yarn of 450 decitex/108f Ground knitted fabric on the back side: Two twisted yarns of polyethylene terephthalate fiber false twisted yarn of 450 decitex/108f
Connecting fiber: polytrimethylene terephthalate monofilament of 350 decitex/1f (4) Product Number: 69030D (by Suminoe Textile Co., Ltd.) Material:
Ground knitted fabric on the front side: Two twisted yarns of polyethylene terephthalate fiber false twisted yarn of 450 decitex/144f Ground knitted fabric on the back side: Combination of polyethylene terephthalate fiber false twisted yarn of 450 decitex/144f and polytrimethylene terephthalate monofilament of 350 decitex/1f
Connecting fiber: polytrimethylene terephthalate monofilament of 350 decitex/1f (5) Product number: T24053AY5-1S by Asahi Kasei Fibers Corporation The plate-shaped foam bodies 21 and 22 are preferably formed of bead foam bodies. As the bead foam body, a foam molded body molded by a bead method of a resin containing at least any one of polystyrene, polypropylene, and polyethylene can be used. The plate-shaped foam bodies 21 and 22 made of bead foam bodies propagate a biological signal with micro amplitude as membrane vibration by means of characteristics of a spherical resin film formed by foams constituting individual fine beads. This membrane vibration is transmitted as string vibration to the three-dimensional knitted material, the membrane vibration and the string vibration are superposed with each other, and the biological signal is detected by the vibration sensor 30 which will be described later as mechanical vibration amplified by superposition of the membrane vibration and the string vibration. Therefore, detection of the biological signal is facilitated.

If the plate-shaped foam bodies 21 and 22 are to be formed of bead foam bodies, a foaming factor is preferably within 25 to 50 times and the thickness is formed at an average diameter of a bead or less. For example, if the average diameter of a bead of 30-times foaming is approximately 4 to 6 mm, the plate-shaped foam bodies 21 and 22 are sliced to the thickness of approximately 3 to 5 mm. As a result, flexible elasticity is given to the plate-shaped foam bodies 21 and 22, and solid vibration resonant with vibration with small amplitude can easily occur. The plate-shaped foam bodies 21 and 22 may be arranged on the both sides sandwiching the three-dimensional knitted materials 10 between them as in this embodiment but may be configured to be arranged only on either one of the sides, preferably only on the seatback side.

Here, as the three-dimensional knitted material 10, a strip-shaped material having a width within a range of 40 to 100 mm and a length within a range of 100 to 300 mm is used. With the material having this size, preliminary compression (state in which a tension is generated in the connecting fiber) can easily occur in the three-dimensional knitted material 10, thus an equilibrium state can be easily created between a human being and the three-dimensional knitted material 10. In this embodiment, in order to reduce a sense of discomfort when the back part of a human being is in contact with the device, two strips are disposed on a target, sandwiching a portion corresponding to the spine. It is preferable that the three-dimensional knitted material 10 is configured to be supported by the three-dimensional knitted material supporting member 15 as illustrated in FIG. 1 so that the three-dimensional knitted materials 10 can be arranged at predetermined positions easily. The three-dimensional knitted material supporting member 15 is molded having a plate shape, and two vertically long through holes 15*a* and 15*a* for arrangement are formed at symmetrical positions sandwiching the portion corresponding to the spine. The three-dimensional knitted material supporting member 15 is preferably composed of the bead foam bodies formed having a plate shape similarly to the above-described plate-shaped foam bodies 21 and 22. The preferable foaming factor and range of thickness if the three-dimensional knitted material supporting member 15 is formed of a bead foam body are the same as those of the above-described plate-shaped foam bodies 21 and 22. However, the thicknesses of the plate-shaped foam bodies 21 and 22 stacked above and below the three-dimensional knitted materials 10 and 10 are preferably smaller than the thickness of the three-dimensional knitted material supporting member 15 in order that the membrane vibration is generated more remarkably by the biological signal.

In a state where the two three-dimensional knitted materials 10 and 10 are inserted and arranged in the through holes 15*a* and 15*a* for arrangement formed in the three-dimensional knitted material supporting member 15, the films 16 and 16 are laminated on the front side and the back side of the three-dimensional knitted materials 10 and 10. In this embodiment, the peripheral edge portions of the films 16 and 16 are bonded and laminated on the peripheral edge portions of the through holes 15*a* and 15*a* for arrangement. The formed positions of the through holes 15*a* and 15*a* for arrangement (that is, the disposed positions of the three-dimensional knitted materials 10 and 10) are preferably set to positions corresponding to regions where vibration caused by motion involved in pumping of atrium and aorta (particularly "descending aorta") and motion of an aortic valve can be detected. As a result, the three-dimensional knitted materials 10 and 10 are sandwiched by the plate-shaped foam bodies 21 and 22 on the upper and lower surfaces, the peripheral edge portions are surrounded by the three-dimensional knitted material supporting member 15, and the plate-shaped foam bodies 21 and 22 and the three-dimensional knitted material supporting member 15 function as a resonance box (resonant box). The wall of an aorta is rich in elasticity among arteries and can receive a high pressure of blood directly pumped out of the heart, and an aortic valve which is a valve for preventing a backflow is located immediately out of the left ventricle of the heart. Thus, by arranging the position of the three-dimensional knitted material at the above-described position, a motion of a negative feedback mechanism of the brain and the autonomic nerve system for maintaining homeostasis of a biological body can be well captured.

Moreover, it is preferable that the three-dimensional knitted materials 10 and 10 are thicker than the three-dimensional knitted material supporting member 15 in use. That is, such a thickness relationship is realized that, when the three-dimensional knitted materials 10 and 10 are arranged in the through holes 15*a* and 15*a* for arrangement, the front surfaces and the back surfaces of the three-dimensional knitted materials 10 and 10 protrude from the through holes 15*a* and 15*a* for arrangement. As a result, when the peripheral edge portions of the films 16 and 16 are bonded to the peripheral edge portions of the through holes 15*a* and 15*a* for arrangement, the three-dimensional knitted materials 10 and 10 are pressed in the thickness direction. Therefore, a tensile force caused by a reaction force of the films 16 and 16 is generated, and the solid vibration (membrane vibration) can easily occur in the films 16 and 16. On the other hand, preliminary compression occurs also in the three-dimensional knitted materials 10 and 10, and a tension caused by the reaction force is generated also in the connecting fiber maintaining the thickness form of the three-dimensional knitted materials, thereby the string vibration can easily occur. The films 16 and 16 are preferably provided on both sides of the front sides and the back sides of the three-dimensional knitted materials 10 and 10, but it is possible to configure such that the film 16 is provided on at least either one of them.

Since the connecting fiber of the three-dimensional knitted materials 10 and 10 is extended between the pair of ground knitted fabrics, it becomes a long string wound in a so-called coil shape, and the films 16 and 16 and the plate-shaped foam bodies 21 and 22 functioning as the resonance box (resonant box) are disposed at upper and lower node points. Since the biological signal represented by heart rate fluctuation has a low frequency, it is amplified by the resonance system provided with the long string and the large number of node points. That is, the string vibration of the connecting fiber causes the membrane vibration of the films 16 and 16 and the membrane vibration of the beads of the plate-shaped foam bodies 21 and 22 to be generated through the large number of node points, whereby they are superposed in action and are amplified. The interval between the node points of the connecting fiber of the three-dimensional knitted materials, that is, the arrangement density of the connecting fiber is higher the better.

Moreover, it is possible to configure such that the films 16 and can be arranged on the front side and the back side of the three-dimensional knitted materials 10 and 10 only by bonding the films 16 and 16 on the plate-shaped foam bodies 21 and 22 side in advance to be integrated and by stacking the plate-shaped foam bodies 21 and 22 on the three-dimensional knitted material supporting member 15. However, in order to give the preliminary compression to the three-dimensional knitted materials 10 and 10, the films 16 and 16 are preferably fastened to the surface of the three-dimensional knitted material supporting member 15 as described above. Moreover, instead of disposition of the films in correspondence with each three-dimensional knitted material 10 as in FIG. 1, it is possible to use the film 16 having a size that can cover both the two three-dimensional knitted materials 10 and 10 as illustrated in FIG. 2.

As the films 16 and 16, a plastic film made of polyurethane elastomer (product number "DUS605-CDR" by Sheedom Co., Ltd., for example) is preferably used in order to capture heart rate fluctuation, for example. However, if natural frequencies of the films 16 and 16 match each other, the membrane vibration is generated by resonance and thus, the above is not limiting but those having the natural frequency according to the target to be sampled (heart rate, respiration, atrial and aortic oscillations and the like) are preferably used. For example, as will be illustrated in a test example which will be described later, a material with small stretch properties such as an unwoven cloth made of thermoplastic polyester (a biaxial woven fabric (warp: 20 fibers/inch, weft: 20 fibers/inch) formed from a polyethylene naphthalate (PEN) fiber (1100 dtex) by Teijin, for example) can be also used. Moreover, an elastic fiber unwoven cloth having an elongation degree of 200% or more and a recovery rate at 100%-elongation is 80% or more (product name "Espansione" by KB Seiren Ltd., for example) can be also used, for example.

The vibration sensor 30 is fastened and disposed on either one of the three-dimensional knitted materials 10 before the above-described films 16 and 16 are laminated. The three-dimensional knitted material 10 is composed of a pair of ground knitted fabrics and the connecting fiber, and since the string vibration of each connecting fiber is transmitted to the films 16 and 16 and the plate-shaped foam bodies 21 and 22 through the node points with the ground knitted fabrics, the vibration sensor 30 is preferably fastened to the surface of the three-dimensional knitted material 10 (surface of the ground knitted fabric) at a sensing portion 30a. As the vibration sensor 30, a microphone sensor or particularly a capacitor-type microphone sensor is preferably used. In this embodiment, since it is not necessary to consider sealing performance at a portion where the microphone sensor is arranged (that is, the through hole 15a for arrangement in which the three-dimensional knitted material 10 is arranged), a lead wire of the microphone sensor can be wired easily. In this embodiment, as described above, the vibration on the body surface through the muscle of a human being involved in the biological signal is propagated not only to the three-dimensional knitted material 10 but also to the plate-shaped foam bodies 21 and 22 and the film 16, and they are vibrated (string vibration, membrane vibration), the superposed and amplified. Thus, the vibration sensor 30 can fix the sensing portion 30a not only to the three-dimensional knitted material 10 but also to the plate-shaped foam bodies 21 and 22 and the film 16 constituting a vibration transmission path. In this embodiment, since the three-dimensional knitted material 10, the three-dimensional knitted material supporting member 15, the plate-shaped foam bodies 21 and 22, and the film 16 mechanically amplify the biological signal, they constitute the mechanical amplification device.

The biological signal measuring means 1 described above is arranged inside a skin 120 covering a seatback frame 110 of the vehicle seat 100 as illustrated in FIG. 3, for example. In order to facilitate an arrangement work, the three-dimensional knitted material 10, the three-dimensional knitted material supporting member 15, the film 16, the plate-shaped foam bodies 21 and 22, the vibration sensor 30 and the like constituting the biological signal measuring means 1 are preferably unitized in advance.

The above-described biological signal measuring means 1 has a mechanical amplification device provided with the three-dimensional knitted material 10 and the plate-shaped foam bodies 21 and 22 stacked around the three-dimensional knitted material 10, preferably a mechanical amplification device in which a film 16 is disposed between the three-dimensional knitted material 10 and the plate-shaped foam bodies 21 and 22. The biological signal measuring means 1 is configured such that a vibration sensor is attached to this mechanical amplification device. Micro vibration on the body surface caused by a biological signal of a human being such as heart rate, respiration, atrial and aortic vibrations and the like is propagated to the plate-shaped foam bodies 21 and 22, the film 16, and the three-dimensional knitted material 10, and membrane vibration is generated in the plate-shaped foam bodies 21 and 22 and the film 16, while string vibration of a fiber is generated in the three-dimensional knitted material.

Moreover, the three-dimensional knitted material 10 is formed such that the connecting fibers are disposed between the pair of ground knitted fabrics and is provided with a load-deflection characteristic close to the load-deflection characteristic of a human muscle. Therefore, by making the load-deflection characteristic of the mechanical amplification device including the three-dimensional knitted material 10 close to that of a muscle and by disposing the device adjacent to the muscle, a difference between internal and external pressures between the muscle and the three-dimensional knitted material becomes equal, and a biological signal such as heart rate, respiration, atrial and aortic vibrations and the like can be transmitted accurately, whereby the string vibration can be generated in a fiber (or particularly the connecting fiber) constituting the three-dimensional knitted material 10. Moreover, the plate-shaped foam bodies 21 and 22 stacked on the three-dimensional knitted material 10, preferably a bead foam body, can easily generate membrane vibration in each bead due to flexible elasticity and small density of the bead. The film 16 can easily generate membrane vibration since a predetermined tension is generated by means of fixing the peripheral edge portion of the film 16 and elastically supporting the film 16 by the three-dimensional knitted material close to the load-deflection characteristic of a human muscle. That is, according to the biological signal measuring means 1, the membrane vibration is generated in the plate-shaped foam bodies 21 and 22 and the film 16 in the mechanical amplification device having the load-deflection characteristic close to the load-deflection characteristic of the muscle by a biological signal such as heart rate, respiration, atrial and aortic oscillations and the like, and the string vibration is generated in the three-dimensional knitted material 10 having the load-deflection characteristic close to the load-deflection characteristic of the human muscle. The string vibration of the three-dimensional knitted material 10 influences the membrane vibration of the film 16 and the like again, and these vibrations act in a superposed manner. As a result, the vibration inputted from the body surface with the biological signal is directly detected by the vibration sensor 30 as solid vibration amplified by superposition of the string vibration and the membrane vibration.

As the biological signal measuring means 1 used in the present invention, a configuration which detects air pressure fluctuation within a sealed bag as before can be used, but since a volume and pressure are inversely proportional to each other, it is difficult to detect pressure fluctuation unless the volume of the sealing bag is made small. On the other hand, since the biological signal measuring means 1 described above detects an amplified solid vibration transmitted to the mechanical amplification device (the three-dimensional knitted material 10, the plate-shaped foam bodies 21 and 22, and the film 16), as described above, instead of the air pressure fluctuation, the volume (cubic volume) is hardly limited from the viewpoint of detection sensitivity, so that a vibration with small amplitude involved in heart rate, respiration, atrial and aortic oscillations and the like can be detected with a high sensitivity. Therefore, the means can accommodate persons having various physical builds. Accordingly, the biological signal measuring means 1 can detect a biological signal with a high sensitivity even under an environment such as a vehicle seat used by people with various physical sizes and into which various external vibrations are inputted. Moreover, since it is not necessary to form a sealed structure, a manufacturing process is simplified, and a manufacturing cost is lowered, which are suitable for mass production.

The above-described biological signal measuring means 1 is incorporated in the inside of a skin 120 of the seat 100 but may be incorporated in a seat cushion attached to the surface of the skin 120 afterwards. However, in the case of attachment afterwards, it is preferable to provide a hard face such as a three-dimensional knitted material with high planar stiffness or to insert a plate having a thickness of approximately 1 to 2 mm made of a synthetic resin such as polypropylene between the seat and the three-dimensional knitted material so that preliminary compression can be easily generated in the three-dimensional knitted material by body weight. For example, in the case of a seat with soft compression characteristics, the three-dimensional knitted material is not preliminarily compressed and thus, a biological signal is not reflected but absorbed. However, by providing a hard face as above, the fluctuation in the compression characteristics on the seat side as above is absorbed, and a biological signal with large amplitude can be obtained easily.

Figure 4:
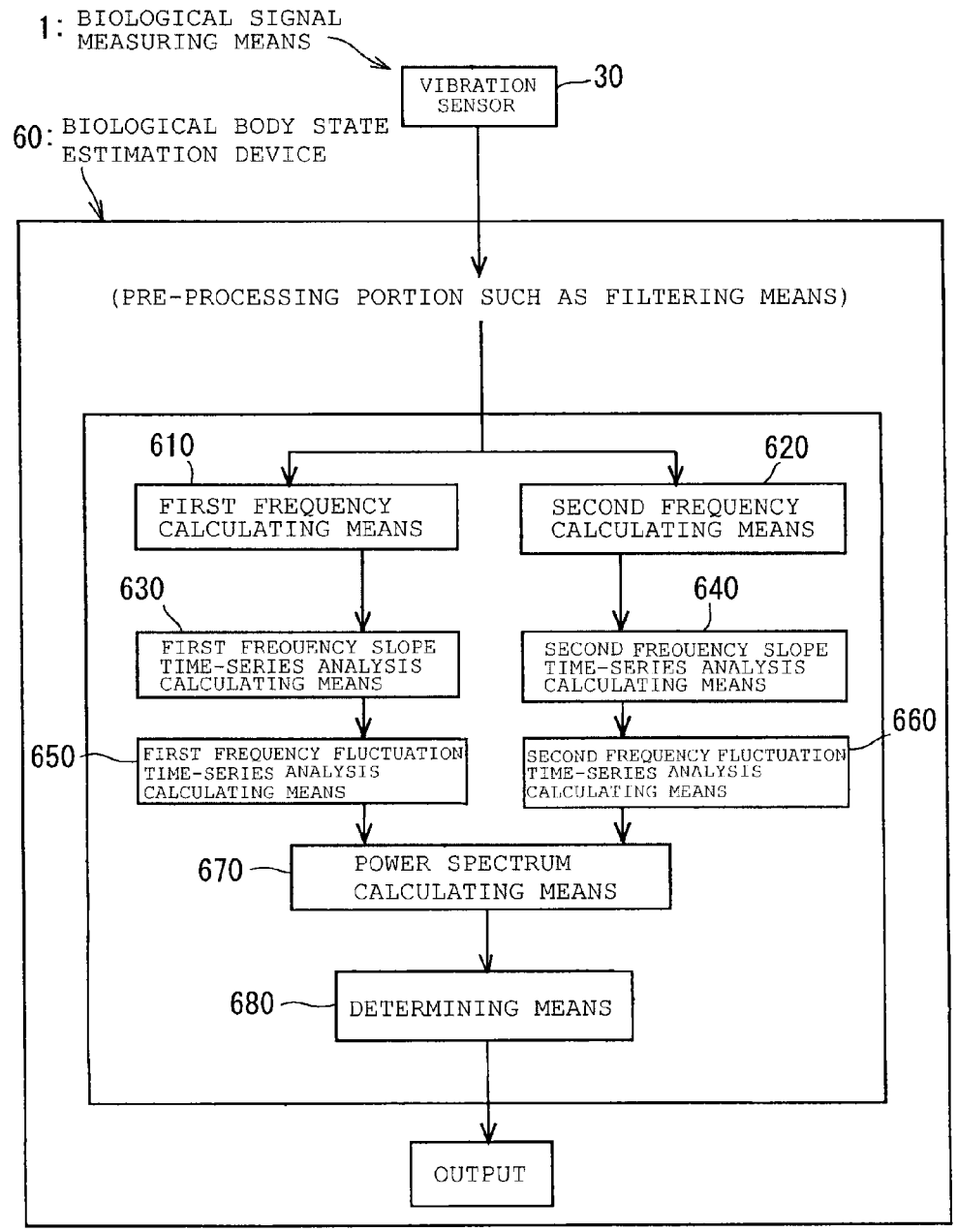
FIG. 4 is a diagram illustrating a configuration of a biological body state estimation device according to the embodiment of the present invention.

Subsequently, the configuration of the biological body state estimation device 60 will be described on the basis of FIG. 4. The biological body state estimation device 60 is configured by having a first frequency calculating means (first frequency calculating step) 610, a second frequency calculating means (second frequency calculating step) 620, a first frequency slope time-series analysis calculating means (first frequency slope time-series analysis calculating step) 630, a second frequency slope time-series analysis calculating means (second frequency slope time-series analysis calculating step) 640, a first frequency fluctuation time-series analysis calculating means (first frequency fluctuation time-series analysis calculating step) 650, a second frequency fluctuation time-series analysis calculating means (second frequency fluctuation time-series analysis calculating step) 660, a power spectrum calculating means (power spectrum calculating step) 670, a determining means (determining step) 680 and the like, composed of a computer program set in a storage portion such as a hard disk. The computer program can be provided by being stored in a recording medium such as a flexible disk, a hard disk, a CD-ROM, an MO (magnet-optic disk), a DVD-ROM, a memory card and the like or can be also transmitted via a communication line.

The first and second frequency calculating means (first and second frequency calculating steps) 610 and 620 acquire a time-series waveform of a frequency in time-series data of an output signal obtained from the vibration sensor 30 of the biological signal measuring means 1 (or preferably the time-series data of a predetermined frequency area subjected to filtering processing). Among them, the first frequency calculating means 610 relates to LF/HF used as an index of a sympathetic nerve function, while the second frequency calculating means 620 relates to HF used as an index of a parasympathetic nerve function.

Specifically, the first frequency calculating means 610 is a method of acquiring a time-series waveform of a frequency using a point of switching from positive to negative (hereinafter referred to as a "zero-crossing point") in the time-series waveform of the output signal obtained from the vibration sensor of the biological signal measuring means 1 (hereinafter referred to as a "zero-crossing method"). This zero-crossing method captures a basic component of the frequency of a biological signal and indicates whether or not a frequency equilibrium state is realized by an action of an adjustment function in the nerve center which is a negative feedback mechanism in the frequency adjustment and indicates a strength level of emergence of the LF/HF. In this method, first, after the zero-crossing point is acquired, it is divided into 5 seconds each, for example, a reciprocal number of time interval between the zero-crossing points of the time-series waveform included in the 5 seconds is acquired as an individual frequency f, and a mean value of the individual frequency f in the 5 seconds is employed as a value of a frequency F in the 5 seconds (step [1] in FIG. 5). Then, by plotting the frequency F obtained at this 5 seconds each, a time-series waveform of the frequency is acquired (step [2] in FIG. 5).

The second frequency calculating means 620 is a method of acquiring a time-series waveform using a maximum value (peak) by applying smoothing differentiation to a time-series waveform of an output signal obtained from the vibration sensor of the biological signal measuring means 1 (hereinafter referred to as a "peak detection method"). The peak detection method is basically a time-series waveform corresponding to a function of HF. For example, a maximum value is acquired by a smoothing differentiation method of Savitzky and Golay. Subsequently, the maximum value is divided into 5 seconds each, for example, a reciprocal number of the time interval between the maximum values (mountain-side top portions of a waveform) of the time-series waveform included in the 5 seconds is acquired as an individual frequency f, and a mean value of the individual frequency f in the 5 seconds is employed as a value of a frequency F in the 5 seconds (step [1] in FIG. 5). Then, by plotting the frequency F obtained at this 5 seconds each, a time-series waveform of the frequency is acquired (step [2] in FIG. 5).

The first and second frequency slope time-series analysis calculating means (first and second frequency slope time-series analysis calculating steps) 630 and 640 are configured to set a time window of a predetermined time width from a time-series waveform of a frequency of an output signal of the vibration sensor of the biological signal measuring means 1 obtained using the zero-crossing method or the peak detection method by the first and second frequency calculating means 610 and 620, a slope of the frequency of the output signal of the vibration sensor is acquired at each time window by using the least-square method, and the time-series waveform is outputted. Specifically, a slope of a frequency at a time window Tw1 is acquired by the least-square method and plotted (steps [3] and [5] in FIG. 5). Subsequently, a subsequent time window Tw2 is set by an overlap time Tl (step [6] in FIG. 5), and a slope of the frequency in this time window Tw2 is similarly acquired by the least-square method and plotted. This calculation (movement calculation) is sequentially repeated, and a time-series change of the slope of the frequency of an air pack signal is outputted as a frequency slope time-series waveform (step [8] in FIG. 5). The time width of the time window Tw is preferably set to 180 seconds, and the overlap time Tl is preferably set to 162 seconds. They are selected as values at which characteristic signal waveforms emerge with the highest sensitivity from sleep experiments conducted by changing the time width of the time window Tw and the overlap time Tl as indicated in the above-described Patent Literature 3 (WO2005/092193A1) by the applicant of this application.

The first frequency slope time-series analysis calculating means (first frequency slope time-series analysis calculating step) 630 is means for acquiring a frequency slope time-series waveform from a time-series waveform of a frequency of the first frequency calculating means 610 by using the zero-crossing method, and the second frequency slope time-series analysis calculating means (second frequency slope time-series analysis calculating step) 640 is means for acquiring a frequency slope time-series waveform from a time-series waveform of a frequency of the second frequency calculating means 620 by using the peak detection method. The frequency slope time-series waveform obtained by the first frequency slope time-series analysis calculating means 630 by using the zero-crossing method indicates fluctuation of a biological body capturing a balance of emergences of the sympathetic nerve and the parasympathetic nerve, and the time-series waveform acquired by the second frequency slope time-series analysis calculating means 640 by using the peak detection method indicates fluctuation of a biological body capturing a state of the parasympathetic nerve.

Figure 5:
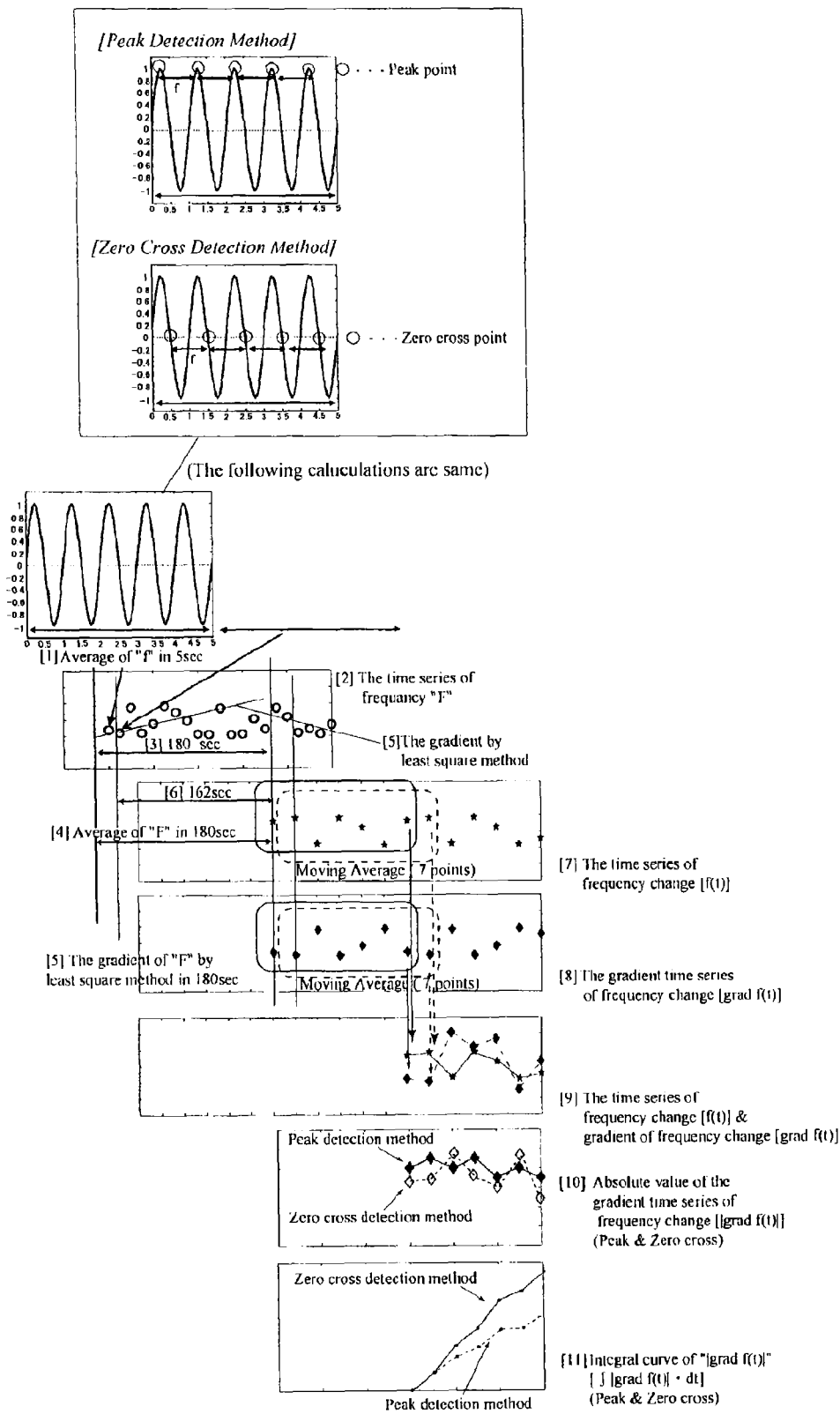
FIG. 5 is a diagram for explaining a method of acquiring a frequency fluctuation time-series waveform, a base line of the frequency fluctuation time-series waveform, and a frequency slope time-series waveform which is a slope time-series of frequency fluctuation by using a peak value or a zero-crossing point of a biological signal detected by the biological signal measuring means.

The first and second frequency fluctuation time-series analysis calculating means (frequency fluctuation time-series analysis calculating steps) 650 and 660 set a time window having a predetermined time width (preferably 180 seconds) to a time-series waveform of the frequency of an output signal from the vibration sensor of the biological signal measuring means 1 obtained by the first and second frequency calculating means 610 and 620 (step [2] in FIG. 5) and acquire a mean value of the frequency (steps [3] and [4] in FIG. 5). Subsequently, movement calculation for acquiring a mean value of the frequency of the output signal of the vibration sensor at each predetermined time window (preferably 180 seconds) set by a predetermined overlap time (preferably 162 seconds) is conducted and the value is plotted. And a time-series change of the mean value of the frequency plotted at each time window is outputted as a frequency fluctuation time-series waveform (step [7] in FIG. 5). Then, when the frequency slope time-series waveform and the frequency fluctuation time-series waveform are outputted together, it proceeds to step [9] in FIG. 5. A heart rate can be also acquired from the frequency fluctuation time-series waveform.

The first frequency fluctuation time-series analysis calculating means (first frequency fluctuation time-series analysis calculating step) 650 is means for acquiring a frequency fluctuation time-series waveform from the time-series waveform of the frequency of the first frequency calculating means 610 by using the zero-crossing method, while the second frequency fluctuation time-series analysis calculating means (second frequency fluctuation time-series analysis calculating step) 660 is means for acquiring a frequency slope time-series waveform from the time-series waveform of the frequency of the second frequency calculating means 620 by using the peak detection method.

The power spectrum calculating means (power spectrum calculating step) 670 is means for applying frequency analysis to the frequency slope time-series waveform obtained by the first frequency slope time-series analysis calculating means 630, the frequency slope time-series waveform obtained by the second frequency slope time-series analysis calculating means 640, the frequency fluctuation time-series waveform obtained by the first frequency fluctuation time-series analysis calculating means 650, and the frequency fluctuation time-series waveform obtained by the second frequency fluctuation time-series analysis calculating means 660, respectively, and for acquiring a power spectrum of each frequency corresponding to the above-described functional adjustment signal, fatigue reception signal, and activity adjustment signal, respectively.

Here, as described above, the fatigue reception signal is a signal in the vicinity of 0.0033 Hz (a range of 0.002 to 0.0052 Hz), the activity adjustment signal is a signal in the vicinity of 0.0055 Hz (a range of 0.004 to 0.007 Hz), and the functional adjustment signal is a signal in the vicinity of the frequency approximately ½ of the fatigue reception signal (a range of 0.0027 Hz or less). However, as the result of frequency analysis and adjustment of a large quantity of data by the inventors, 0.00179 Hz within the range of 0.0027 Hz or less which is a condition of the functional adjustment signal is set as a standard frequency of the functional adjustment signal, 0.00358 Hz which is double of 0.00179 Hz within the range of 0.002 to 0.0052 Hz which is a condition of the fatigue reception signal is set as a standard frequency of the fatigue reception signal, and 0.00537 Hz which is three times of 0.00179 Hz within the range of 0.004 to 0.007 Hz which is a condition of the activity adjustment signal is set as a standard frequency of the activity adjustment signal. This will be described in detail in test examples which will be described later.

The determining means (determining step) 680 compares and determines a time-series change of the magnitude of a power spectrum of a frequency corresponding to each of the functional adjustment signal, the fatigue reception signal, and the activity adjustment signal acquired by the power spectrum calculating means 670. The larger the value is, the more increase progresses the power spectrum indicates.

The determining means 680, first, has means (step) for outputting a time-series change of the power spectrum of each frequency corresponding to the functional adjustment signal, the fatigue reception signal, and the activity adjustment signal acquired by the power spectrum calculating means 670 by using the frequency slope time-series waveform obtained by the first frequency slope time-series analysis calculating means 630 (hereinafter referred to as a "first frequency slope time-series waveform"), acquiring a degree of relative predominance of each signal as a distribution rate and determining a state of a human being. That is because the first frequency slope time-series waveform is acquired from the frequency time-series waveform using the zero-crossing method and indicates fluctuation of a biological body, capturing a balance in emergences of the sympathetic nerve and the parasympathetic nerve and thus, it is considered as a basic index for determining the biological body state. The determining means 680 determines the state of a human being on the basis of how the power spectrum of each signal changes as time elapses, that is, how the distribution rate changes.

Figure 77:
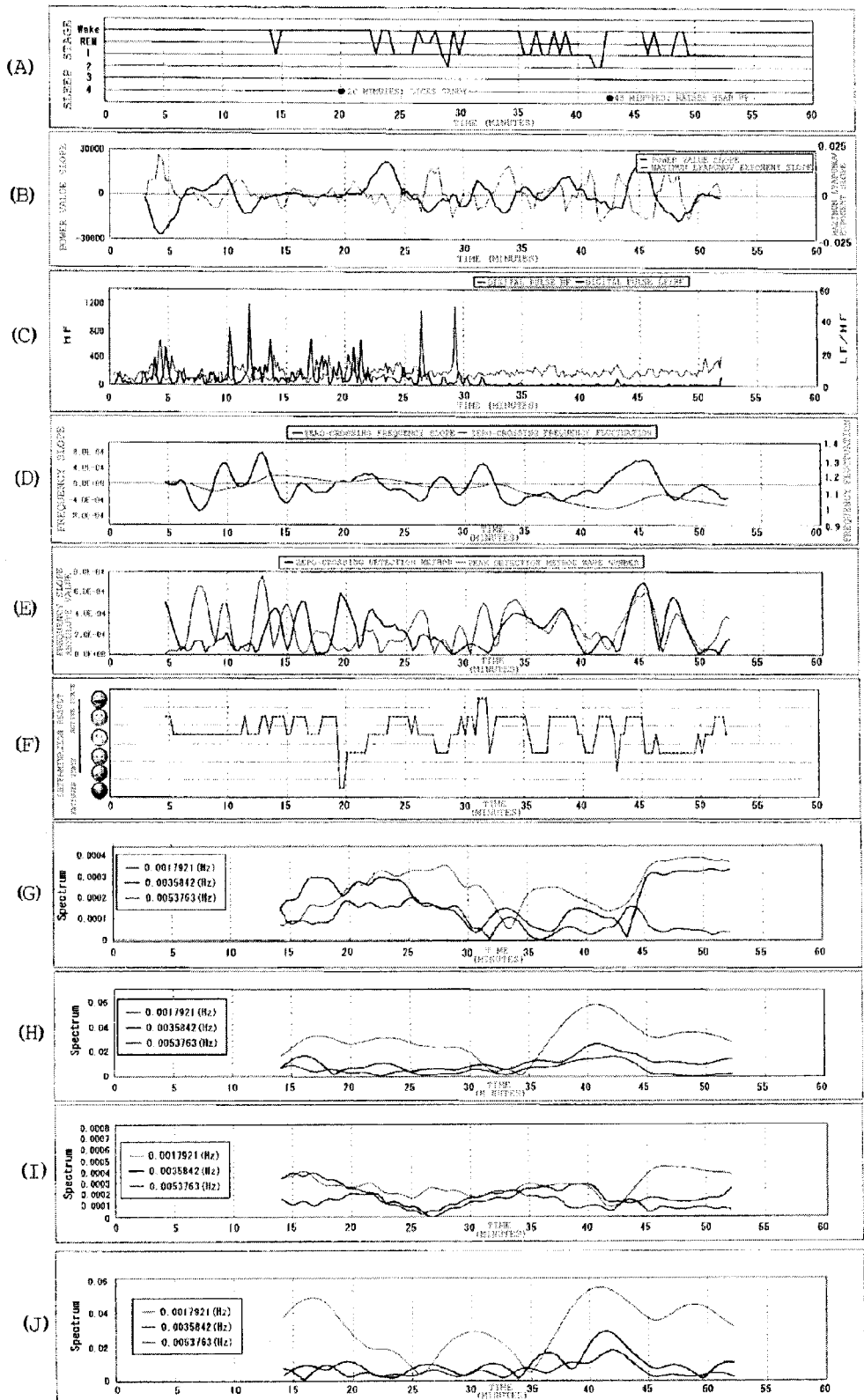
FIGS. 77(A) to 77(J) are diagrams illustrating experiment results of still another subject (male in his 40's) in the sleep introduction experiment A.
Figure 78:
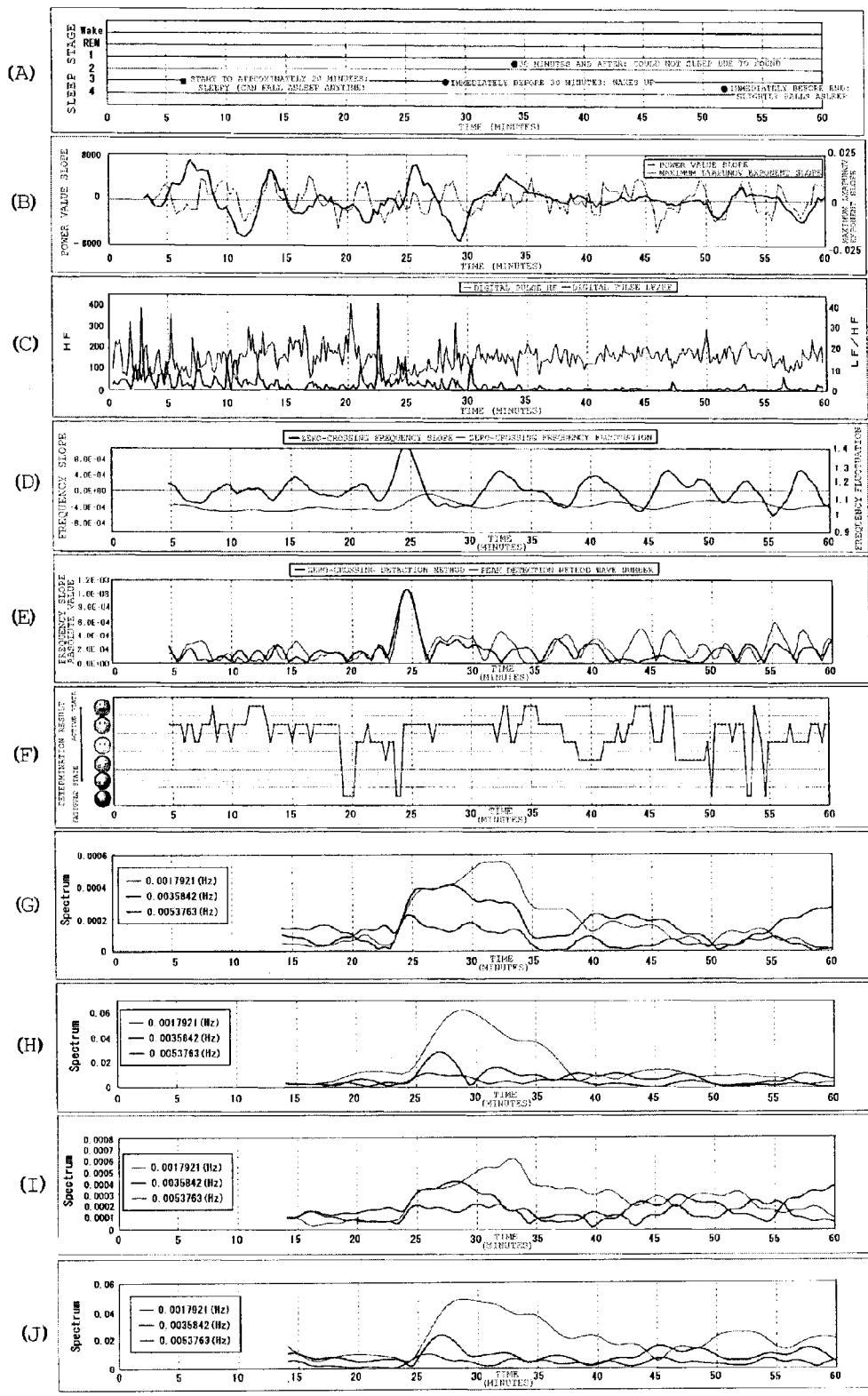
FIGS. 78(A) to 78(J) are diagrams illustrating experiment results of still another subject (male in his 40's) in the sleep introduction experiment A.
Figure 79:
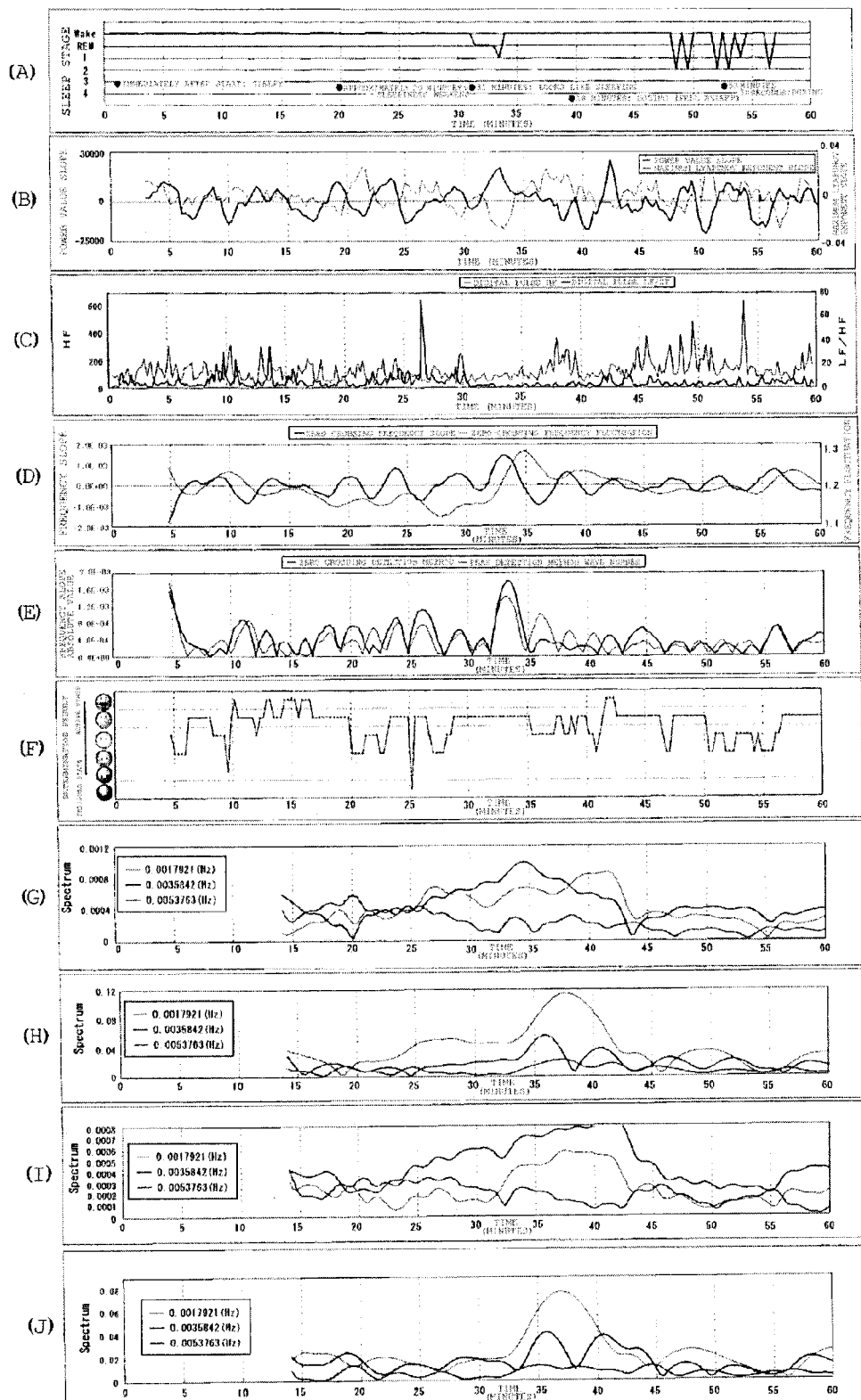
FIGS. 79(A) to 79(J) are diagrams illustrating experiment results of still another subject (male in his 30's) in the sleep introduction experiment A.
Figure 80:
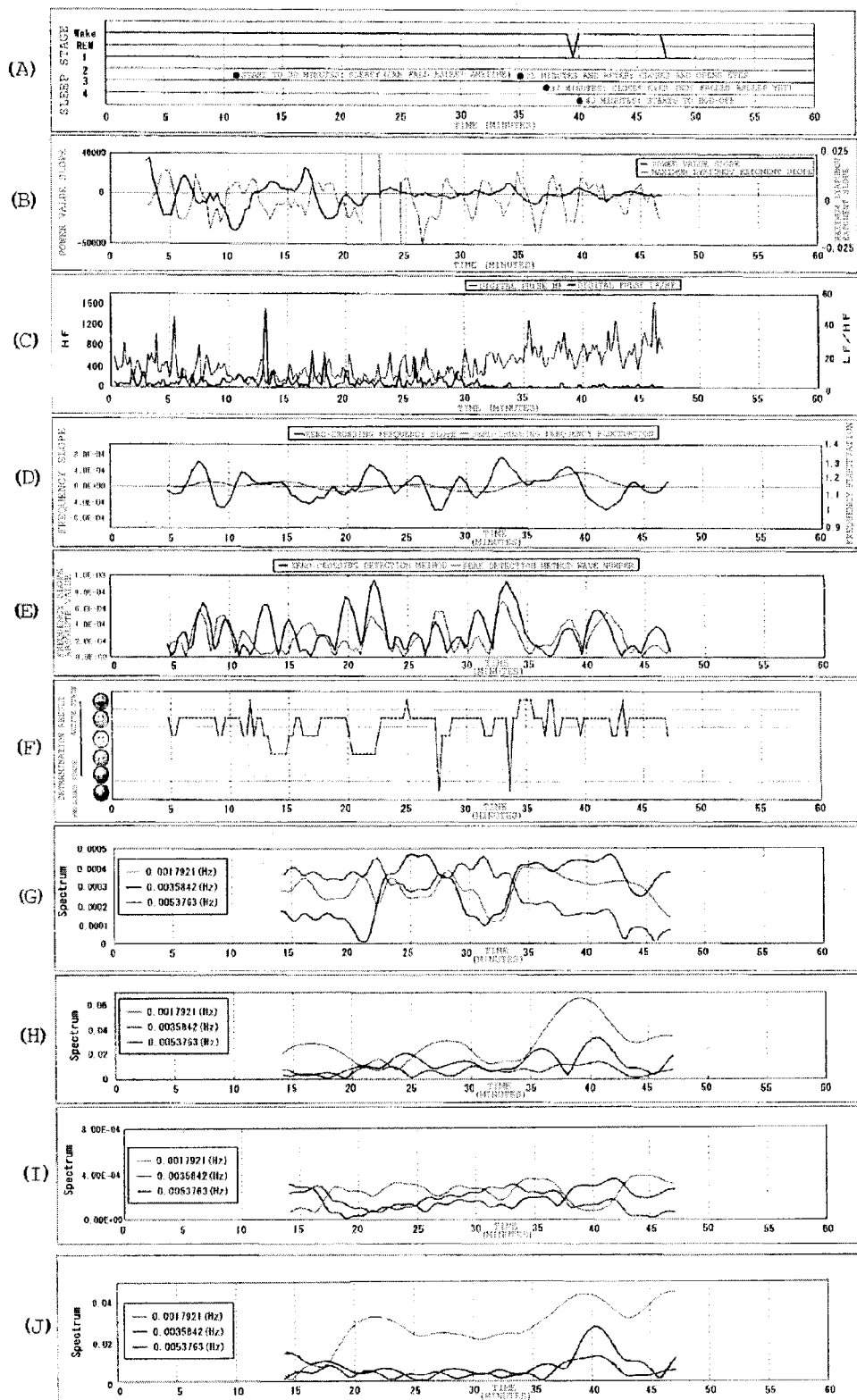
FIGS. 80(A) to 80(J) are diagrams illustrating experiment results of still another subject (male in his 40's) in the sleep introduction experiment A.
Figure 81:
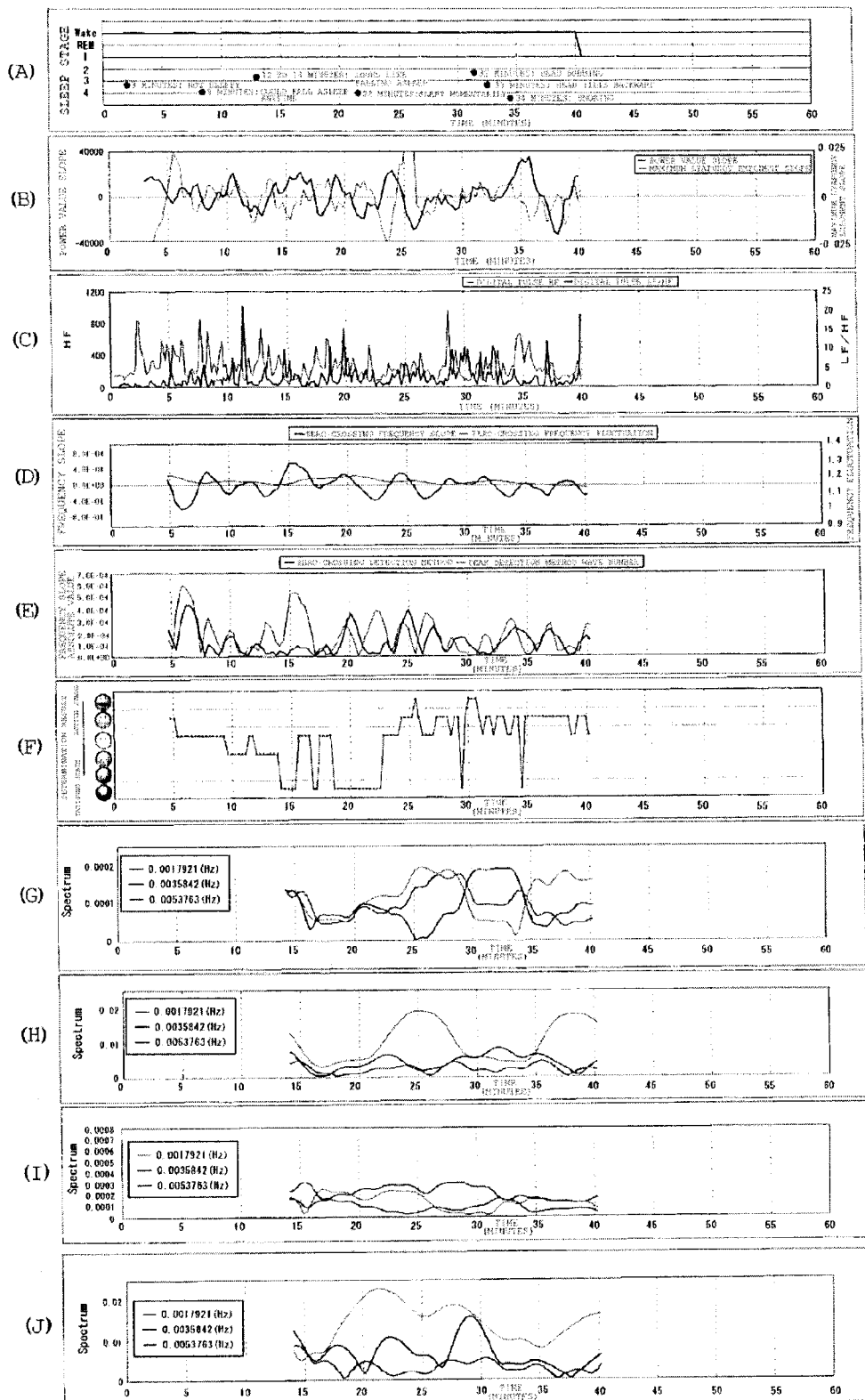
FIGS. 81(A) to 81(J) are diagrams illustrating experiment results of still another subject (male in his 40's) in the sleep introduction experiment A.
Figure 82:
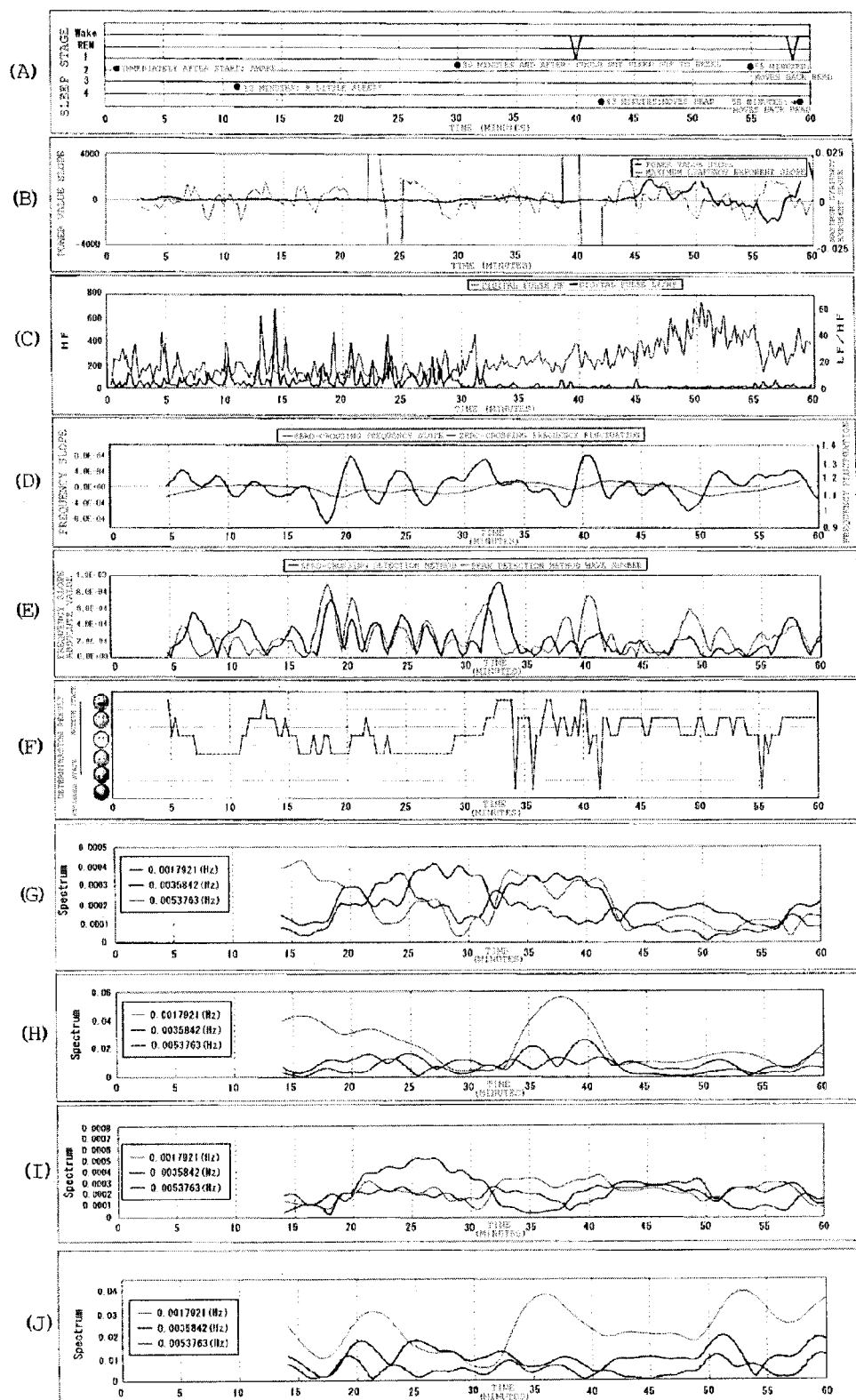
FIGS. 82(A) to 82(J) are diagrams illustrating experiment results of still another subject (male in his 40's) in the sleep introduction experiment A.
Figure 83:
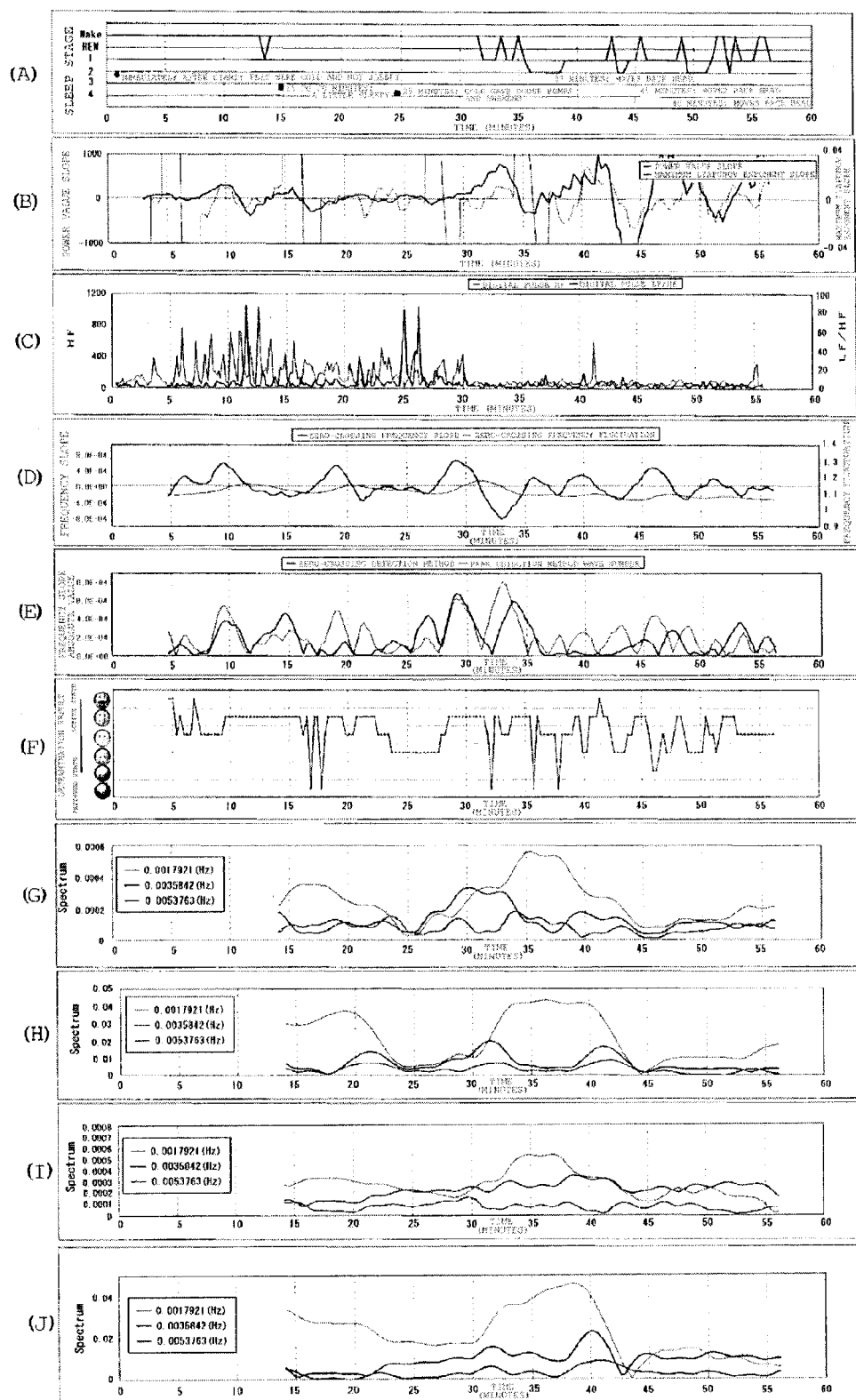
FIGS. 83(A) to 83(J) are diagrams illustrating experiment results of still another subject (male in his 40's) in the sleep introduction experiment A.
Figure 84:
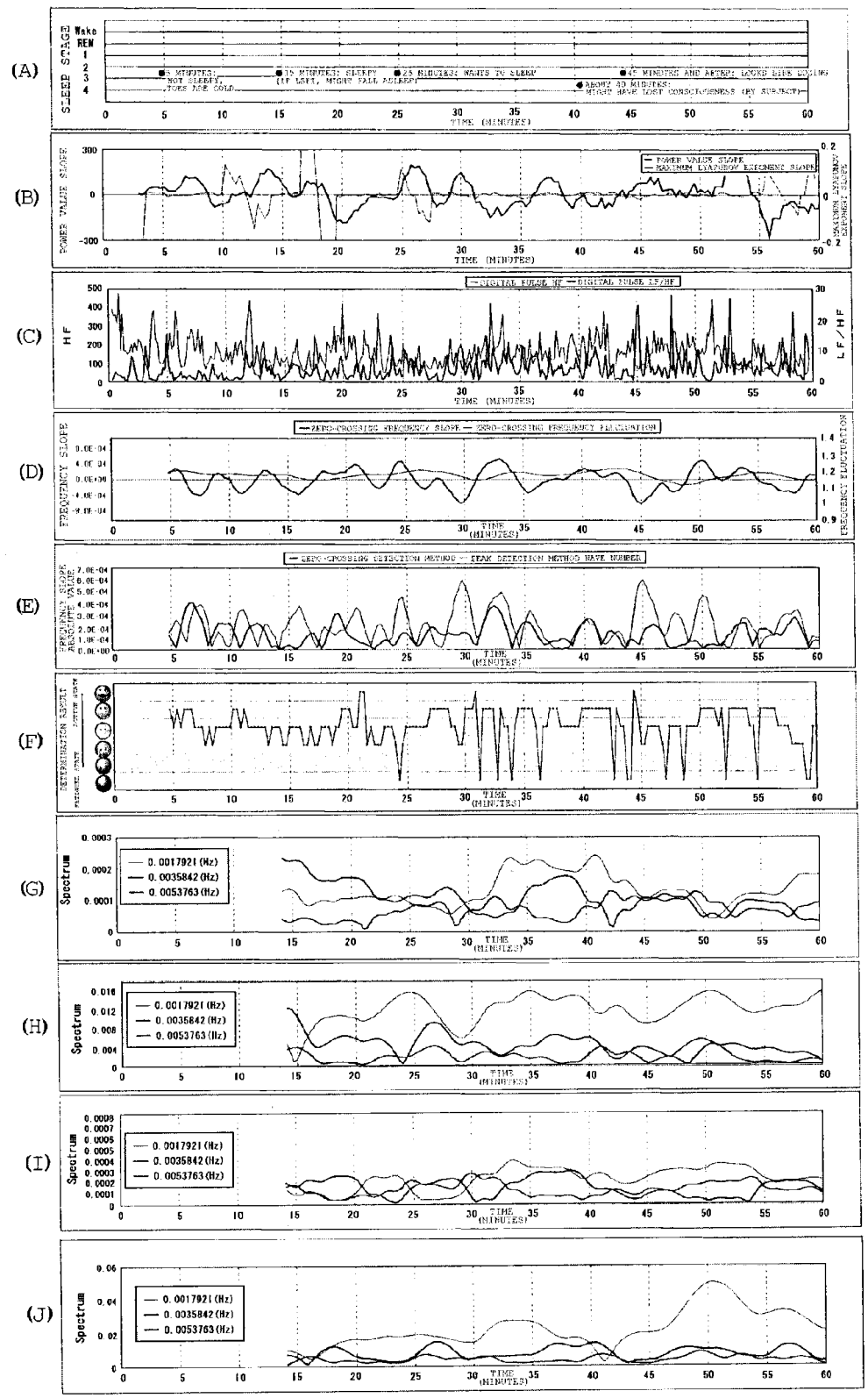
FIGS. 84(A) to 84(J) are diagrams illustrating experiment results of still another subject (male in his 30's) in the sleep introduction experiment A.
Figure 85:
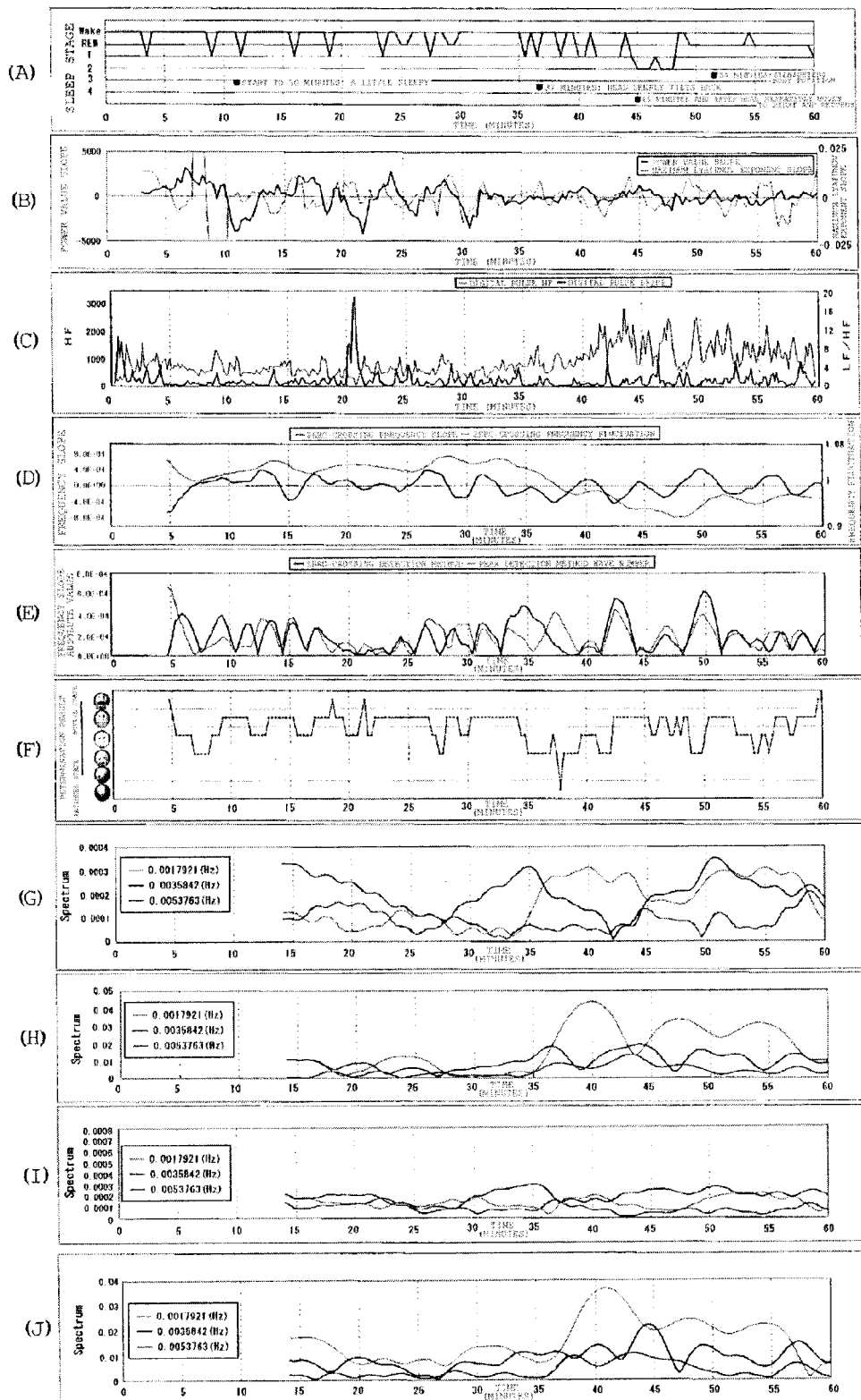
FIGS. 85(A) to 85(J) are diagrams illustrating experiment results of still another subject (male in his 20's) in the sleep introduction experiment A.
Figure 86:
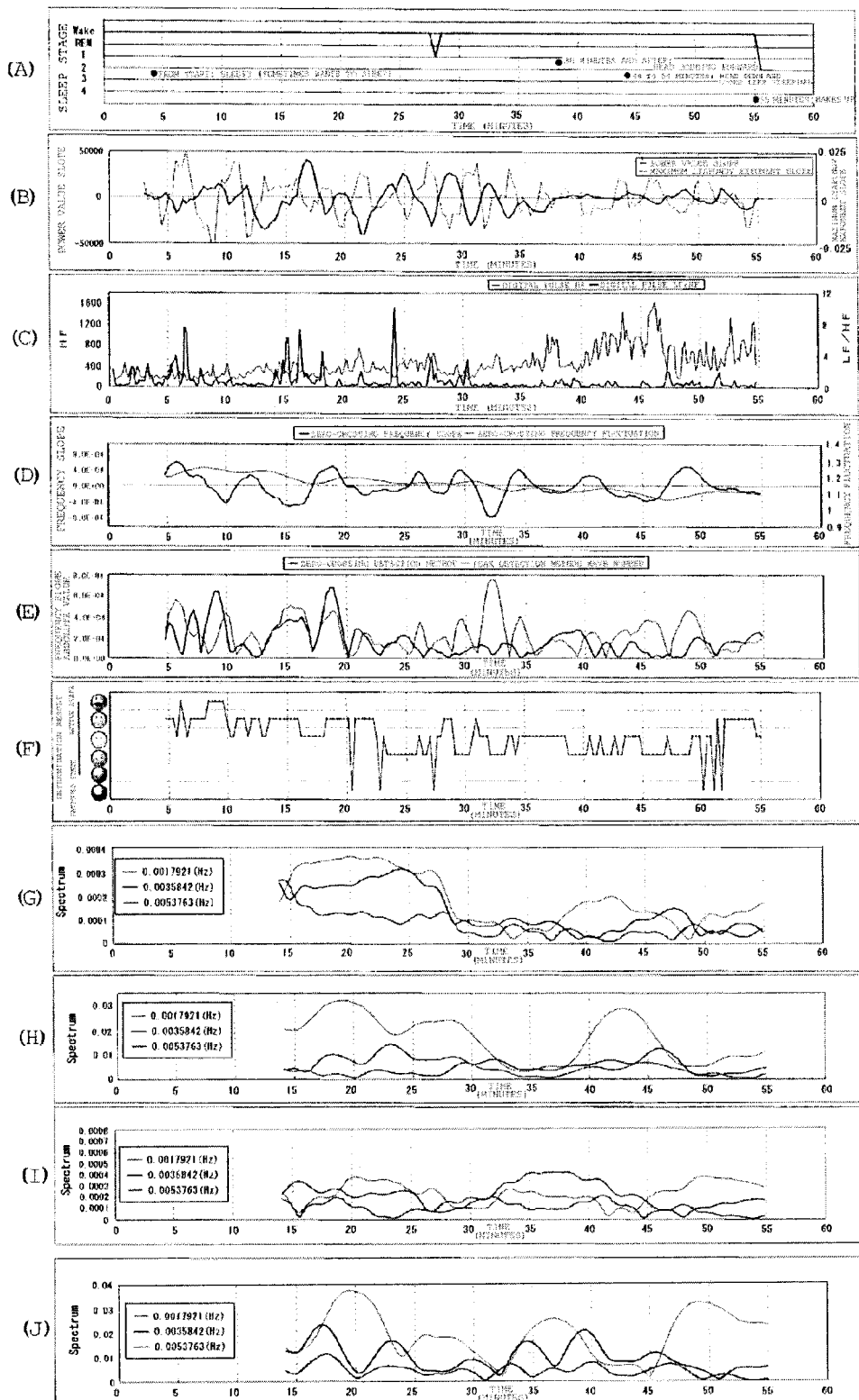
FIGS. 86(A) to 86(J) are diagrams illustrating experiment results of still another subject (male in his 40's) in the sleep introduction experiment A.
Figure 87:
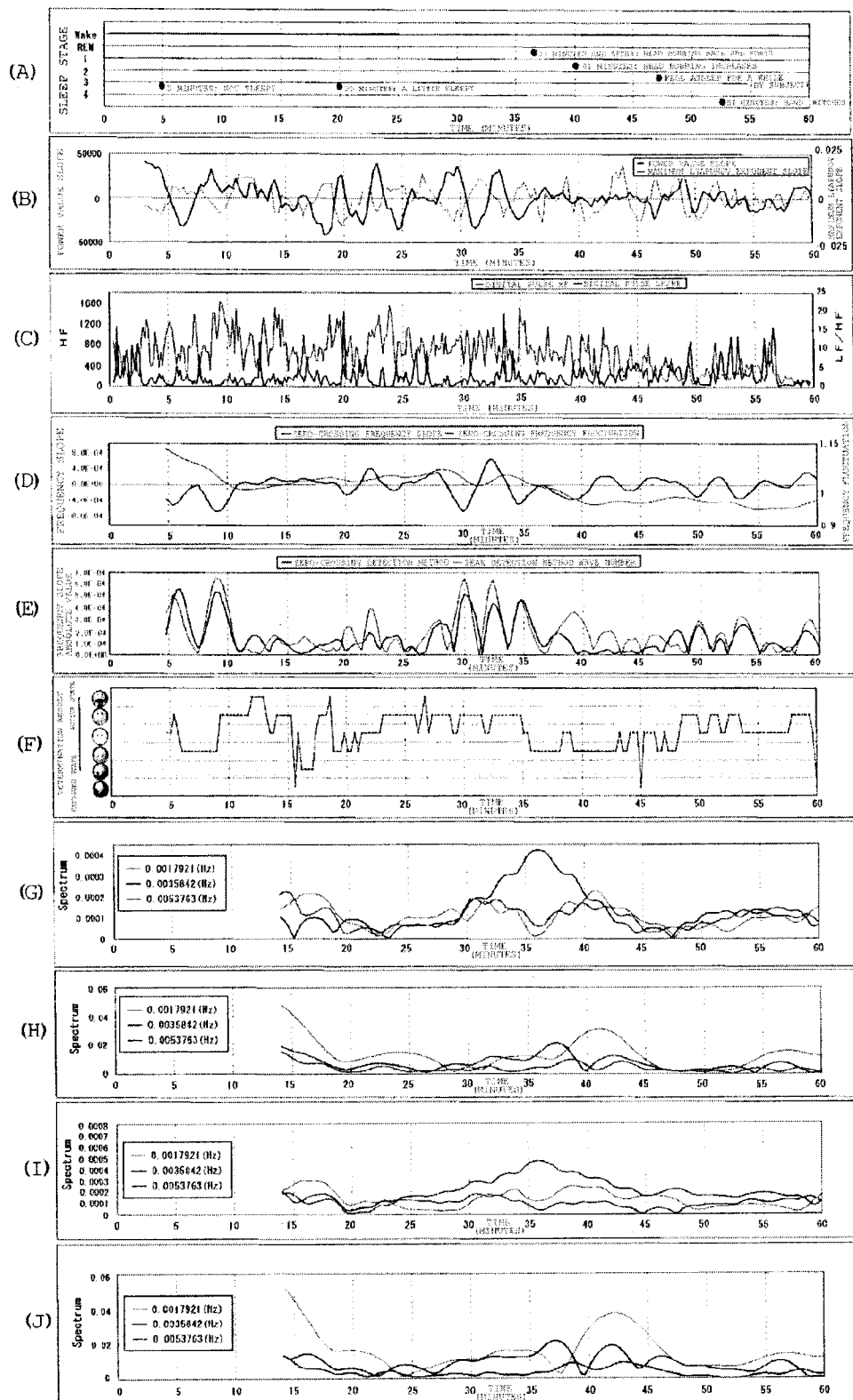
FIGS. 87(A) to 87(J) are diagrams illustrating experiment results of still another subject (male in his 30's) in the sleep introduction experiment A.
Figure 88:
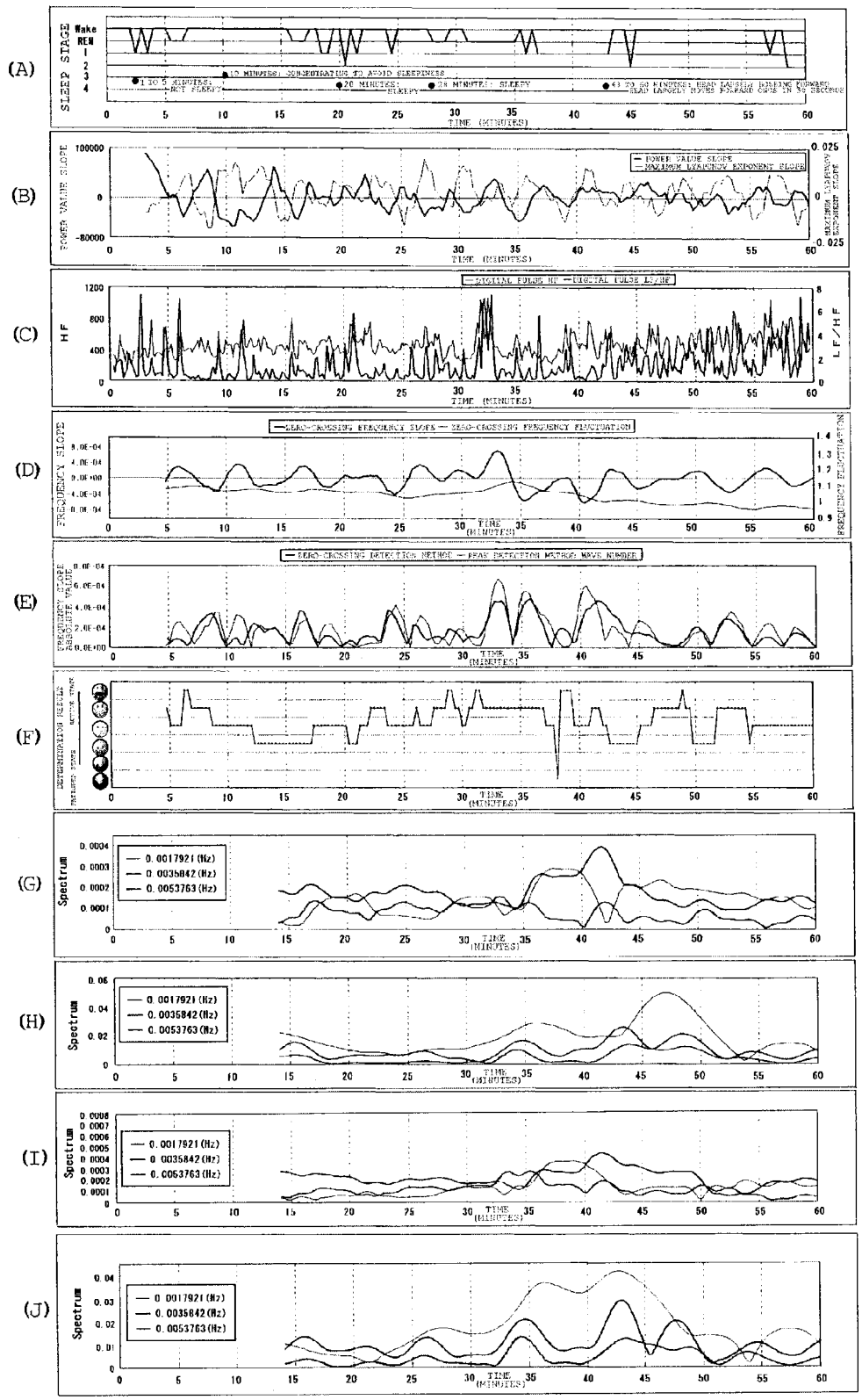
FIGS. 88(A) to 88(J) are diagrams illustrating experiment results of still another subject (male in his 40's) in the sleep introduction experiment A.
Figure 89:
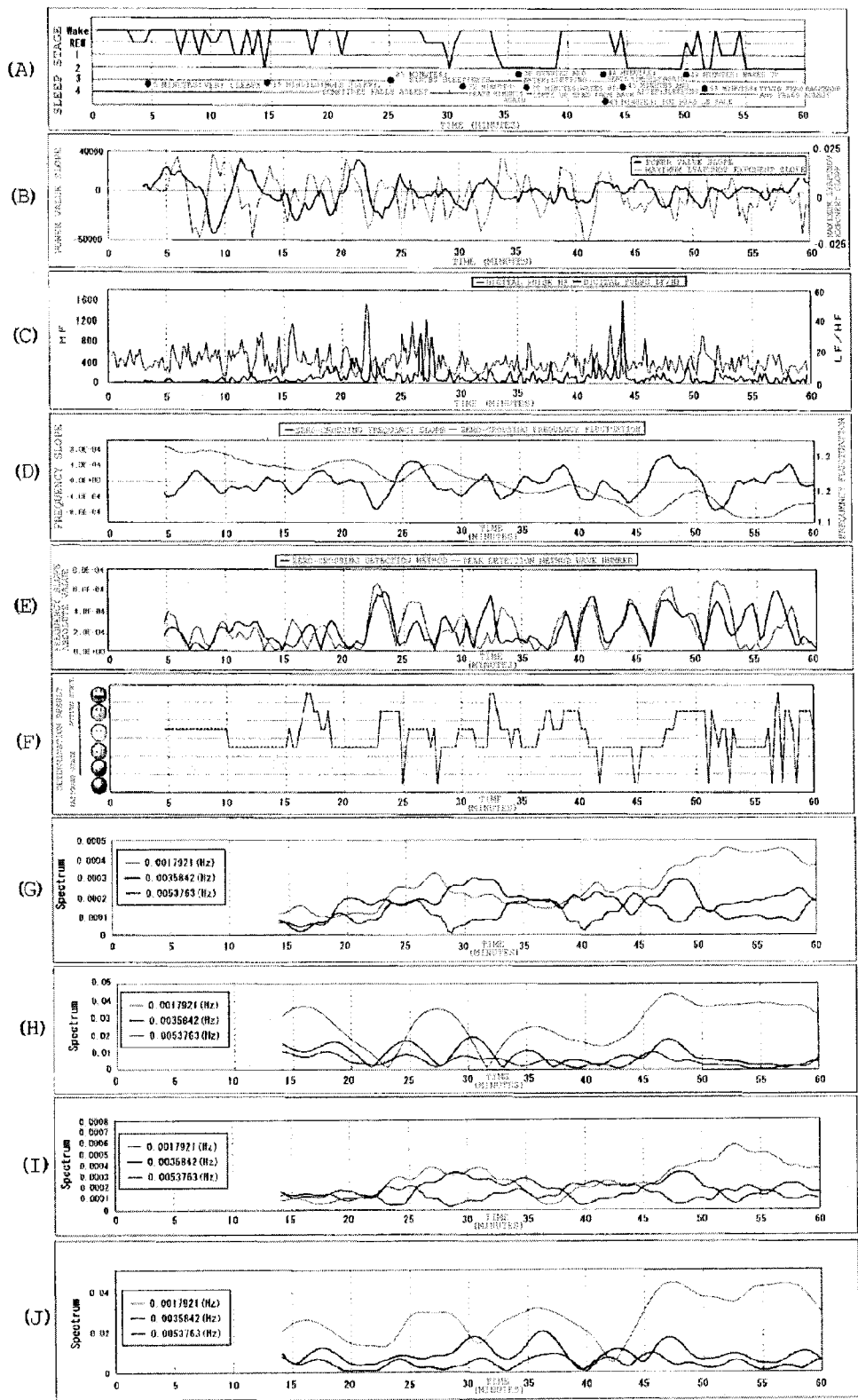
FIGS. 89(A) to 89(J) are diagrams illustrating experiment results of still another subject (male in his 30's) in the sleep introduction experiment A.
Figure 90:
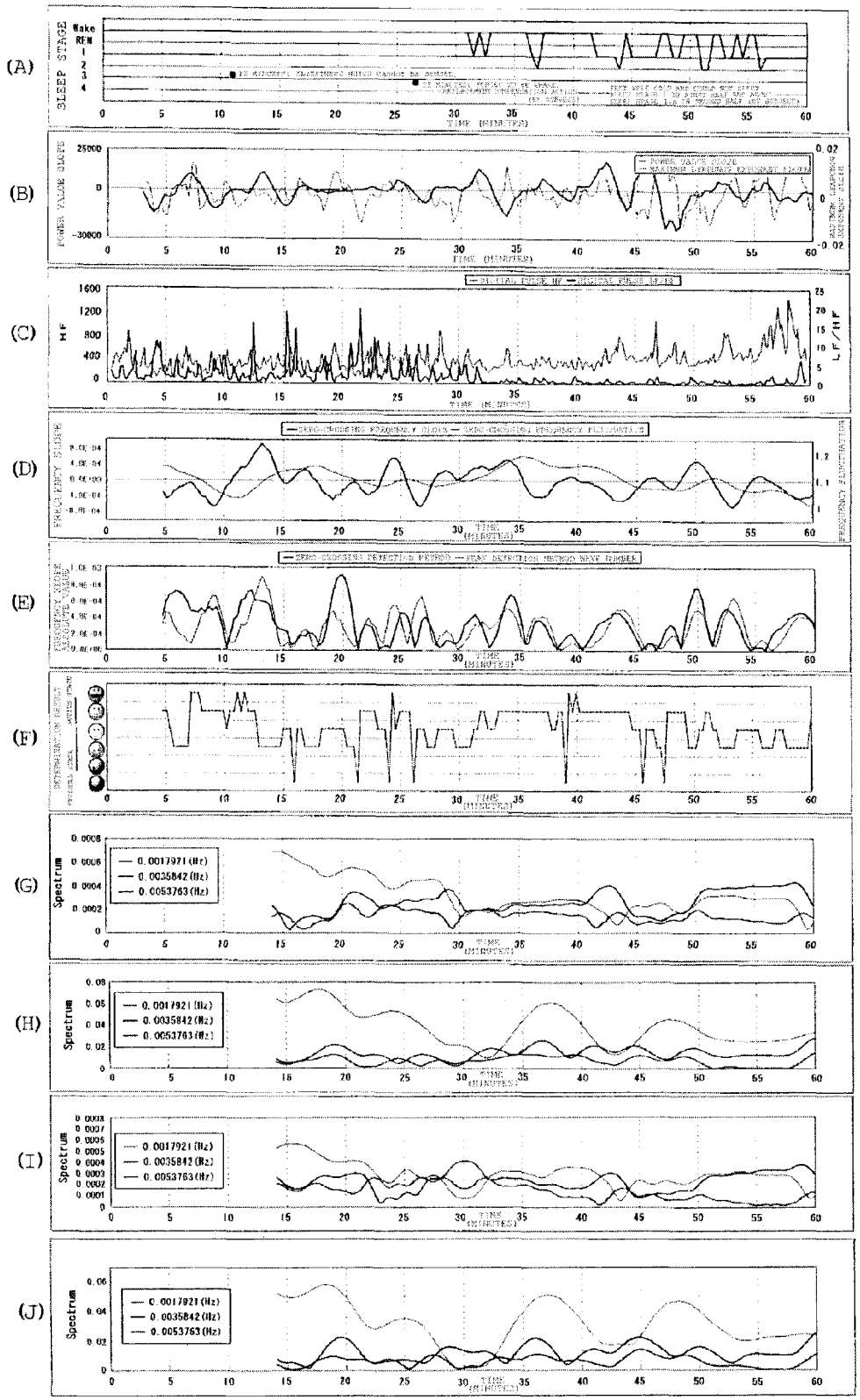
FIGS. 90(A) to 90(J) are diagrams illustrating experiment results of still another subject (male in his 30's) in the sleep introduction experiment A.
Figure 91:
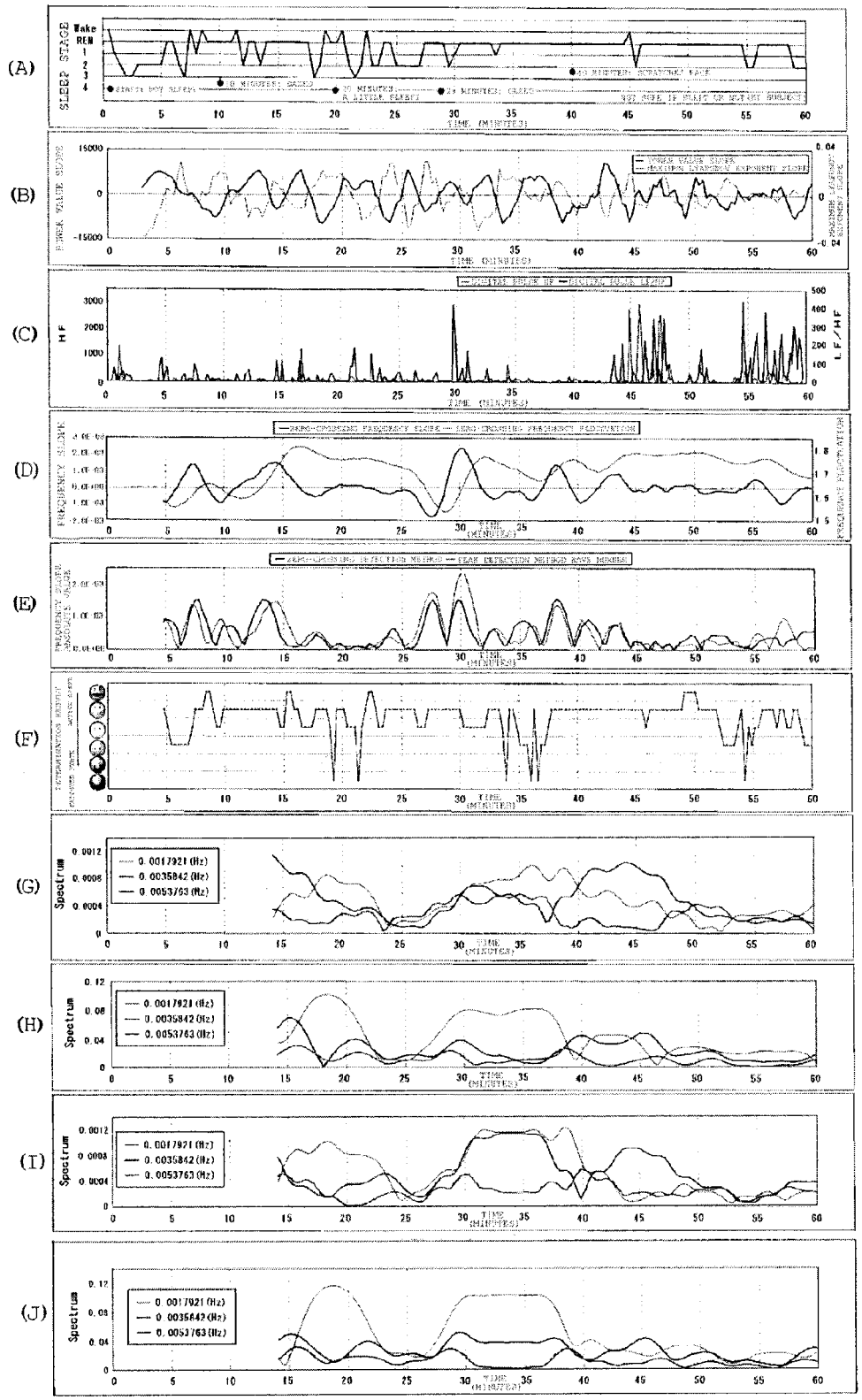
FIGS. 91(A) to 91(J) are diagrams illustrating experiment results of still another subject (male in his 30's) in the sleep introduction experiment A.
Figure 92:
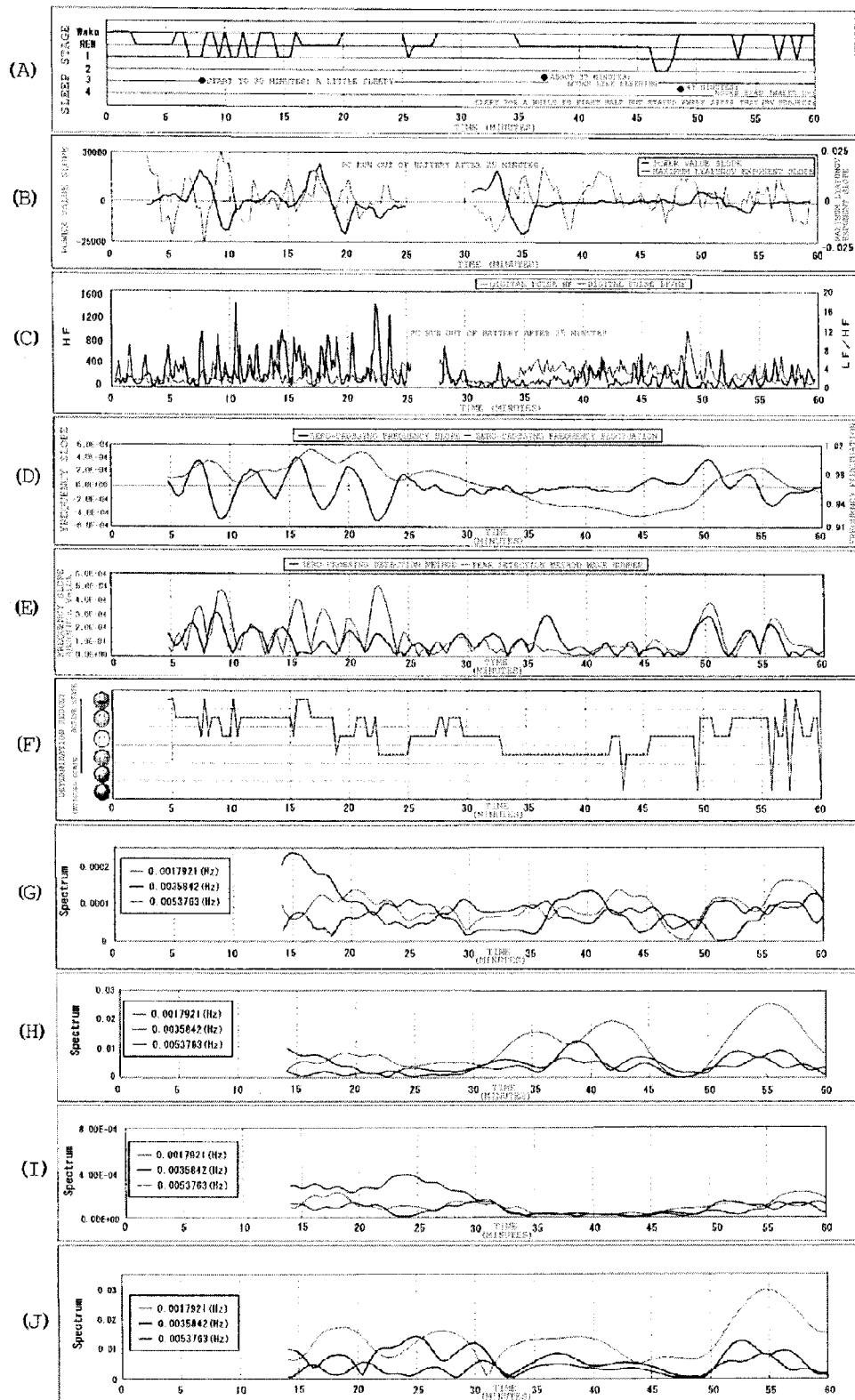
FIGS. 92(A) to 92(J) are diagrams illustrating experiment results of still another subject (male in his 40's) in the sleep introduction experiment A.

If the state is active such as being energetic or resisting against progress of fatigue from the test result which will be described later, the fatigue progresses as time elapses. Thus, the distribution rate of the fatigue reception signal rises gradually or rapidly or changes substantially horizontally with fluctuation (the vicinity of 24 to 31 minutes in FIG. 77(G) is the "sleepiness-related phenomenon emergence period", for example, which will be described later, but the distribution rate of the fatigue reception signal in a time zone prior to that changes substantially horizontally with fluctuation). Then, in the active state, since degrees of influence by control of the brain and the autonomic nerve system are high, the activity adjustment signal changes at a level relatively higher than in the non-active period (sleep transition period or sleep period, for example) (the level of the power spectrum is smaller in the time zone after the sleepiness-related phenomenon emergence period in the vicinity of 24 to 31 minutes in FIG. 77(G) than the time zone before that, for example). On the other hand, the functional adjustment signal changes at a level relatively higher in the non-active period than in the active period (the level of the power spectrum is higher in the time zone of the sleepiness-related phenomenon emergence period (non-active state) in the vicinity of 24 to 31 minutes in FIG. 77(G) than in the time zone in the active state before that, for example. Moreover, at 45 minutes and after, the subject feels that he should not fall asleep but cannot resist the sleepiness and fell asleep).

Among all others, as a characteristic change, the power spectrum of the functional adjustment signal might indicate a time-series change with a rising tendency in a time zone when the fatigue reception signal indicates a time-series change with a lowering tendency (in the vicinity of 24 to 31 minutes in FIG. 77(G), for example), this can be determined to indicate some sign relating to sleepiness of the subject (a sign of a sleep prediction phenomenon emerging before falling asleep, a temporary sleepiness phenomenon (sleepiness awakened in a short time), or a shallow sleep state and the like but these are collectively assumed to be the "sleepiness-related phenomenon emergence period" in this description) from the test result which will be described later.

Figure 73:
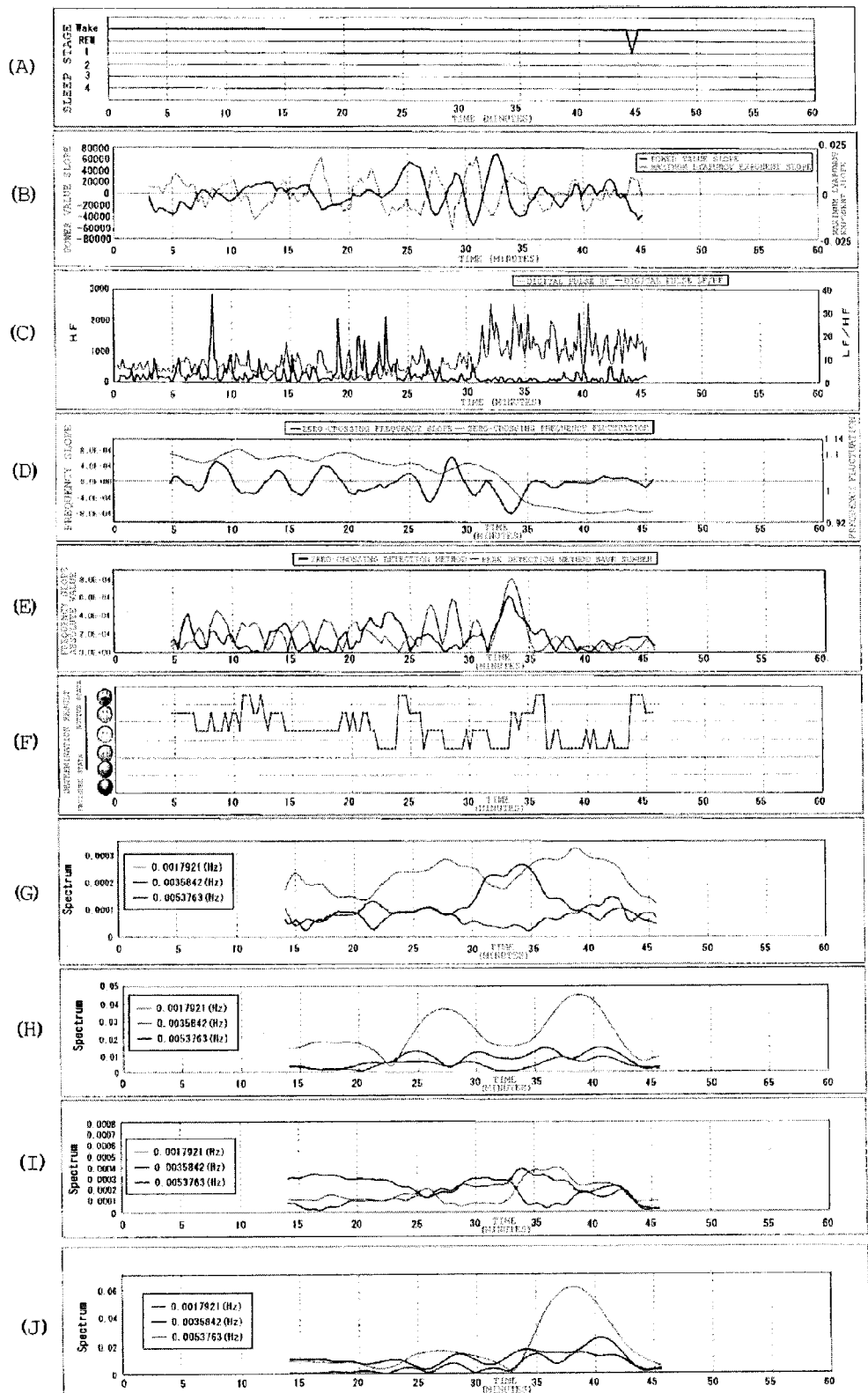
FIGS. 73(A) to 73(J) are diagrams illustrating experiment results of still another subject (male in his 30's) in the sleep introduction experiment A.
Figure 74:
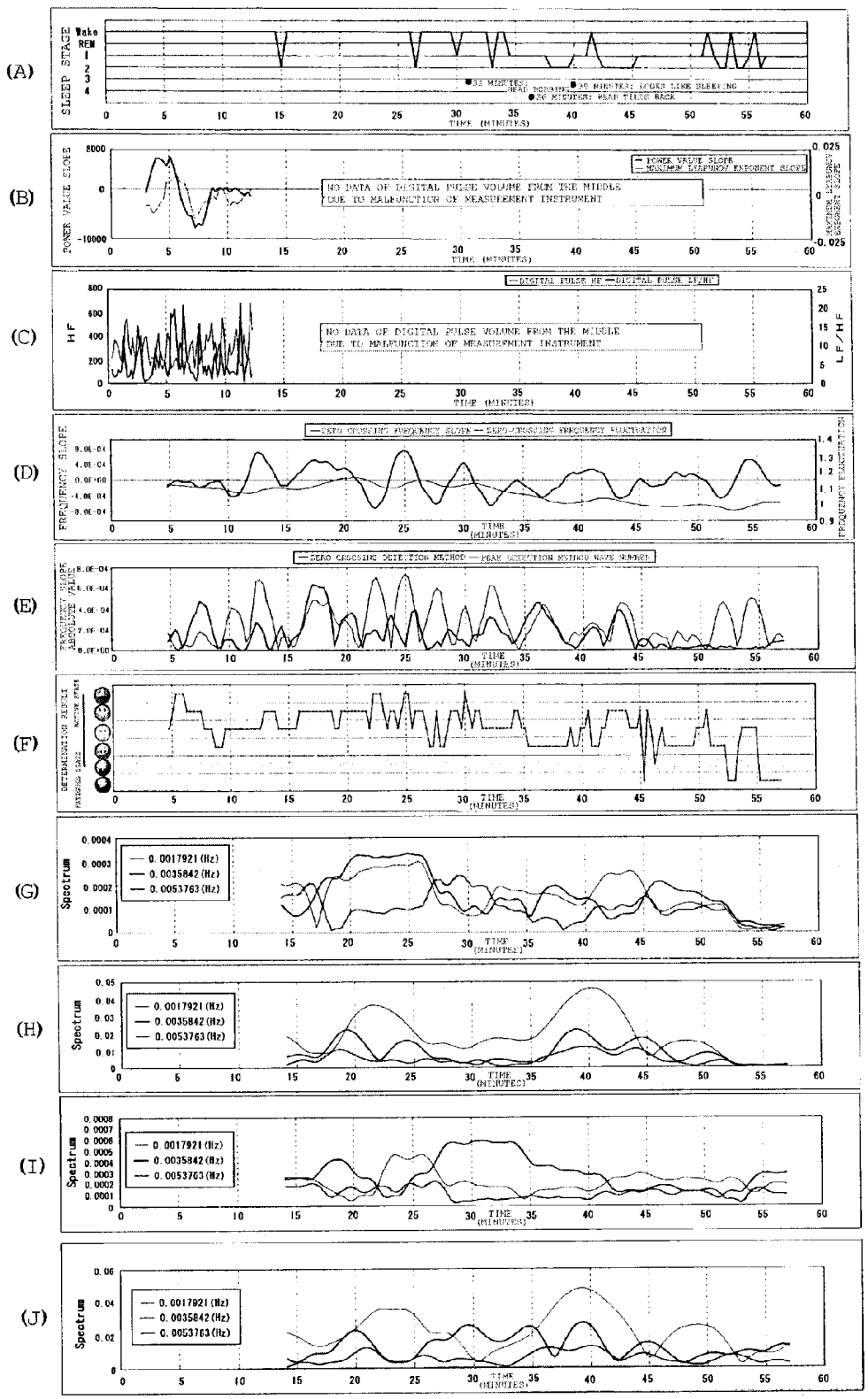
FIGS. 74(A) to 74(J) are diagrams illustrating experiment results of still another subject (male in his 30's) in the sleep introduction experiment A.
Figure 75:
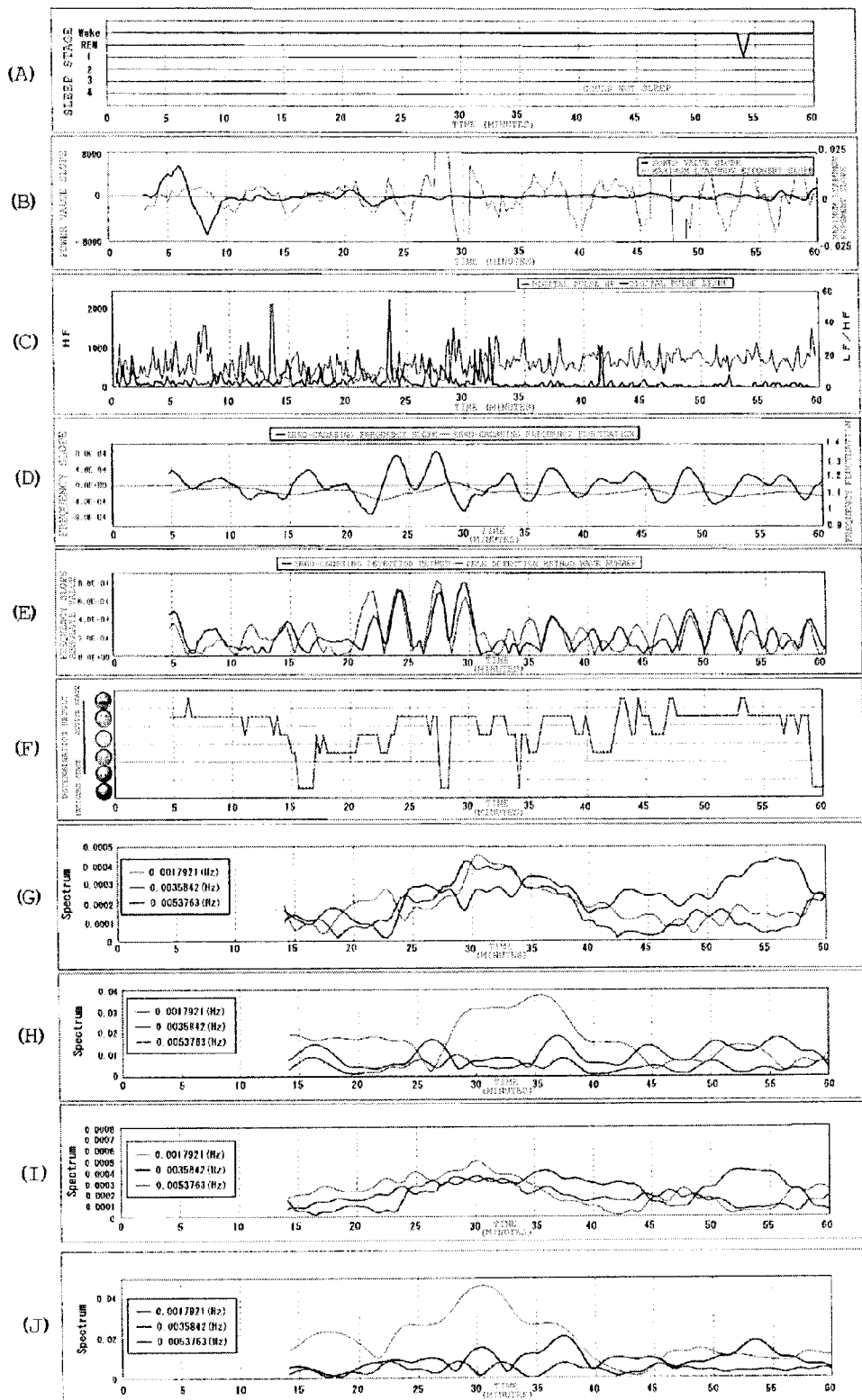
FIGS. 75(A) to 75(J) are diagrams illustrating experiment results of still another subject (male in his 30's) in the sleep introduction experiment A.
Figure 76:
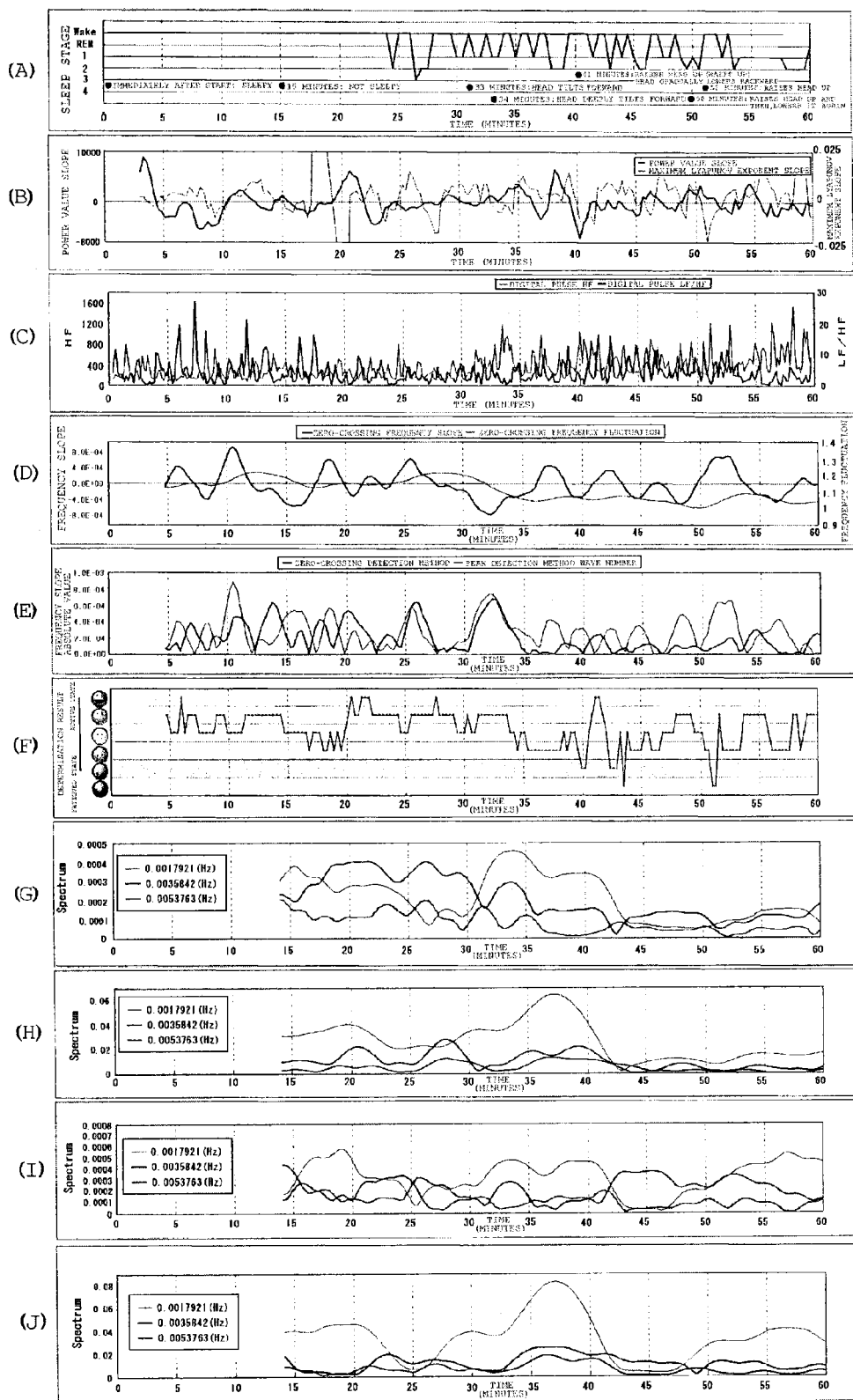
FIGS. 76(A) to 76(J) are diagrams illustrating experiment results of still another subject (male in his 30's) in the sleep introduction experiment A.

Moreover, in the sleepiness-related phenomenon emergence period, the power spectrum of the functional adjustment signal indicates a relatively rising tendency as compared with the fatigue reception signal and the activity adjustment signal, but regarding this tendency, the power spectrum of any of the functional adjustment signals in the frequency slope time-series waveform obtained by the second frequency slope time-series analysis calculating means 640 (hereinafter referred to as a "second frequency slope time-series waveform"), the frequency fluctuation time-series waveform obtained by the first frequency fluctuation time-series analysis calculating means 650 (hereafter referred to as a "first frequency fluctuation time-series waveform"), and the frequency fluctuation time-series waveform obtained by the second frequency fluctuation time-series analysis calculating means 660 (hereinafter referred to as a "second frequency fluctuation time-series waveform") indicates a relatively rising tendency as compared with the fatigue reception signal and the activity adjustment signal in many cases from the test result which will be described later (the sleepiness-related phenomenon emergence period is found in the vicinity of 35 to 40 minutes in FIG. 73(G), for example, and a rising tendency of the functional adjustment signal is found in the second frequency slope time-series waveform, the first frequency fluctuation time-series waveform, and the second frequency fluctuation time-series waveform illustrated in (H) to (J) in that time zone). They indicate increase in the parasympathetic nerve activities, and if each functional adjustment signal increases in the second frequency slope time-series waveform, the first frequency fluctuation time-series waveform, and the second frequency fluctuation time-series waveform in addition to the rise of the power spectrum of the functional adjustment signal in the first frequency slope time-series waveform, the sleepiness-related phenomenon emergence period can be identified more reliably. That is, the larger the number of functional adjustment signals indicating the rising tendency, the higher the reliability of determination on the sleepiness-related phenomenon emergence period becomes. Therefore, it is preferable to check the change in one or more of the functional adjustment signals in the second frequency slope time-series waveform, the first frequency fluctuation time-series waveform, and the second frequency fluctuation time-series waveform in addition to the rise of the power spectrum of the functional adjustment signal in the first frequency slope time-series waveform for determination of the sleepiness-related phenomenon emergence period.

Test Example (Test Contents)

An "experiment in wakeful/active state" and a "sleep introduction experiment" were conducted.

"Experiment in Wakeful/Active State"

The biological signal measuring means 1 illustrated in FIG. 1 is stacked on the back side of the back portion of the product name "Twin lumbar" by Delta Tooling and attached to an automobile seat installed indoors, and biological signals caused by atrial and aortic oscillations (hereinafter referred to as a "heart-part oscillation wave") of randomly chosen 6000 male and female subjects in their 10's to 70's in total in the seated attitude were sampled for 3 days. The measurement time is 1.5 to 30 minutes. For the plate-shaped foam bodies 21 and 22 and the three-dimensional knitted material supporting member 15 constituting the biological signal measuring means 1, a sliced bead foam body having an average diameter of a bead at approximately 5 mm and a thickness of 3 mm was used. For the three-dimensional knitted material 10, the Product number: 49011D by Suminoe Textile Co., Ltd. having a thickness of 10 mm was used. For the film 16, the product number "DUS605-CDR" by Sheedom Co., Ltd. was used.

"Sleep Introduction Experiment"

The sleep introduction experiment was conducted under two types of experimental conditions, that is, A and B. In the both cases, the experiment was conducted by seating the subject on the same automobile seat as that used in the above-described "experiment in wakeful/active state". In the sleep introduction experiment A, in an isolated indoor space without any people, the subjects were required to resist sleepiness and to keep awake for 30 minutes from the start of the experiment. At 30 minutes from the start and after that, each of the subjects was allowed to behave on his/her own will and those who wanted to sleep could sleep and those who wanted to keep awake could keep awake. However, if they fell asleep, they were awakened immediately. The sleep introduction experiment B is a sleep experiment from 9 am to 8 pm during which the subjects could freely fall asleep on their own wills. The subjects of the sleep introduction experiment A were 22 healthy males and females in their 20's to 50's. The subjects of the sleep introduction experiment B were 14 healthy males in their 20's, and not only daytime workers but also nighttime workers were chosen for the subjects in order to examine the influence of circadian rhythm.

In the sleep introduction experiments A and B, prior-art medical indexes, that is, brain waves, electrocardiograms, digital volume pulses were also sampled at the same time with sampling of the heart-part oscillation waves. The brain waves were measured by attaching an electroencephalograph ("EEG-9100, Neurofax µ" by Nihon Kohden Corporation was used in the sleep introduction experiment A, and "FM-515(A)" by Futek Electronics Co., Ltd. was used in the sleep introduction experiment B), and the digital volume pulse were measured by attaching a digital volume pulse meter (finger clip probe SR-5C by AMCO Inc.).

(Check of Characteristic Signal Frequency)

Figure 6:
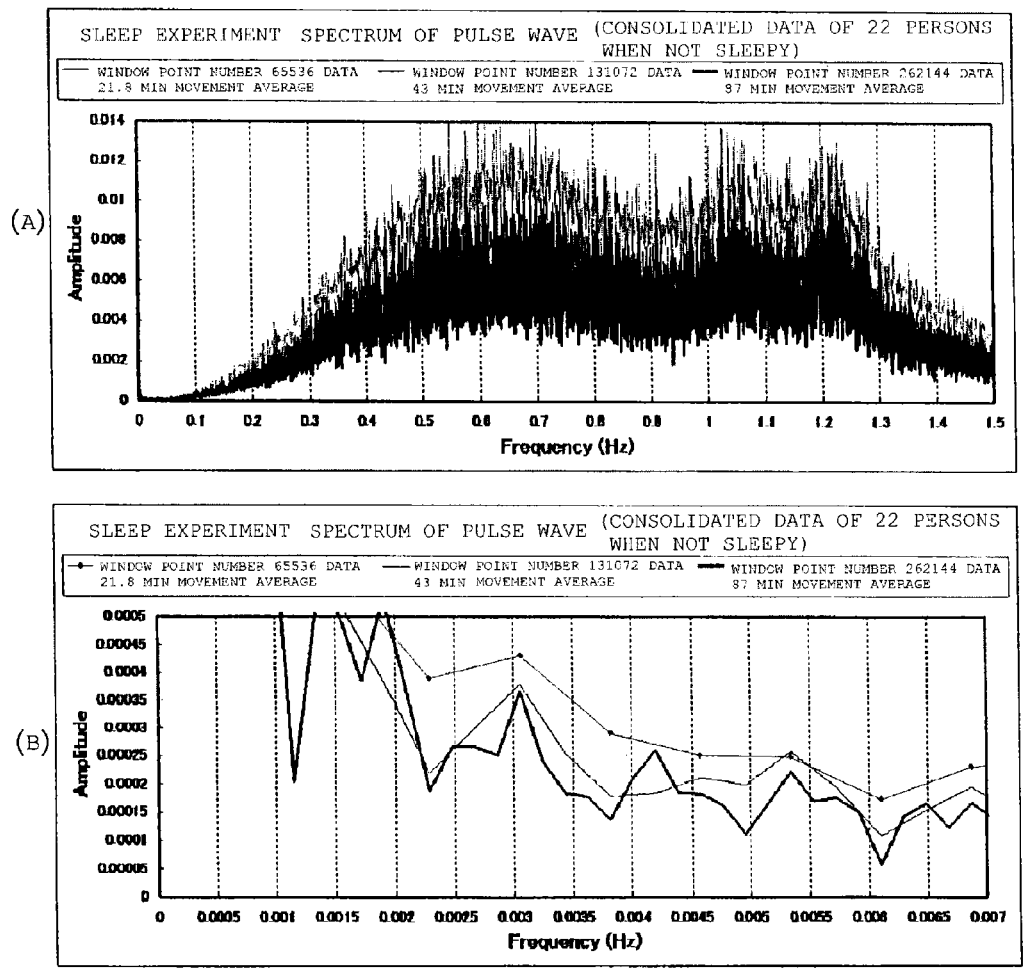
FIGS. 6(A) and 6(B) are diagrams illustrating results of a frequency analysis by consolidating original waveforms of a heart-part oscillation wave in a time zone when there is no sleepiness from data of 22 subjects in a sleep introduction experiment A.
Figure 7:
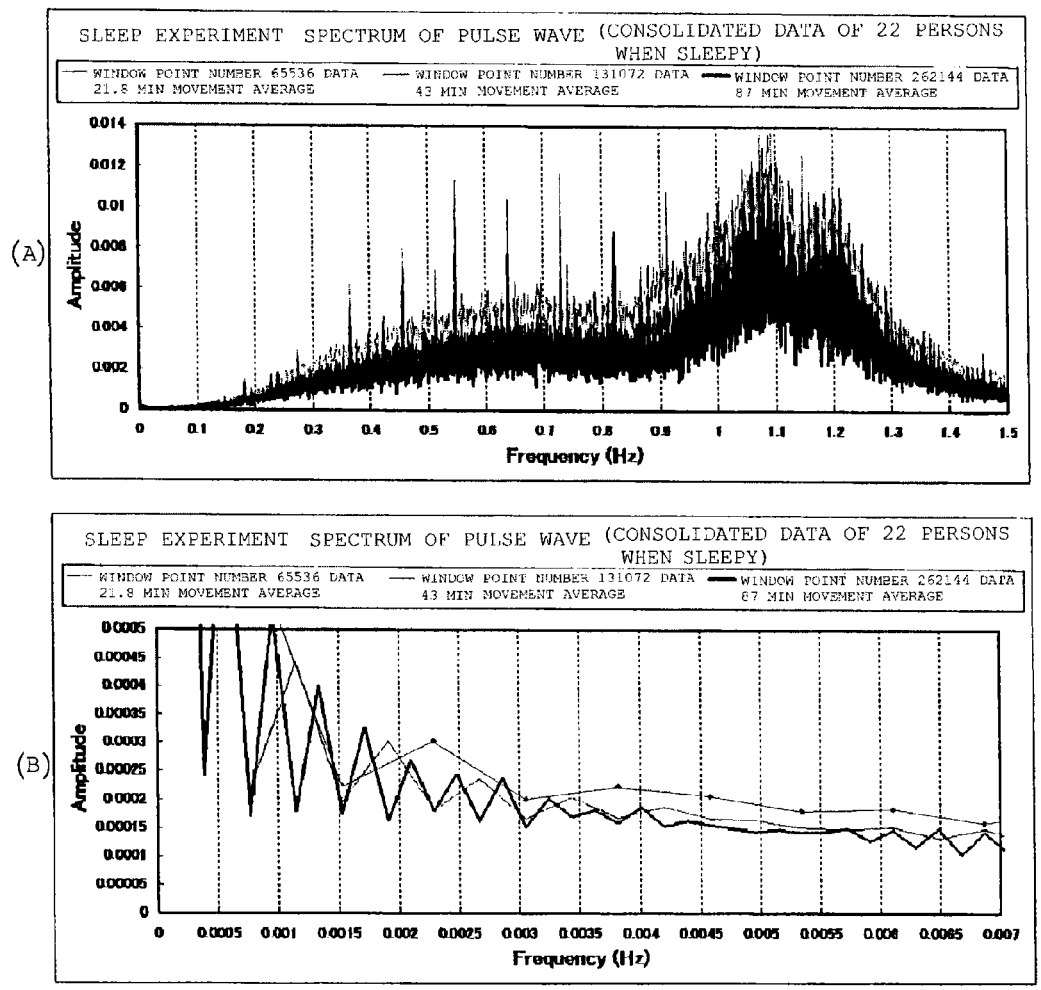
FIGS. 7(A) and 7(B) are diagrams illustrating results of a frequency analysis by consolidating original waveforms of a heart-part oscillation wave in a time zone when sleepiness occurs from data of the 22 subjects in the sleep introduction experiment A.
Figure 8:
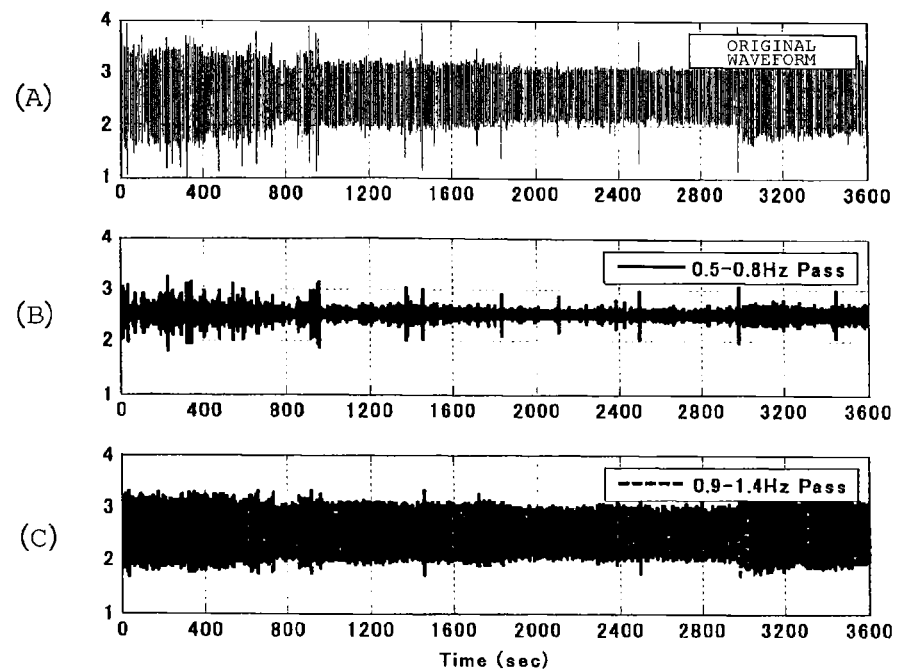
FIGS. 8(A) to 8(D) are diagrams illustrating measurement results over full measurement time of data of one of the 22 subjects in the sleep introduction experiment A.
Figure 8:
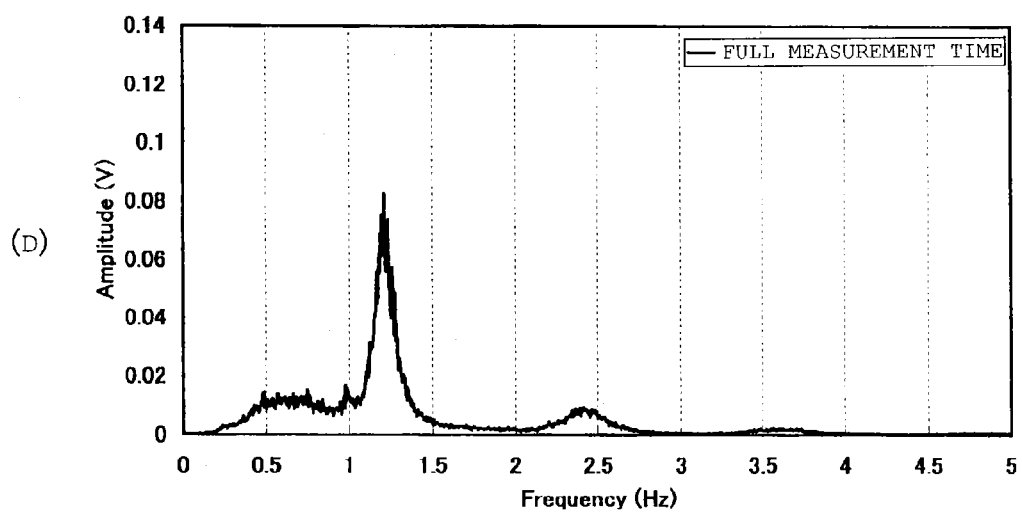
Figure 9:
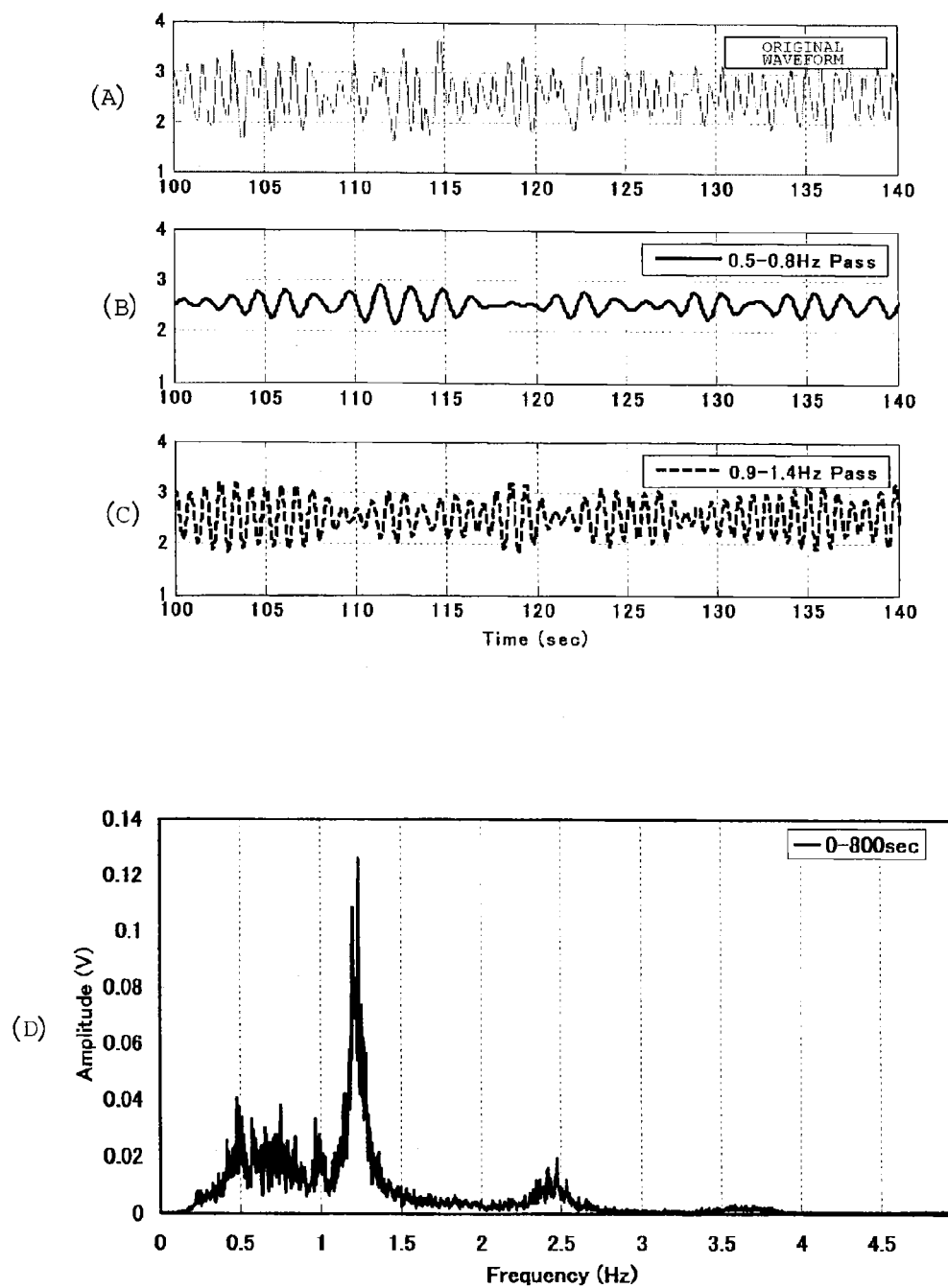
FIGS. 9(A) to 9(D) are diagrams illustrating measurement results from 0 seconds to 800 seconds in FIG. 8.
Figure 10:
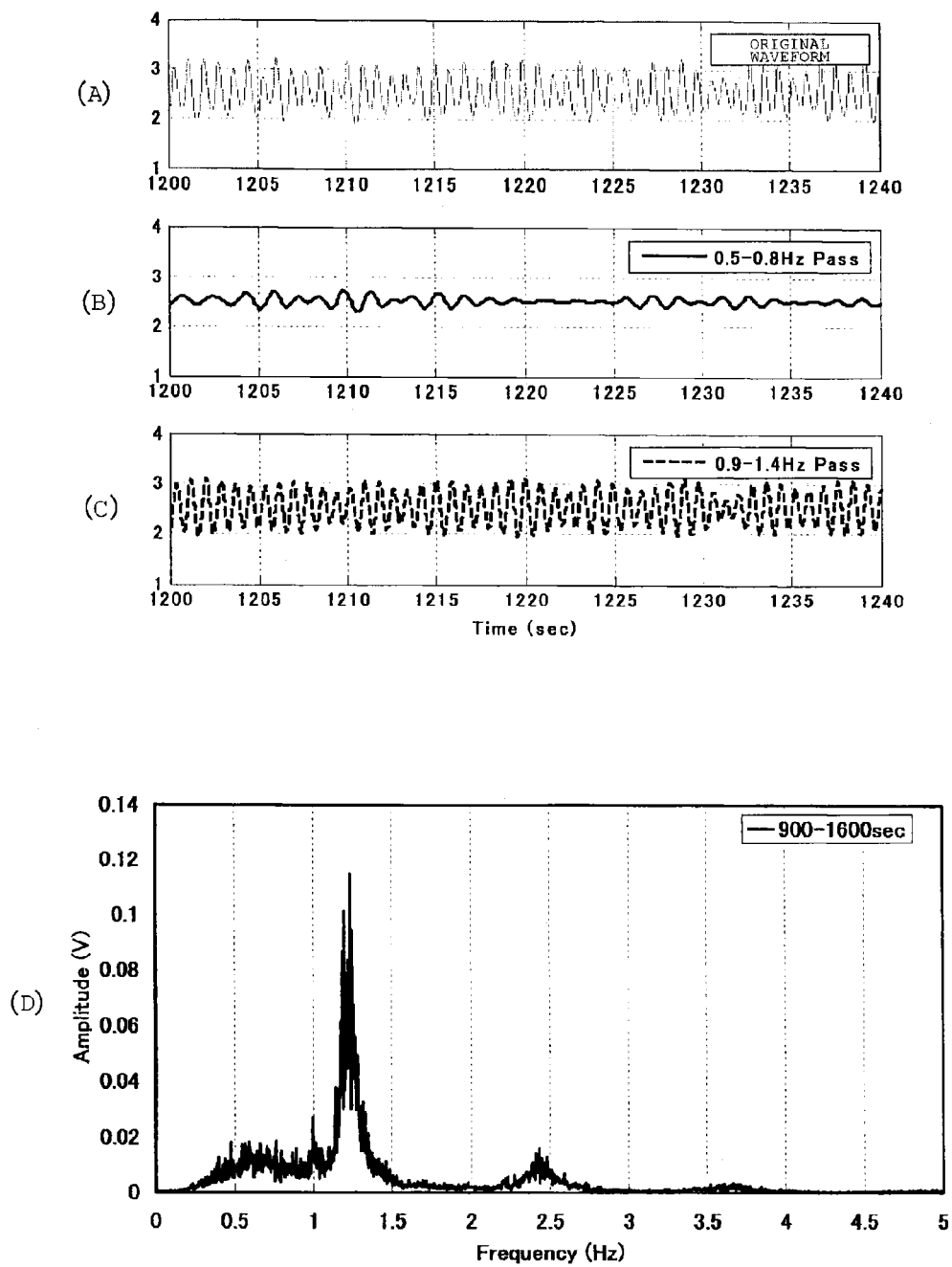
FIGS. 10(A) to 10(D) are diagrams illustrating measurement results from 900 seconds to 1600 seconds in FIG. 8.
Figure 11:
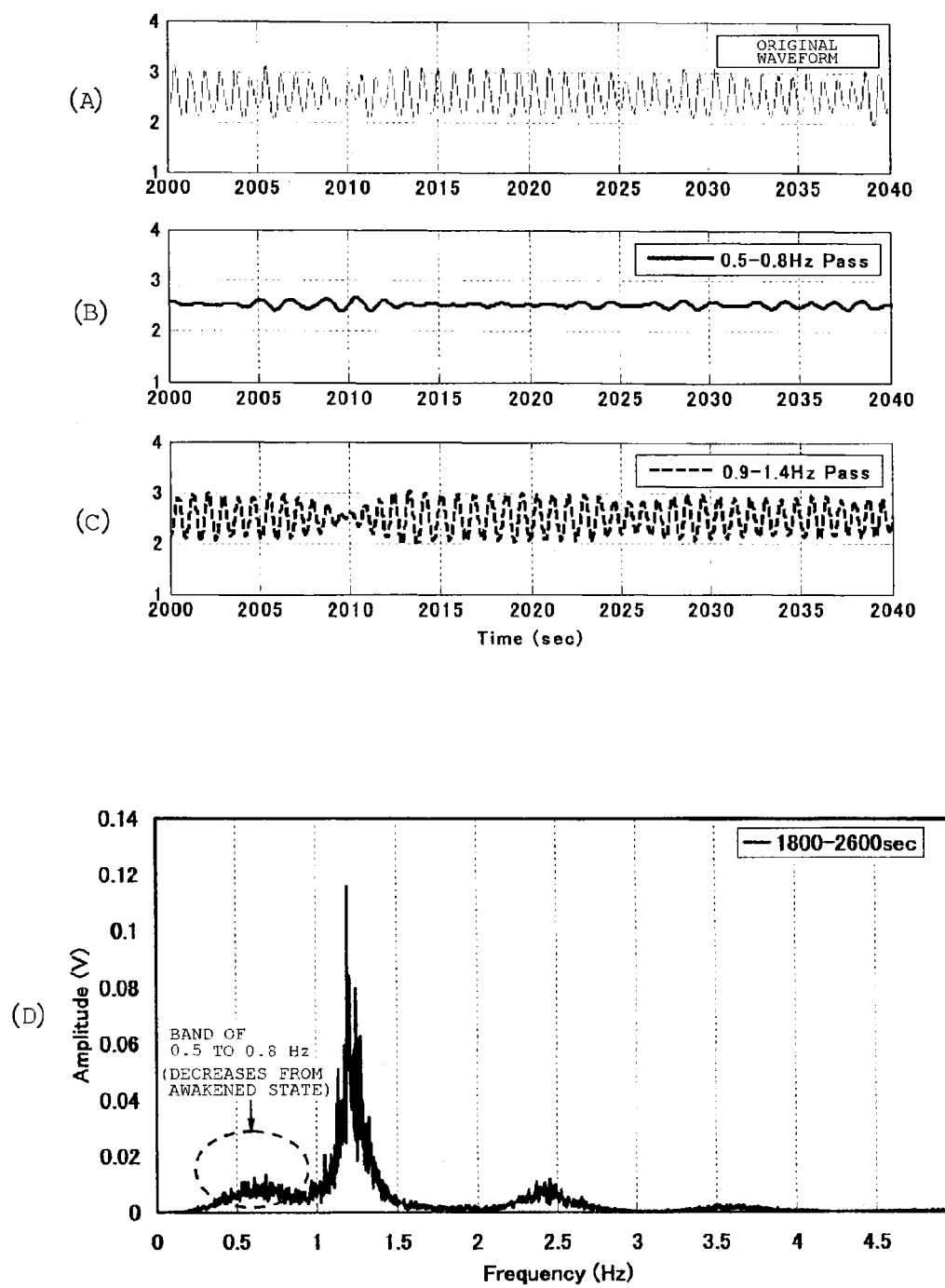
FIGS. 11(A) to 11(D) are diagrams illustrating measurement results from 1800 seconds to 2600 seconds in FIG. 8.

FIG. 6(A) illustrates a frequency analysis result by consolidating original waveforms of the heart-part oscillation waves in a time zone when there was no sleepiness from data of the 22 subjects in the sleep introduction experiment A. In the subjects without sleepiness, a peak was generated at 0.6 to 0.7 Hz, and a peak was generated at 1.0 to 1.3 Hz indicating fluctuation in a heart rate. FIG. 7(A) illustrates a frequency analysis result by consolidating original waveforms of the heart-part oscillation waves in a time zone when sleepiness occurred from data of the 22 subjects in the sleep introduction experiment A. In the subjects with sleepiness, there was no peak at 0.6 to 0.7 Hz, but a peak was generated at 1.0 to 1.3 Hz indicating fluctuation in a heart rate. From the above-described experiment results, the heart-part oscillation waves in the time zone in a wakeful state (time zone without sleepiness) generated fluctuation in a frequency band of approximately ½ of the heart-rate fluctuation (1.0 to 1.3 Hz). On the other hand, there was no fluctuation in this band in the time zone with sleepiness. This is recognized only as a small difference on the original waveforms and is difficult to be distinguished. Thus, the area at 0.007 Hz or less in FIG. 6(A) and FIG. 7(A) are enlarged in FIG. 6(B) and FIG. 7(B). From comparison between FIG. 6(B) and FIG. 7(B), it was found that the fluctuation occurring at 0.6 to 0.7 Hz in FIG. 6(A) generated fluctuations at 0.0015 Hz, 0.002 Hz, 0.003 Hz, 0.0042 Hz, and 0.0053 Hz illustrated in FIG. 6(B). The above-described program set on the biological body state estimation device 60 of this embodiment is to have this fluctuation in the ultra or super low frequency area emerge, and by applying this analysis method, the sleepiness-related phenomena such as presence of sleepiness and a sleep prediction phenomenon can be identified.

Figure 12:
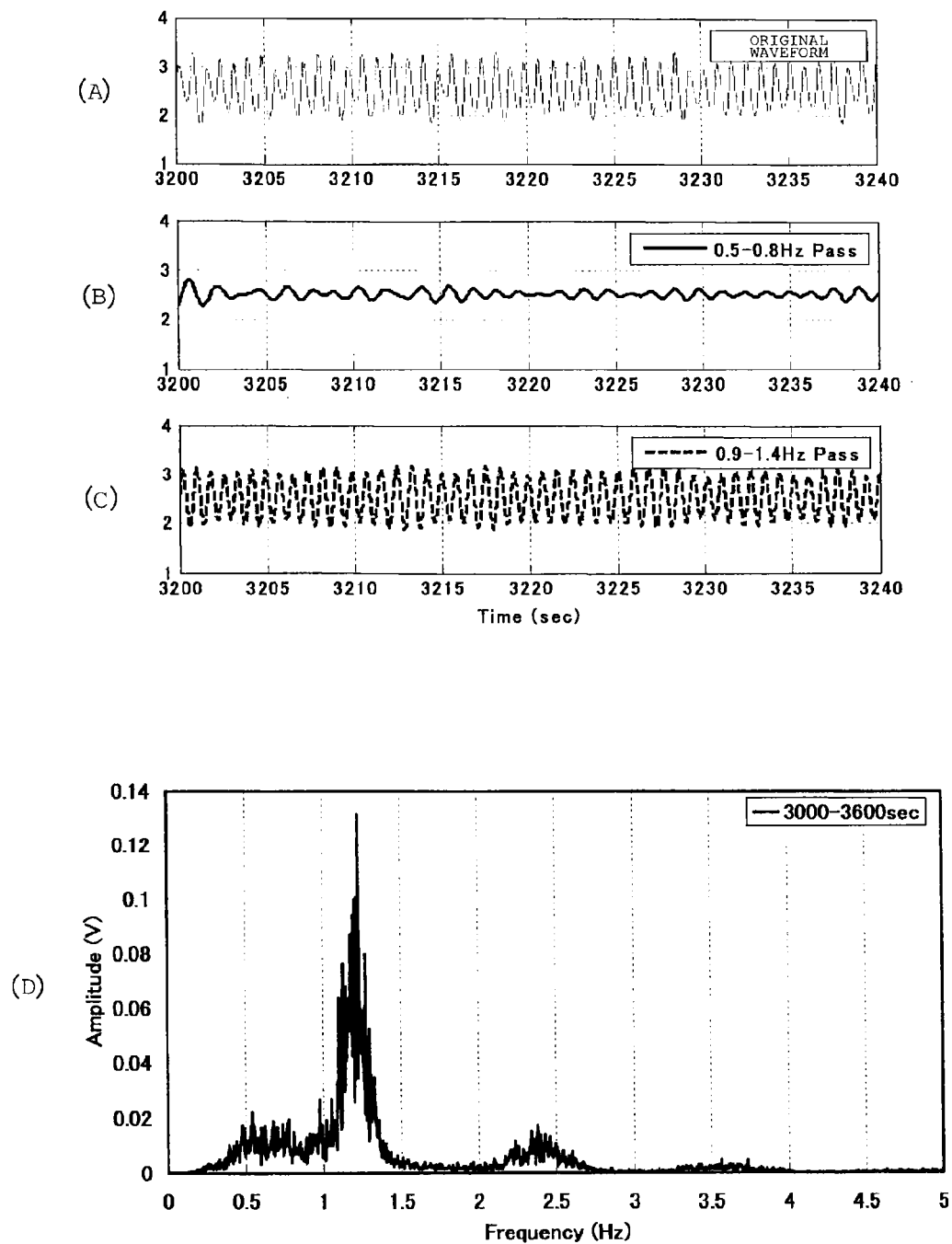
FIGS. 12(A) to 12(D) are diagrams illustrating measurement results from 3000 seconds to 3600 seconds in FIG. 8.

FIGS. 8 to 12 illustrate data of one of the 22 subjects in the sleep introduction experiment A. This subject easily develops abnormal cardiac rhythm by constitution. The subject maintained the wakeful state from 0 to 800 seconds illustrated in FIG. 9 and was resisting sleepiness from 900 to 1600 seconds illustrated in FIG. 10. During the period from 1800 to 2600 seconds illustrated in FIG. 11, the subject fell asleep at ease under the instruction "you may sleep" and was in a state changed from S1 to S2 in terms of the sleep stage. The period from 3000 to 3600 seconds illustrated in FIG. 12 is the S1 state. The pulse original waveform frequency analysis result in the sleep introduction experiment A (full measurement result (FIG. 8)) has a primary peak at 0.5 to 0.8 Hz, and a secondary large peak emerged at 1.2 Hz. The former indicates a frequency band of fluctuation, while the latter indicates a frequency of heart-rate fluctuation. This recreates the state illustrated in FIG. 6. Fluctuation occurred between 0.5 Hz and 0.8 Hz in the wakeful state from 0 to 800 seconds. The frequency of the heart-rate fluctuation is 1.2 Hz. In the time-series waveforms in FIGS. 8 to 10, (A) illustrates the original waveform of the heart-part oscillation waves, (B) illustrates the waveform of fluctuation from 0.5 Hz to 0.8 Hz, and the waveform in (C) illustrates the heart-rate fluctuation of 1.2 Hz. That is, the heart-part oscillation waves are considered to be a sum of the heart-rate fluctuation of 1.2 Hz and a waveform created by the atrial and aortic oscillations from 0.5 Hz to 0.8 Hz. By examining each frequency analysis result illustrated in (D) of FIGS. 9 to 12, in comparison of the waveforms of the fluctuation from 0.5 Hz to 0.8 Hz, the fluctuation waveform in the wakeful state illustrated in FIG. 9(B) shows the largest power value, and the power value lowers as the sleep depth progresses. This state appears as the magnitude of the power spectrum from 0.5 Hz to 0.8 Hz of the frequency analysis results. Regarding the heart-rate fluctuation, periodic fluctuation occurred in the wakeful state, and the fluctuation becomes smaller as the sleep gets deeper. In a state corresponding to a daytime nap, no change is found both in the frequency and the power value in the state change from wakefulness to sleep. The same tendency appears also in the heart-part oscillation waves. However, if the sleep becomes deep, the power value lowers by approximately 30% with the decrease of fluctuation.

Figure 13:
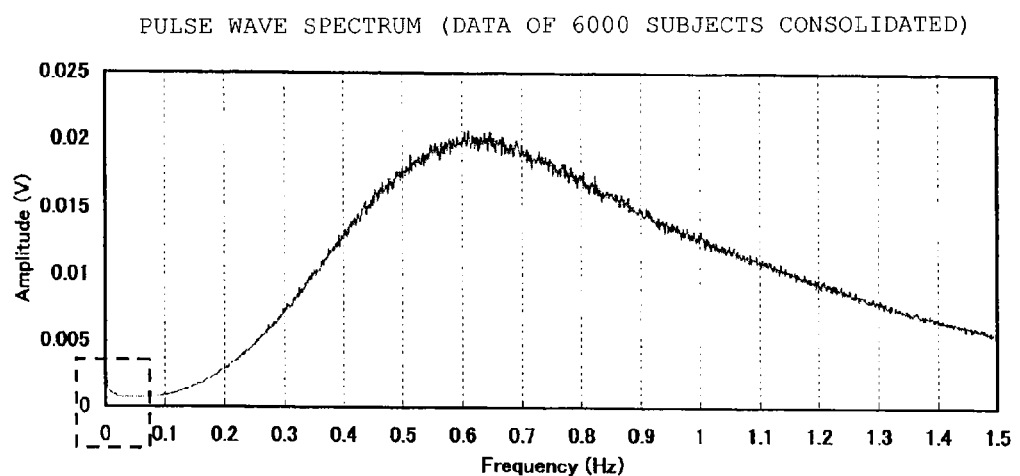
FIG. 13 is a diagram illustrating a frequency analysis result of a waveform obtained by consolidating the heart portion swinging wave of 6000 subjects in an "experiment in wakeful/active state".
Figure 14:
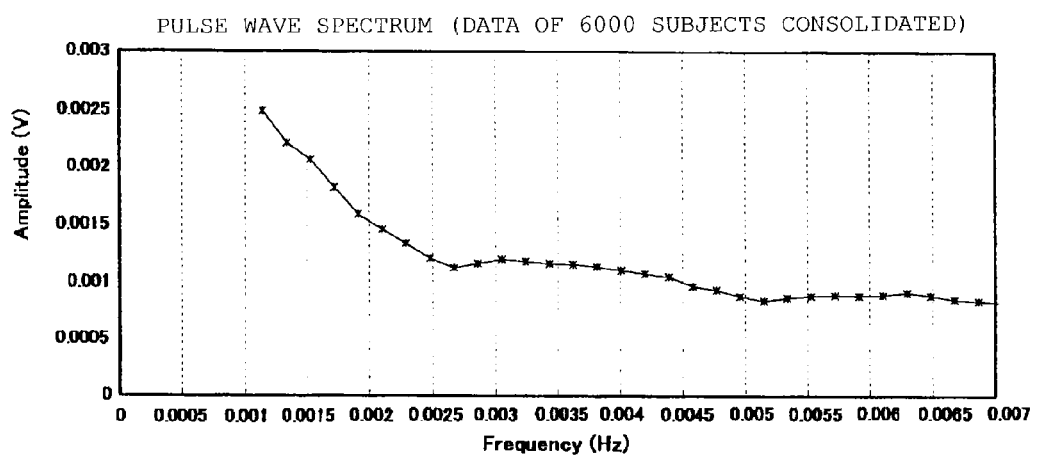
FIG. 14 is a diagram illustrating a region surrounded by a broken line at 0.1 Hz or less in FIG. 13 in an enlarged manner.

On the other hand, FIG. 13 illustrates a frequency analysis result of the waveform obtained by consolidating the heart-part oscillation waves of 6000 subjects in the "experiment in wakeful/active state". From this frequency analysis, it can be understood that the frequency band sampled as the heart-part oscillation wave concentrates to the vicinity of 0.3 to 1.5 Hz in an area not more than 1.5 Hz. These frequency analysis results are considered to capture the fluctuation waveforms and the heart-rate fluctuation illustrated in FIG. 6. That is, it is also suggested here, that there is a fluctuation waveform corresponding to ½ of the heart-rate fluctuation in the people in the wakeful state or in the active state. Then, in order to capture this fluctuation waveform, the ultra or super low frequency component was verified as illustrated in FIG. 14. As a result, it was suggested that there is a fluctuation component involved in respiration and the cardiac/circulatory vibrations in the vicinity of 0.3 to 1.5 Hz at 0.0015 Hz or less, 0.0015 to 0.0027 Hz, 0.0027 to 0.0052 Hz, and 0.0052 to 0.007 Hz.

Figure 15:
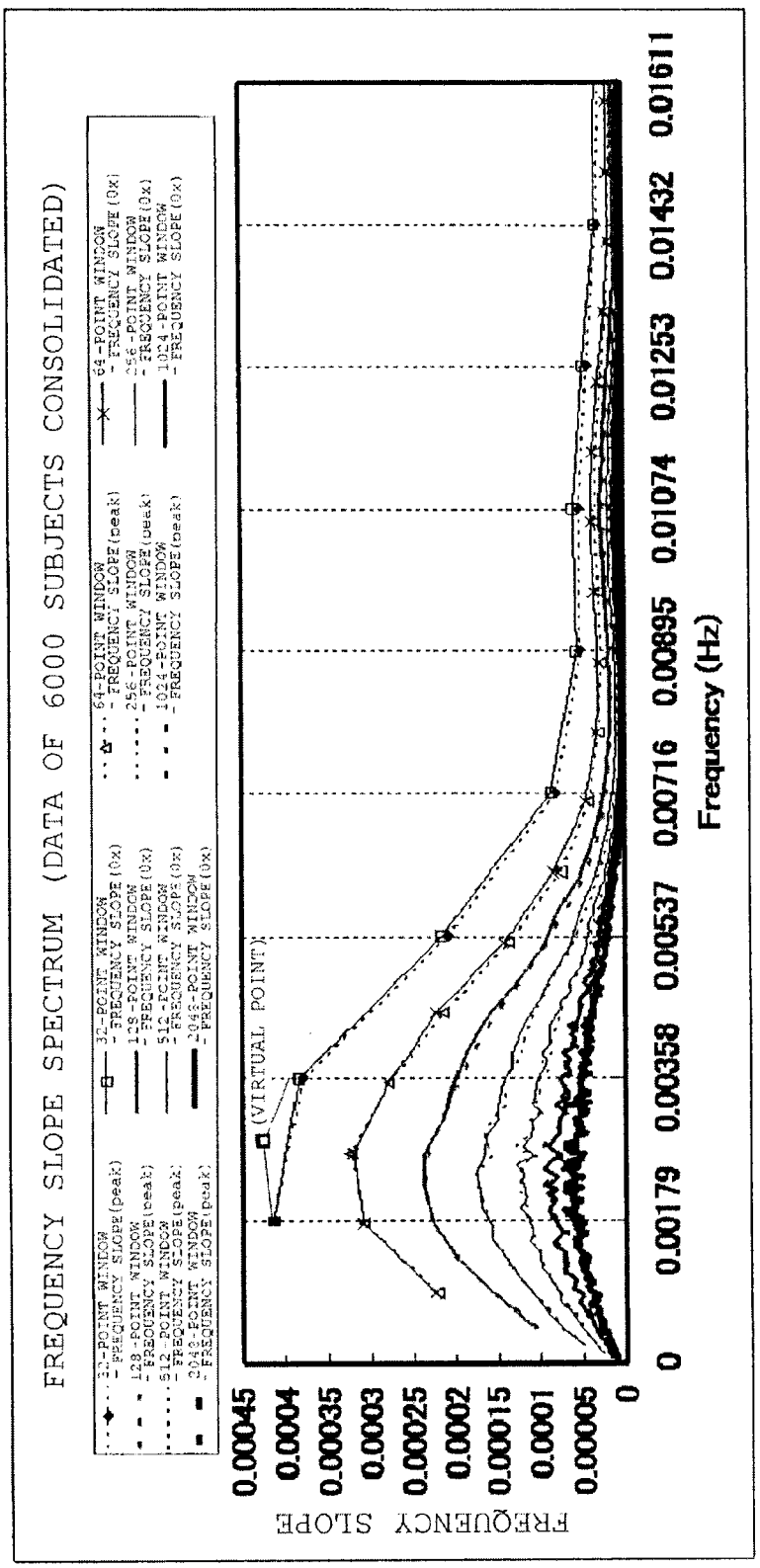
FIG. 15 is a diagram illustrating a frequency analysis result using frequency slope time-series waveforms of data obtained by consolidating the heart-part oscillation waves of 6000 subjects.

FIG. 15 illustrates a result of the frequency analysis by means of the power spectrum calculating means 670 by using the first frequency slope time-series waveform using the zero-crossing (0×) method and a result of the frequency analysis by means of the power spectrum calculating means 670 by using the second frequency slope time-series waveform using the peak detection method for the data obtained by consolidating the heart-part oscillation waves of 6000 subjects. A window for the frequency analysis is changed from 32 points to 2048 points, and a level of the power spectrum according to resolution performance differences is observed.

Figure 16:
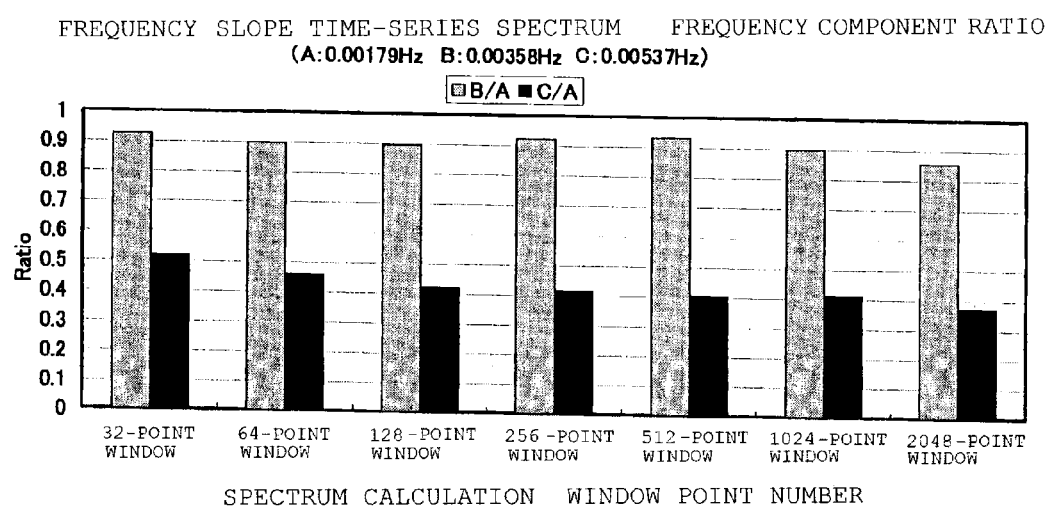
FIG. 16 is a diagram illustrating a frequency component ratio of a power spectrum of the frequency slope time-series waveform.

Here, in order to identify a frequency found to be effective for state estimation, the standard frequency is assumed to be at 0.00179 Hz, 0.00358 Hz, and 0.00537 Hz. This is because, as described above, it is suggested that there is a frequency band involved in respiration and cardiac and circulatory vibrations from 0.0015 to 0.0027 Hz, 0.0027 to 0.0052 Hz, and 0.0052 to 0.007 Hz and also because 0.00179 Hz, 0.00358 Hz, and 0.00537 Hz belong to these ranges, respectively, among the numerical values on the equally divided lateral axis in FIG. 15. FIG. 16 illustrates a frequency component ratio of the power spectrums at 0.00179 Hz, 0.00358 Hz, and 0.00537 Hz of the frequency slope time-series waveform. Here, tendencies caused by the resolution performance difference of the frequency analysis of the frequency slope time-series waveform and the frequency fluctuation time-series waveform are also indicated. From the results of the frequency component ratio, it is understood that the resolution has little influence on the frequency characteristic difference but affects the difference in the power spectrum. And the effectiveness of 0.00179 Hz, 0.00358 Hz, and 0.00537 Hz set as the standard frequencies in order to capture the characteristics of the frequency analysis is suggested. These standard frequencies are present within the ranges from 0.0015 to 0.0027 Hz, 0.0027 to 0.0052 Hz, and 0.0052 to 0.007 Hz of the ultra or super low frequency band which might be involved in respiration and cardiac/circulatory vibrations illustrated in FIG. 14.

Figure 17:
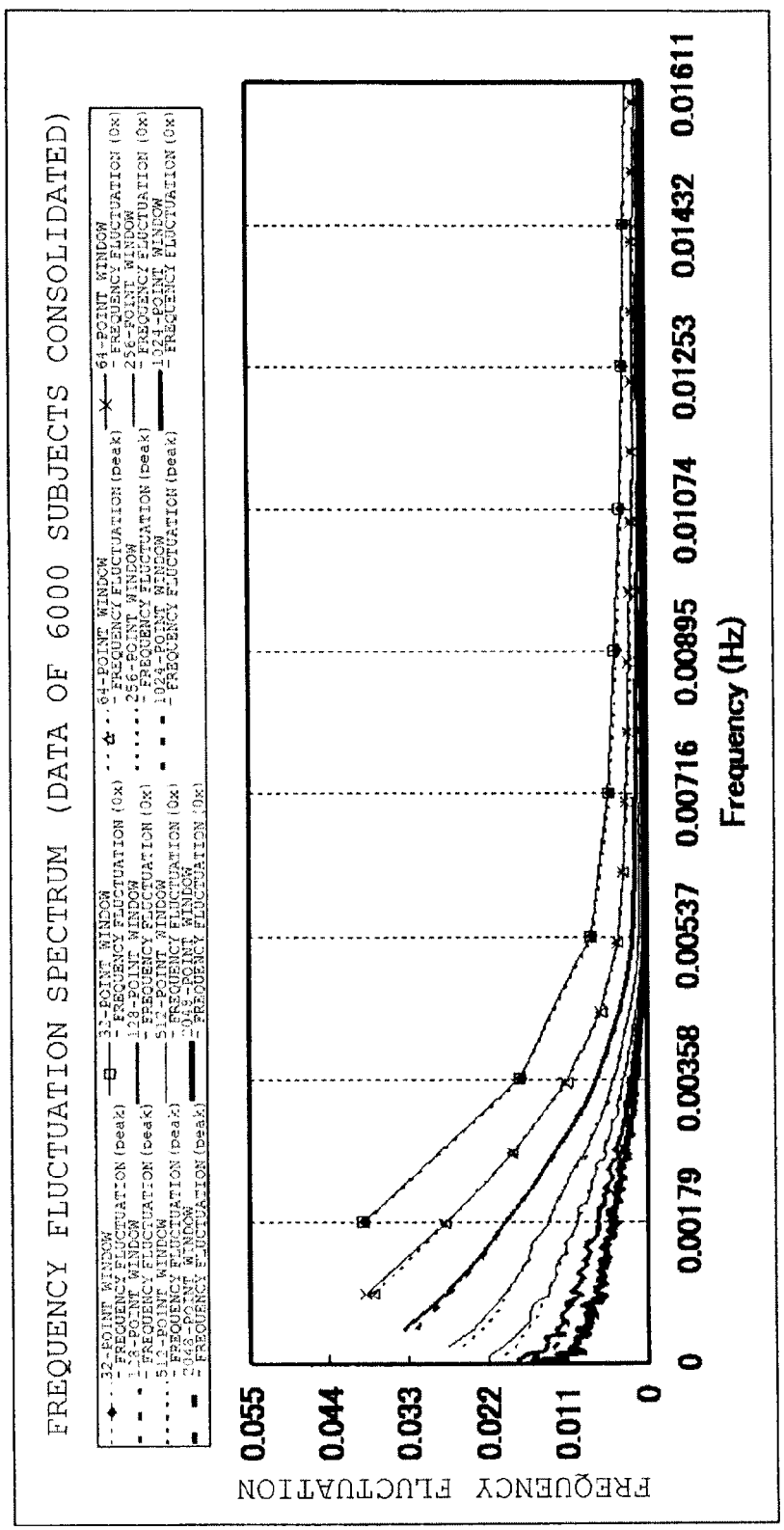
FIG. 17 is a diagram illustrating the frequency analysis result using a frequency fluctuation time-series waveform.

Here, FIG. 17 illustrates a result of the frequency analysis acquired by the power spectrum calculating means 670 by using the first frequency fluctuation time-series waveform using the zero-crossing (0×) method and a result of the frequency analysis by means of the power spectrum calculating means 670 by using the second frequency fluctuation time-series waveform using the peak detection method. These frequency analysis results of the frequency fluctuation suggest that the fluctuation involved in the frequency fluctuation might be present at 0.00537 Hz or less in the ultra or super low frequency band.

Figure 18:
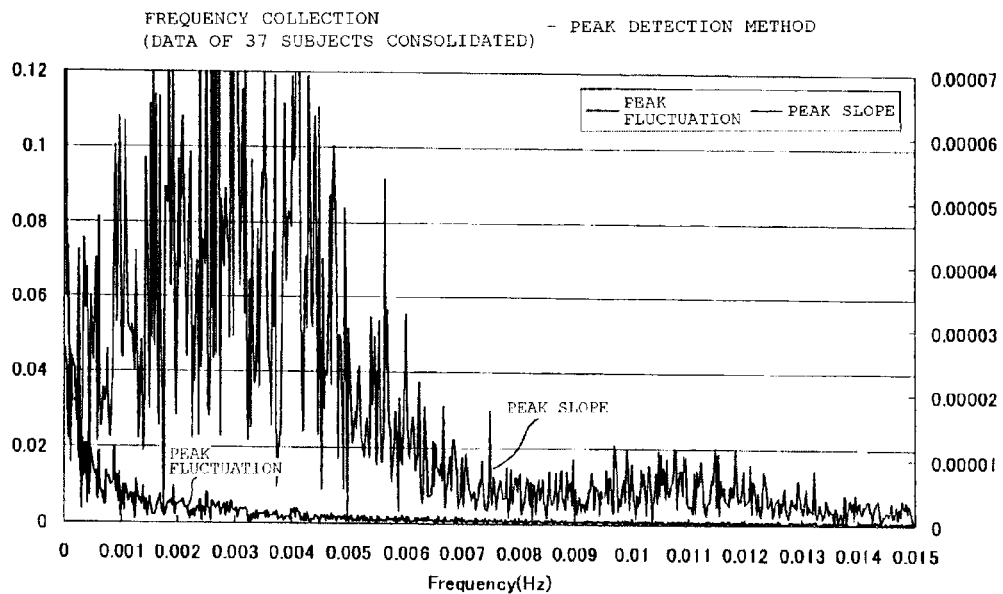
FIG. 18 is a diagram illustrating the frequency analysis result of the frequency slope time-series waveform and the frequency fluctuation time-series waveform by means of a peak detection method using data of 37 subjects in the 6000 subjects.
Figure 19:
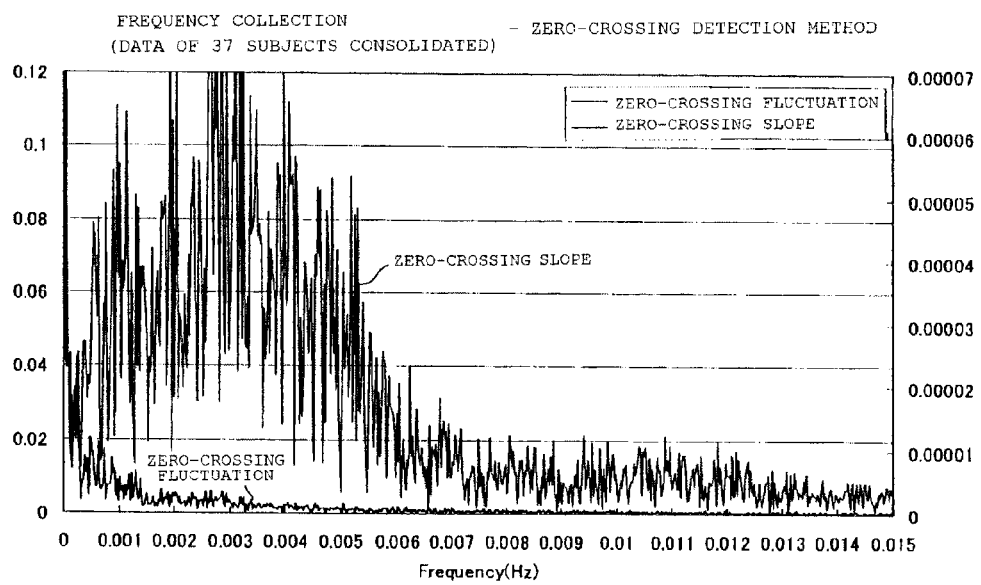
FIG. 19 is a diagram illustrating the frequency analysis result of the frequency slope time-series waveform and the frequency fluctuation time-series waveform by means of a zero-crossing method using data of the 37 subjects in the 6000 subjects.

FIGS. 18 and 19 illustrates the time-series waveforms configured by randomly extracting and consolidating heart-part oscillation waves subjected to the frequency analysis of 37 subjects among the 6000 subjects in their 10's to 70's. Here, from the frequency analysis results, the frequency slope time-series waveform of the heart-part oscillation waves of the people in the wakeful/active state have large fluctuations in the power spectrum at 0.007 Hz or less both in the zero-crossing method and the peak detection method. Moreover, the frequency analysis results of the frequency fluctuation time-series waveform of the heart-part oscillation waves of the people in the wakeful/active state also have marked fluctuations in the power spectrum at 0.0055 Hz or less both in the zero-crossing method and the peak detection method.

Figure 20:
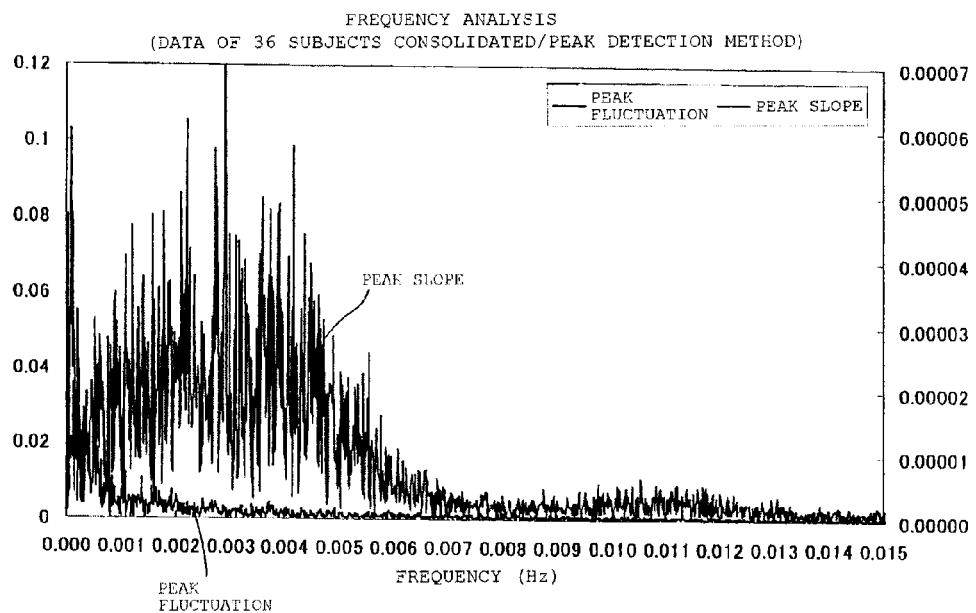
FIG. 20 is a diagram illustrating the frequency analysis result of the frequency slope time-series waveform and the frequency fluctuation time-series waveform by means of the peak detection method using data of 36 subjects in a sleep introduction experiment.
Figure 21:
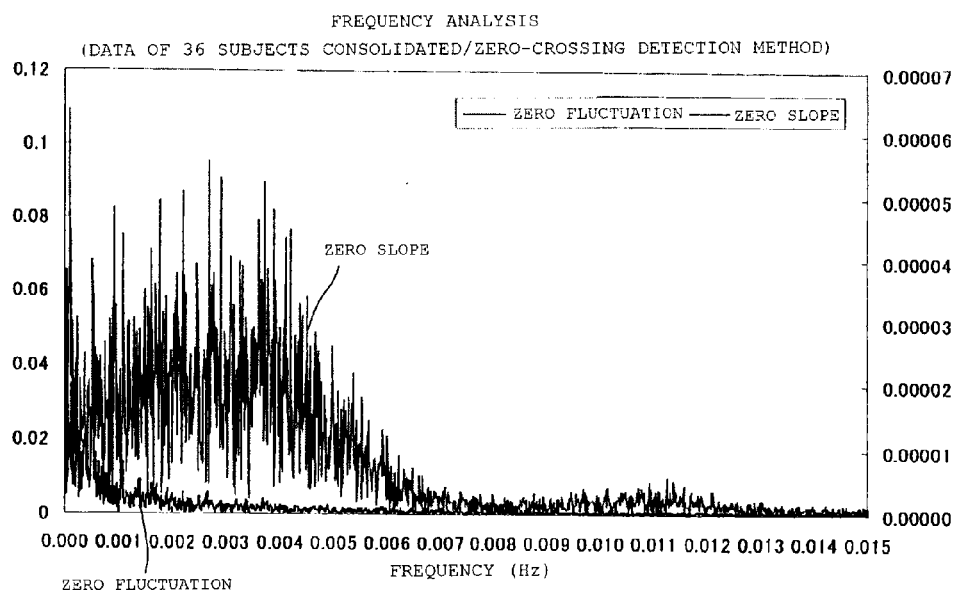
FIG. 21 is a diagram illustrating the frequency analysis result of the frequency slope time-series waveform and the frequency fluctuation time-series waveform by means of the zero-crossing method using data of 36 subjects in the sleep introduction experiment.

Subsequently, analysis results of the heart-part oscillation waves of 36 subjects in the sleep introduction experiments A and B analyzed similarly are illustrated in FIGS. 20 and 21. The frequency analysis results of the frequency slope time-series waveform of the heart-part oscillation waves of the subjects of the sleep introduction experiments have fluctuation in the power spectrum at 0.007 Hz or less similarly to those in the wakeful/active state, but the magnitude of the power spectrum is reduced to half. On the other hand, in the frequency analysis result of the frequency fluctuation time-series waveform of the heart-part oscillation waves of the subjects in the sleep introduction experiments, a portion with a large fluctuation in the power spectrum is shifted to the low frequency side, and the power spectrum itself is decreased by 30%.

From the above-described experiment/analysis results, the frequency component range in which fluctuation occurs on the heart-part oscillation fluctuation can be identified as 0.007 Hz or less.

Subsequently, the data of the 37 subjects in the wakeful/active state illustrated in FIGS. 18 and 19 are illustrated not in consolidation but individually.

Figure 22:
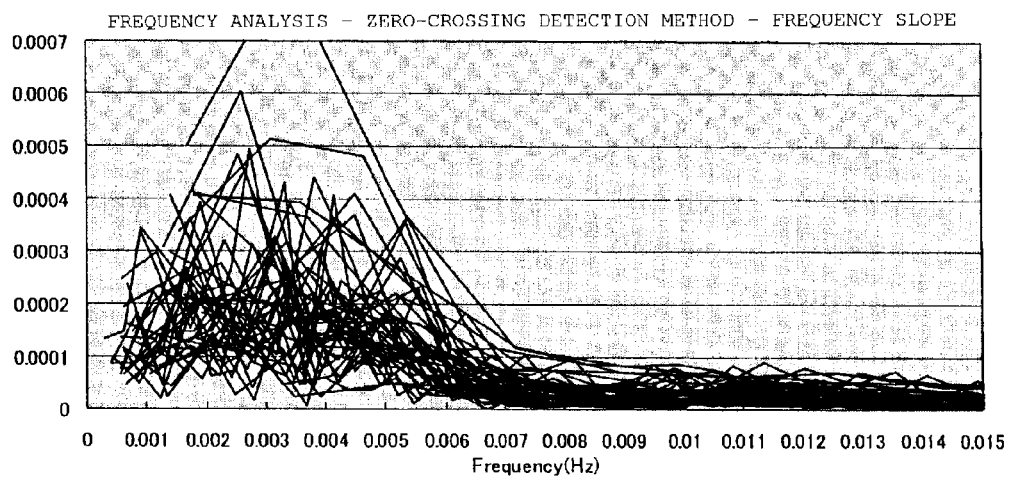
FIG. 22 is a diagram illustrating the frequency analysis result of the frequency slope time-series waveform by means of the zero-crossing method of the heart-part oscillation wave of a person in a wakeful/active state.
Figure 23:
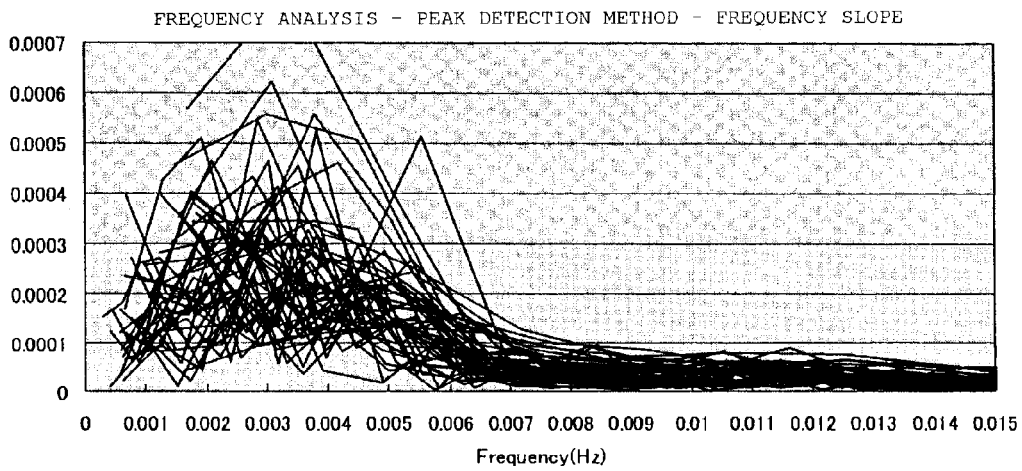
FIG. 23 is a diagram illustrating the frequency analysis result of the frequency slope time-series waveform by means of the peak detection method of the heart-part oscillation wave of a person in a wakeful/active state.
Figure 24:
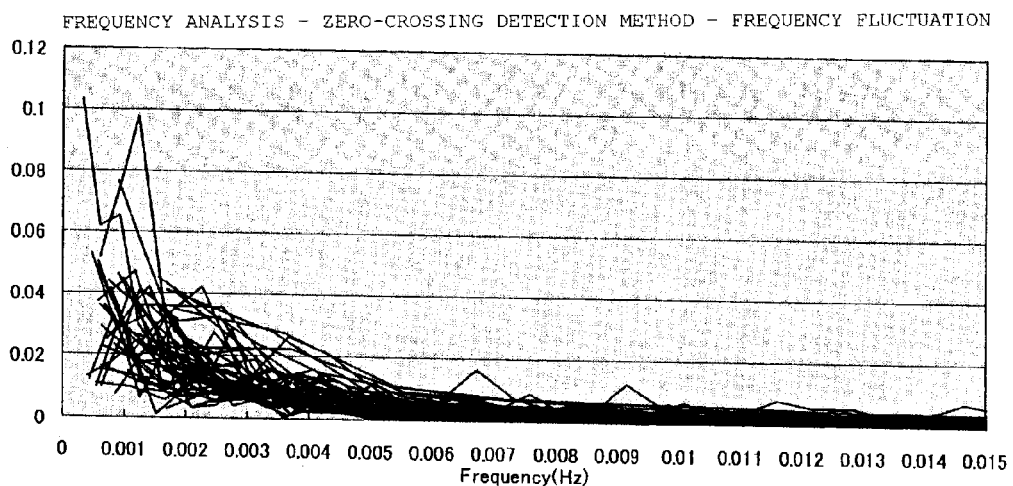
FIG. 24 is a diagram illustrating the frequency analysis result of the frequency fluctuation time-series waveform by means of the zero-crossing method of the heart-part oscillation wave of a person in a wakeful/active state.
Figure 25:
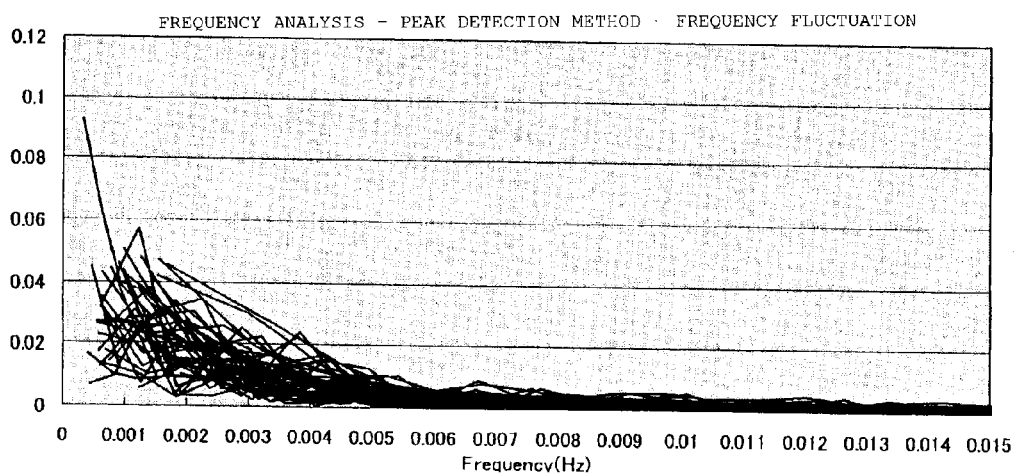
FIG. 25 is a diagram illustrating the frequency analysis result of the frequency fluctuation time-series waveform by means of the peak detection method of the heart-part oscillation wave of a person in a wakeful/active state.

FIGS. 22 and 23 illustrate each frequency analysis result obtained by using the zero-crossing method/peak detection method of the frequency slope time-series waveform of the heart-part oscillation waves of those in the wakeful/active state, while FIGS. 24 and 25 illustrate each frequency analysis result obtained by using the zero-crossing method/peak detection method of the frequency fluctuation time-series waveform of the heart-part oscillation waves in the wakeful/active state. From the frequency analysis result of the frequency slope time-series waveform by using the zero-crossing method in FIG. 22, it can be read that there are three fluctuation frequencies which become the basis of a person in the wakeful/active state, that is, in the vicinity of 0.0017 Hz in a range from 0.001 to 0.002 Hz, in the vicinity of 0.0033 Hz in a range from 0.002 to 0.003 Hz, and the vicinity of 0.0055 Hz in a range from 0.005 to 0.006 Hz, and their power spectrum was 0.0003. The same applies to the peak detection method in FIG. 23. It was considered that people maintain homeostasis while fluctuating in each frequency band having a certain width around these three frequencies as the center frequency of fluctuation. Then, it was considered that as fatigue progresses, the waveform of a region around the 0.0033 Hz at the center becomes stronger, and the power spectrum also becomes stronger by slightly smaller than three times. If the waveform becomes too strong, it changes while fluctuating to the frequency bands on the both sides. This change is quickly shown by the frequency fluctuation.

In the frequency analysis of the frequency fluctuation time-series waveform in FIGS. 24 and 25, a peak is present in the vicinities of 0.0017 Hz and 0.0033 Hz, and the power spectrum rises to 0.04 to 0.02 (0.0017 Hz, 0.0033 Hz) both in the zero-crossing method and the peak detection method. A low one is present at 0.02 to 0.01 (0.0017 Hz, 0.0033 Hz). Here, it is considered that in the frequency slope time-series waveform of the heart-part oscillation wave, a balance of the frequency components of 0.0017 Hz, 0.0033 Hz, and 0.0055 Hz or a distribution rate of the frequency components with the power spectrum as a power value is predominant as a component for estimating a state of a human being, and in the frequency fluctuation time-series waveform of the heart-part oscillation waves, the state of fluctuation in the distribution rate of each frequency component and the power value in the power spectrum of the frequency component at 0.0017 Hz is predominant as a component for estimating a state of a human being.

Figure 26:
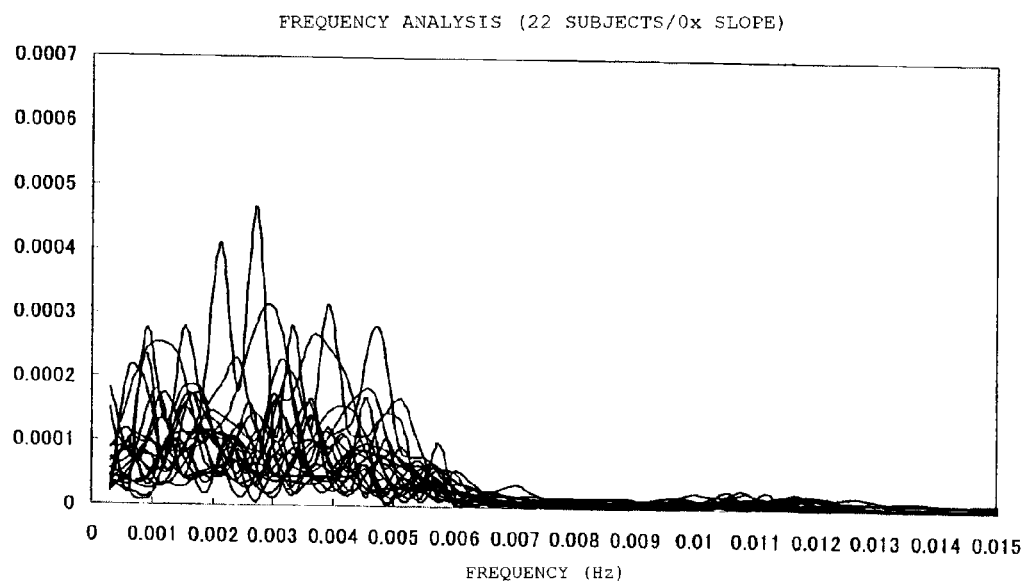
FIG. 26 is a diagram illustrating the frequency analysis result of the frequency slope time-series waveform by means of the zero-crossing method of the heart-part oscillation wave of 22 subjects in a sleep introduction experiment A.
Figure 27:
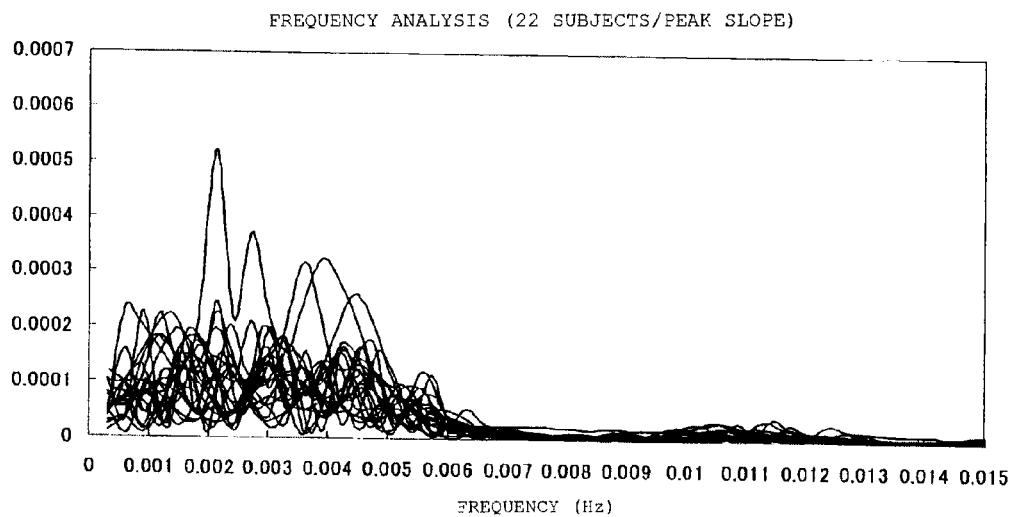
FIG. 27 is a diagram illustrating the frequency analysis result of the frequency slope time-series waveform by means of the peak detection method of the heart-part oscillation wave of 22 subjects in the sleep introduction experiment A.
Figure 28:
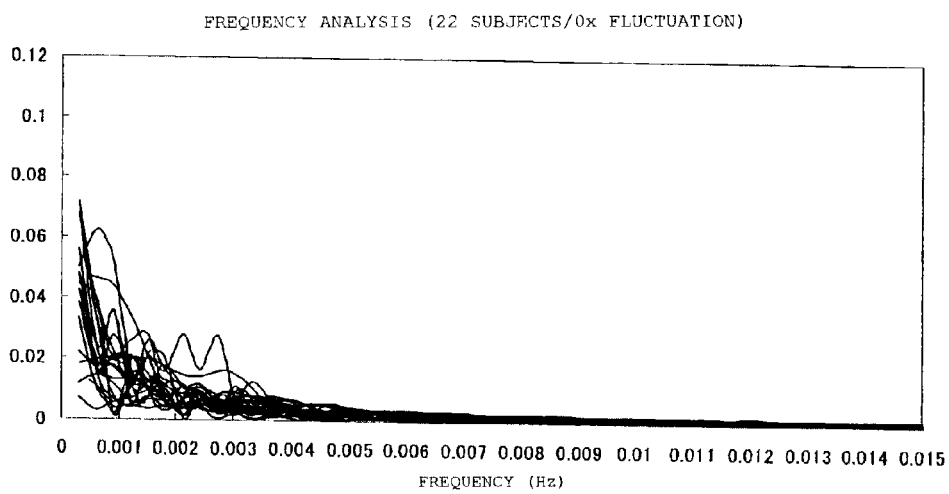
FIG. 28 is a diagram illustrating the frequency analysis result of the frequency fluctuation time-series waveform by means of the zero-crossing method of the heart-part oscillation wave of 22 subjects in the sleep introduction experiment A.
Figure 29:
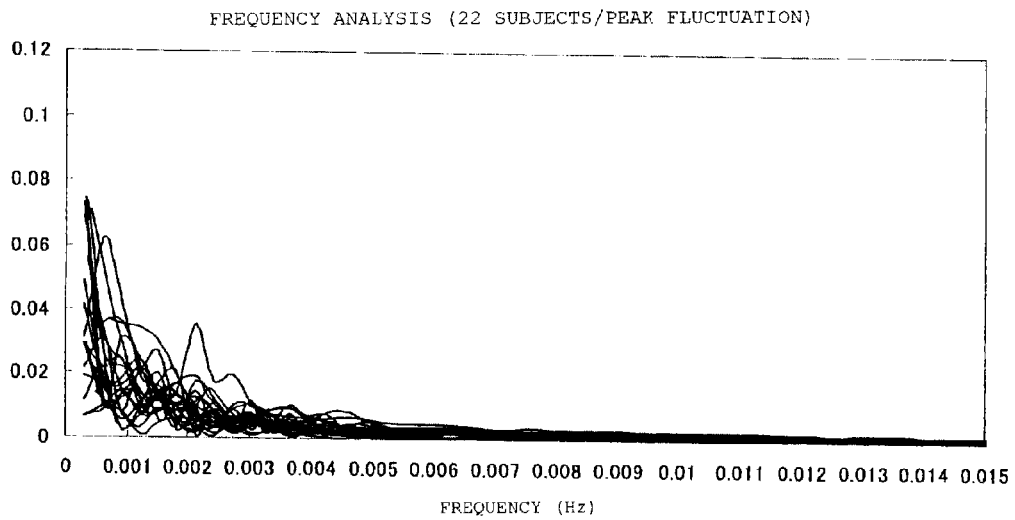
FIG. 29 is a diagram illustrating the frequency analysis result of the frequency fluctuation time-series waveform by means of the peak detection method of the heart-part oscillation wave of 22 subjects in the sleep introduction experiment A.

FIGS. 26 and 27 illustrate each frequency analysis result of the frequency slope time-series waveform of the heart-part oscillation waves of the 22 subjects of the sleep introduction experiment A by the zero-crossing method/peak detection method, while FIGS. 28 and 29 illustrate each frequency analysis result of the frequency fluctuation time-series waveform of the heart-part oscillation waves of the subjects of the sleep introduction experiment A by the zero-crossing method/peak detection method. In the case of falling asleep after maintaining a wakeful state, the number of fluctuation frequencies which become the basis both for the zero-crossing method and the peak detection method is 3 similarly to the wakeful/active state, and the frequency component of 0.0017 Hz is the same, but 0.0033 Hz changed to 0.003 Hz, and 0.0055 Hz changed to 0.0045 Hz. On the other hand, the power spectrum is at the highest at 0.0002, which is reduced to approximately the half of that in the active state. In the frequency analysis result of the frequency fluctuation time-series waveform, the basic components concentrate to 0.0017 Hz to 0.0022 Hz, and the power spectrum was 0.02, which is reduced by 30%. Here, too, it was understood that the distribution rate of the power value specified by the power spectrum of each frequency component is an important element of state estimation.

From the above facts, it can be considered reasonable to extract signals belonging to the three frequency bands, that is, the functional adjustment signal at 0.0027 Hz or less, the fatigue reception signal belonging to the range from 0.002 to 0.0052 Hz, and the activity adjustment signal belonging to the range from 0.004 to 0.007 Hz as three characteristic signals when determining a state of a human being. In the following, 0.00179 Hz, 0.00358 Hz, and 0.00537 Hz belonging to these frequency bands are referred to as the functional adjustment signal, the fatigue reception signal, and the activity adjustment signal, respectively.

(Consideration of Sleep Introduction Experiment A)

"How Characteristic Signals Emerge in Accordance with State"

As the result of the sleep introduction experiment A, how the functional adjustment signal, the fatigue reception signal, and the activity adjustment signal emerge in 30 minutes after the start of the experiment during which a wakeful state is maintained against sleepiness (first half) and at 30 minutes and after during which each subject is allowed to behave on his/her own will (second half), respectively, were organized in accordance with the state.

Group Who could not Sleep in the Second Half of Sleep Introduction Experiment A

Figure 30:
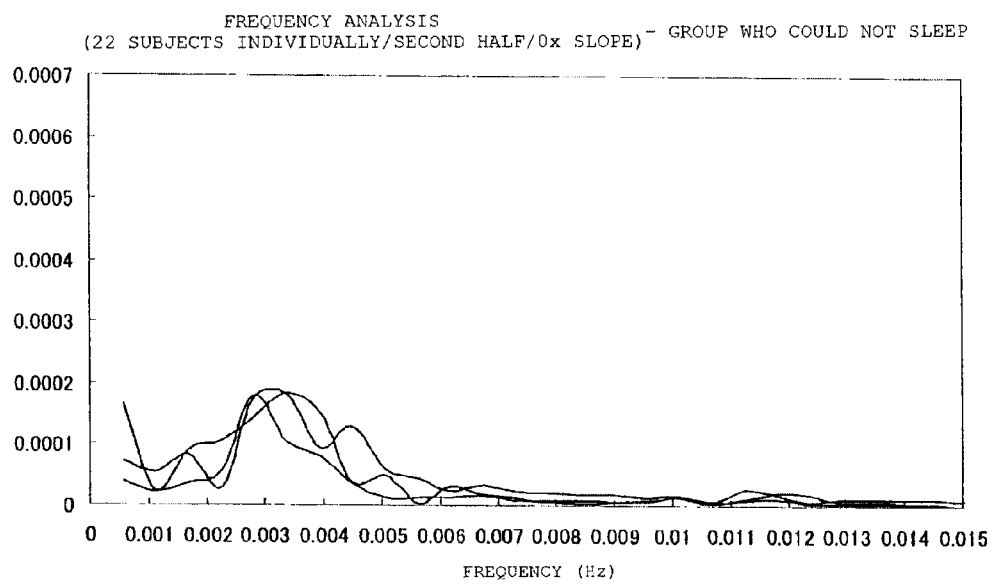
FIG. 30 is a diagram illustrating the frequency analysis result of the frequency slope time-series by means of the zero-crossing method of the heart-part oscillation wave of a group who could not sleep in the second half of the sleep introduction experiment A.
Figure 31:
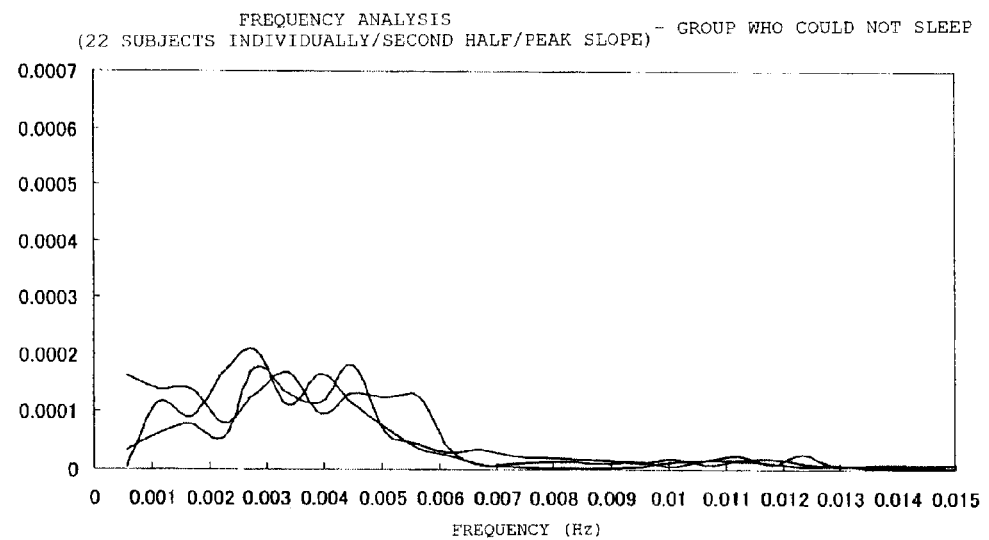
FIG. 31 is a diagram illustrating the frequency analysis result of the frequency slope time-series by means of the peak detection method of the heart-part oscillation wave of the group who could not sleep in the second half of the sleep introduction experiment A.

FIGS. 30 and 31 illustrate a frequency analysis result of the frequency slope time-series of the heart-part oscillation waves of a group who could not sleep in the second half of the sleep introduction experiment A. With the zero-crossing method, all the three subjects had a high power spectrum at 0.00358 Hz, a low power spectrum at 0.00179 Hz and 0.00537 Hz, which formed a relatively gentle projecting shape. The peak detection method also illustrated the similar tendency. The height of the power spectrum indicated 0.0002 both in the zero-crossing method and the peak detection method. This was close to the balance of the distribution rate of the power spectrum of each frequency in the above-described wakeful/active state.

Figure 32:
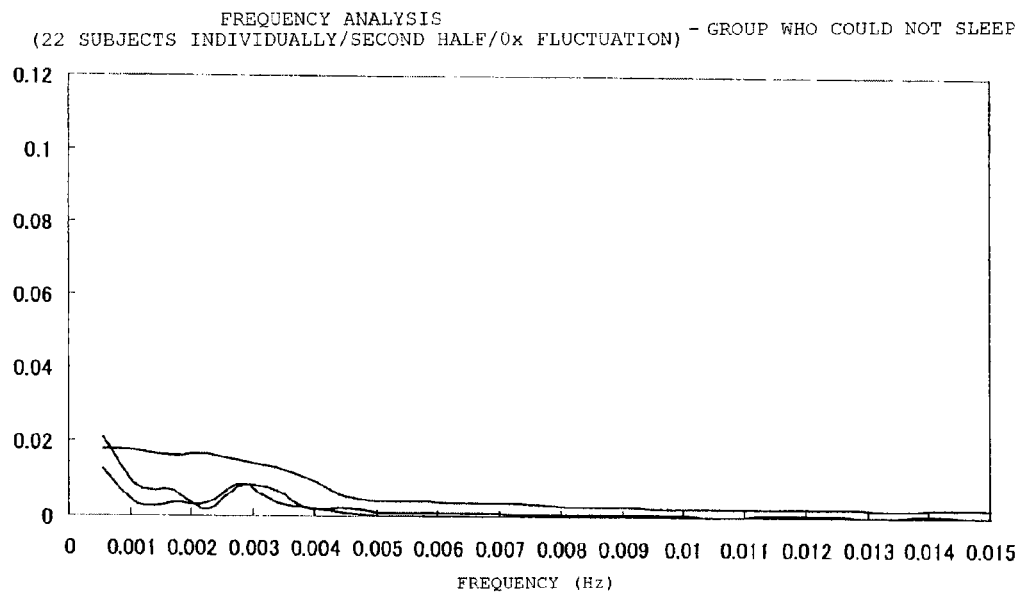
FIG. 32 is a diagram illustrating the frequency analysis result of the frequency fluctuation time-series by means of the zero-crossing method of the heart-part oscillation wave of the group who could not sleep in the second half of the sleep introduction experiment A.
Figure 33:
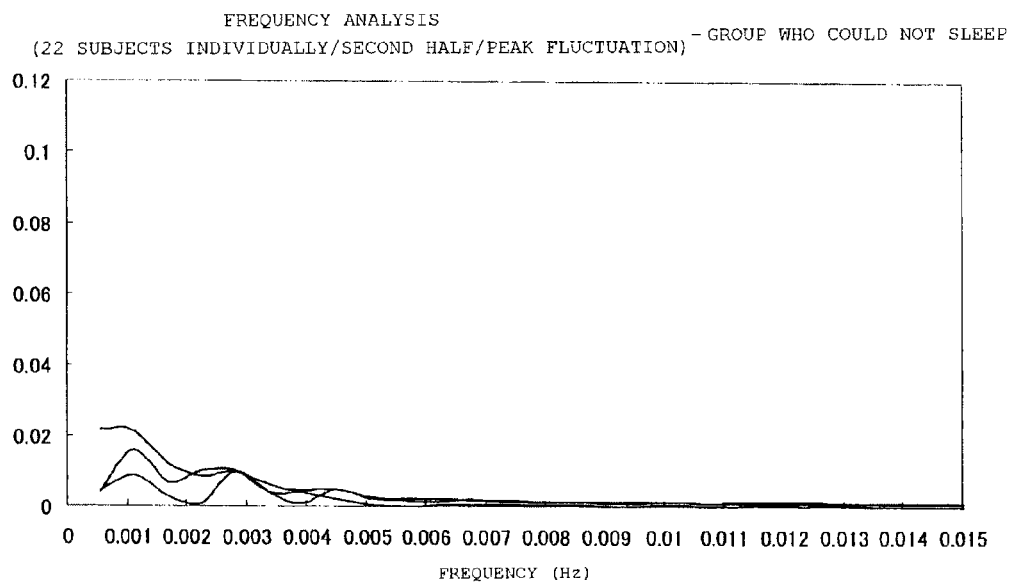
FIG. 33 is a diagram illustrating the frequency analysis result of the frequency fluctuation time-series by means of the peak detection method of the heart-part oscillation wave of the group who could not sleep in the second half of the sleep introduction experiment A.

In the frequency analysis results of the frequency fluctuation time-series waveform (FIGS. 32 and 33), components at 0.00179 Hz, 0.00358 Hz, and 0.00537 Hz were small, and the distribution rate of the power spectrum was smoothed both in the zero-crossing method and the peak detection method. Here, the distribution rate of the power value specified by the power spectrum of each frequency component was also close to that in the wakeful/active state.

Group Who Fell Asleep in the Second Half of Sleep Introduction Experiment A

Figure 34:
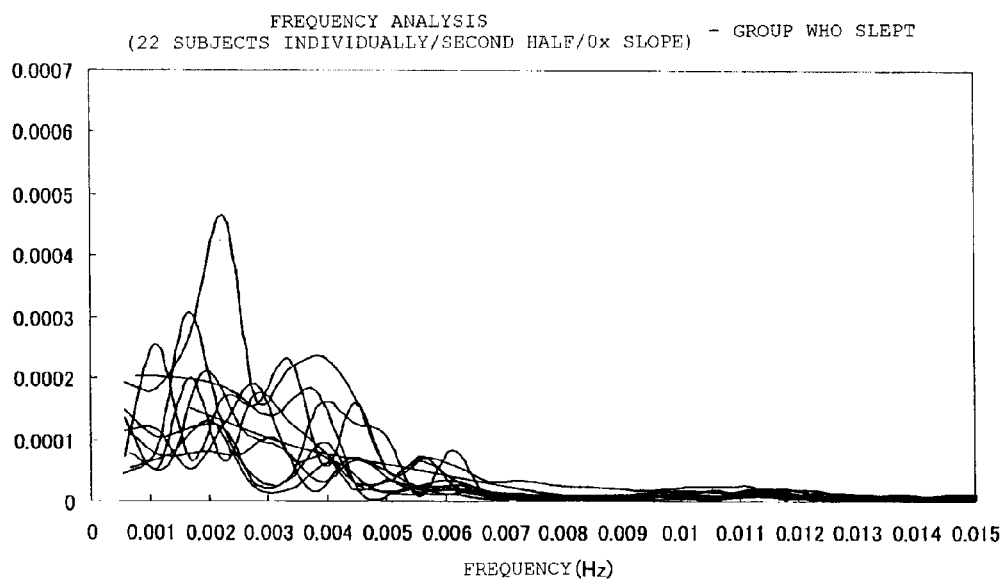
FIG. 34 is a diagram illustrating the frequency analysis result of the frequency slope time-series by means of the zero-crossing method of the heart-part oscillation wave of a group who fell asleep in the second half of the sleep introduction experiment A.
Figure 35:
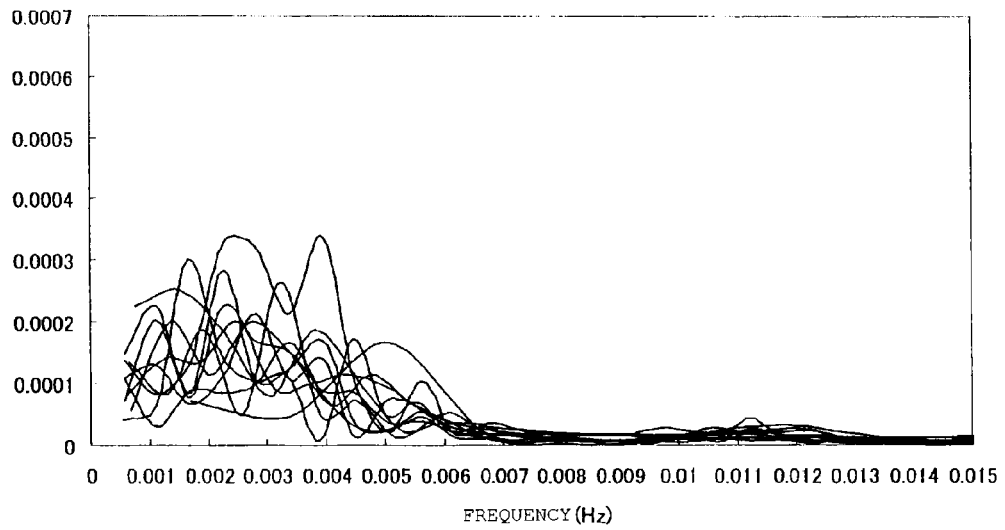
FIG. 35 is a diagram illustrating the frequency analysis result of the frequency slope time-series by means of the peak detection method of the heart-part oscillation wave of the group who fell asleep in the second half of the sleep introduction experiment A.

FIGS. 34 and 35 illustrate a frequency analysis result of the frequency slope time-series waveform of the heart-part oscillation waves of a group who fell asleep in the second half of the sleep introduction experiment A. With the zero-crossing method, the power spectrum became high to 0.00025 to 0.0003 at 0.00179 Hz and the power spectrum halved at 0.00358 Hz and 0.00537 Hz. With the peak detection method, the power spectrums at 0.00179 Hz and 0.00358 Hz were substantially equal and the power spectrum at 0.00537 Hz rapidly decreased to ⅓. In the frequency slope time-series waveform, a rise in the 0.00179 Hz component and falls in the 0.00358 Hz and 0.00537 Hz components were generated and a balance of the distribution rate of the power spectrum of each frequency component was considered to be predominant. Here, the distribution rate was not close to the balance of the distribution rate of the power spectrum of each frequency in the above-described wakeful/active state but suggested a possibility of a unique power-spectrum distribution rate emerging during sleep, that is, a tendency of descending over time.

Figure 36:
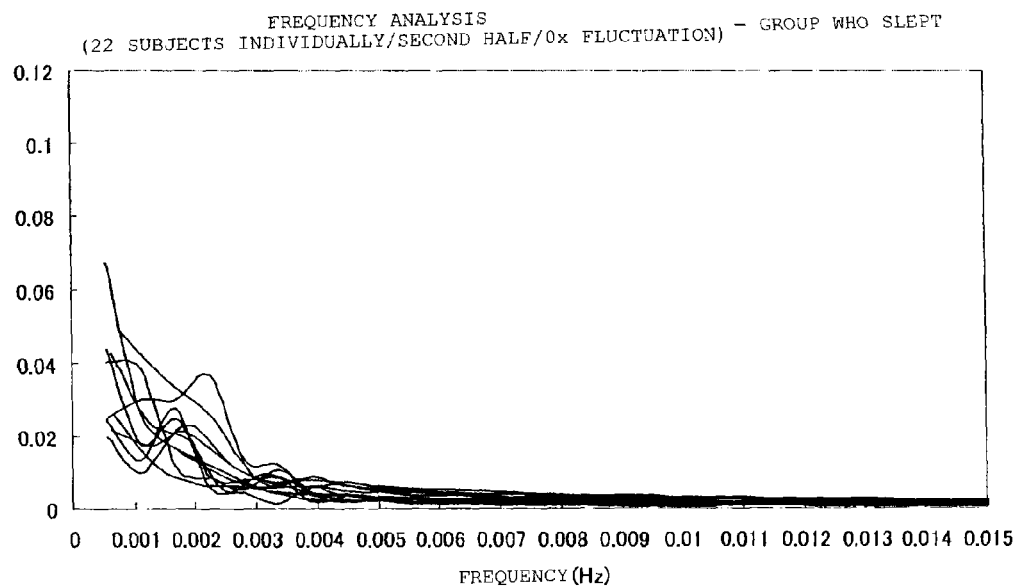
FIG. 36 is a diagram illustrating the frequency analysis result of the frequency fluctuation time-series by means of the zero-crossing method of the heart-part oscillation wave of the group who fell asleep in the second half of the sleep introduction experiment A.
Figure 37:
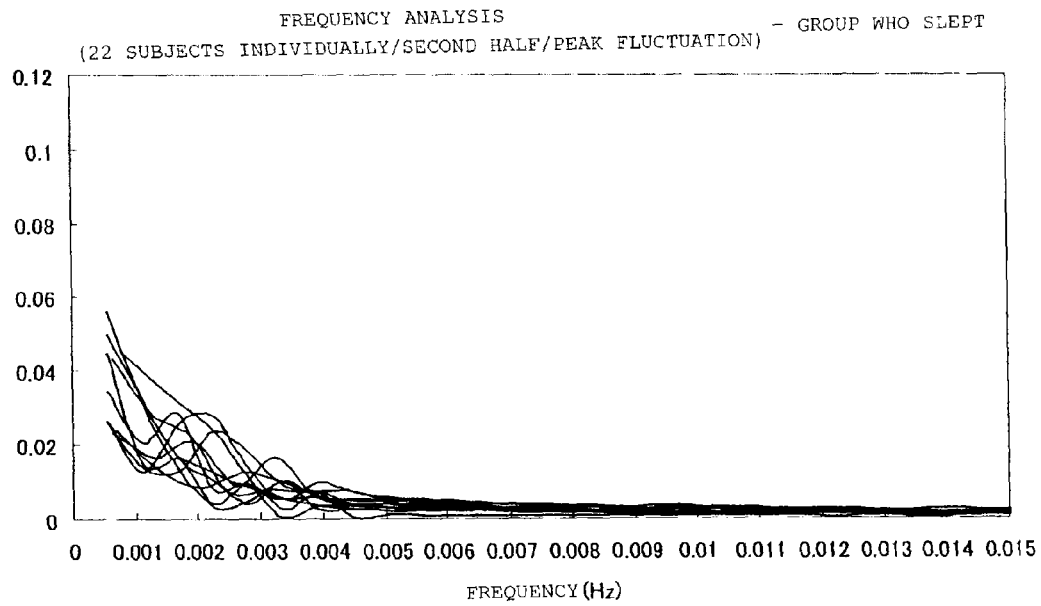
FIG. 37 is a diagram illustrating the frequency analysis result of the frequency fluctuation time-series by means of the peak detection method of the heart-part oscillation wave of the group who fell asleep in the second half of the sleep introduction experiment A.

In the frequency analysis result of the frequency fluctuation time-series waveform (FIGS. 36 and 37), the power spectrum at 0.00179 Hz was strong, the 0.00358 Hz component and the 0.00537 component rapidly decreased, and the characteristic change of the distribution rate of the power spectrum, that is, the distribution rate of a rapid descending over time emerged both in the zero-crossing method and the peak detection method.

Figure 38:
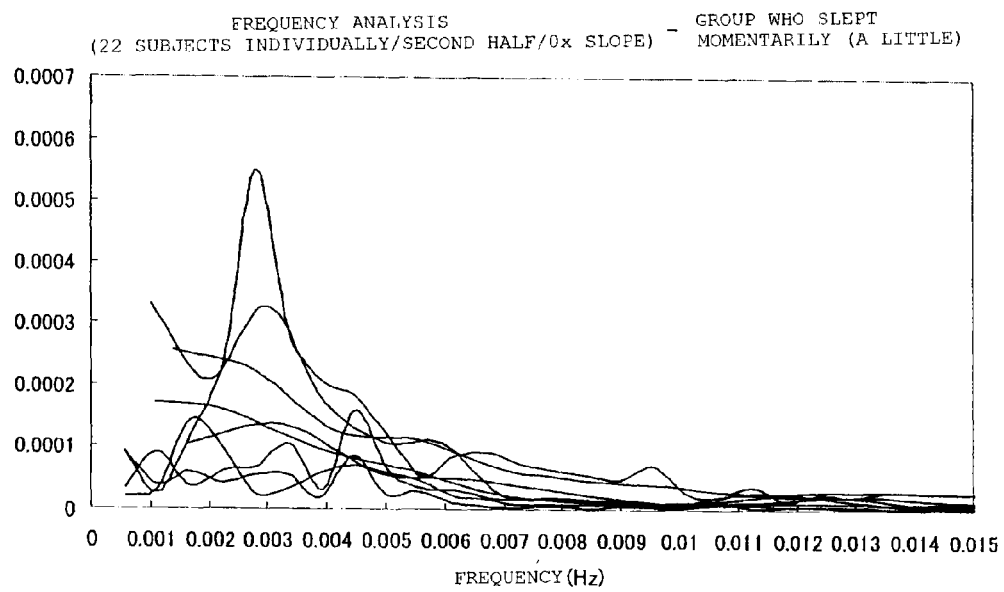
FIG. 38 is a diagram illustrating the frequency analysis result of the frequency slope time-series by means of the zero-crossing method of the heart-part oscillation wave of a group who slept a little in the second half of the sleep introduction experiment A.
Figure 39:
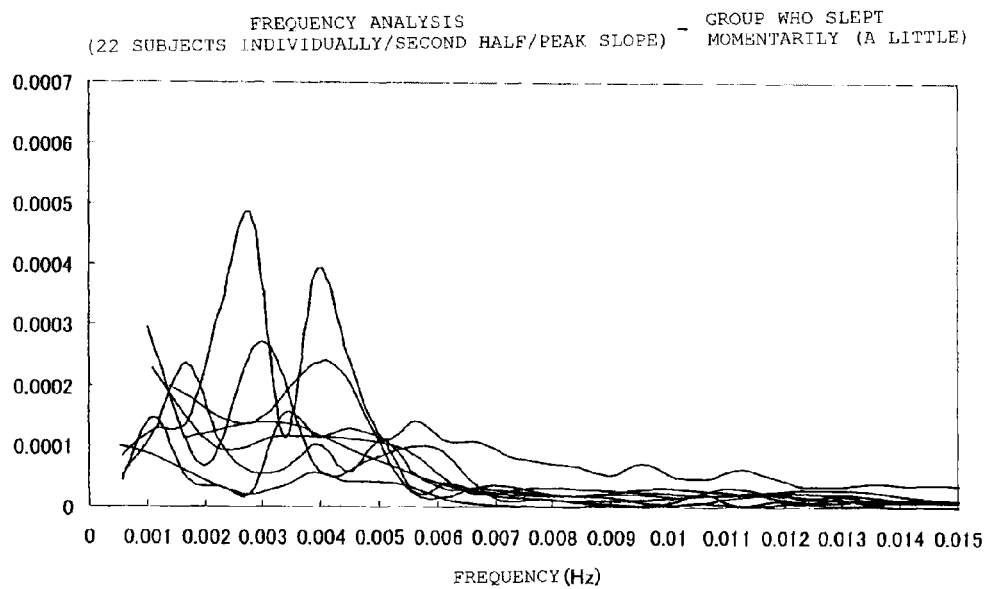
FIG. 39 is a diagram illustrating the frequency analysis result of the frequency slope time-series by means of the peak detection method of the heart-part oscillation wave of the group who slept a little in the second half of the sleep introduction experiment A.

Group Who Slept a Little (Momentarily) in the Second Half of Sleep Introduction Experiment A FIGS. 38 and 39 illustrate a frequency analysis result of the frequency slope time-series waveform of the heart-part oscillation waves of a group who slept a little (momentarily) in the second half of the sleep introduction experiment A. With the zero-crossing method, the power spectrum entirely lowered to the half of that when sleeping or to 0.0001 or less, which was close to the characteristics of the group without fluctuation any longer and the group who could not sleep, and the power spectrum in the vicinity of 0.003 Hz at the center grew to twice to three times or to 0.0003 to 0.00055 in some cases. It was considered that the result depended on resistance against sleepiness. However, if narrowed to the three frequencies of 0.00179 Hz, 0.00358 Hz, and 0.00537 Hz, the distribution rate of the power spectrum uniformly showed the same tendency which is a tendency of descending over time. On the other hand, with the peak detection method, the result was classified to a group in which the power spectrums of the three frequencies of 0.00179 Hz, 0.00358 Hz, and 0.00537 Hz entirely sank to 0.0001 and a group in which the power spectrums of the three frequencies of 0.00179 Hz, 0.00358 Hz, and 0.00537 Hz were at 0.0001 to 0.0002 which were the same as the former but a power spectrum grew significantly between the 0.00179 and 0.00358 Hz and between 0.00358 Hz and 0.00537 Hz. Here, too, by imposing a filter of a target frequency, though there was large fluctuation in the intermediate frequency band, concentration to a descending tendency which is one pattern could be confirmed.

Figure 40:
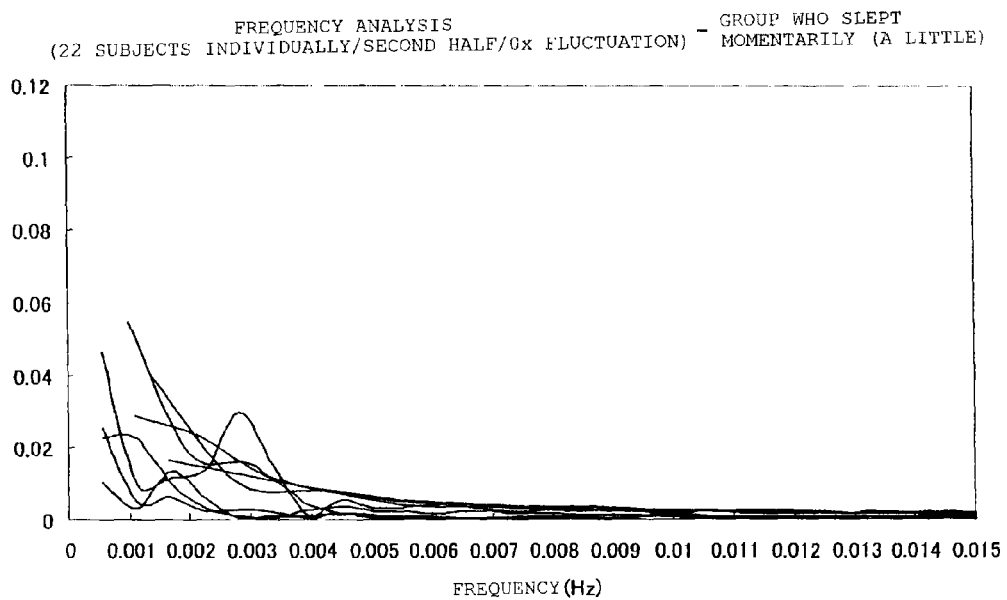
FIG. 40 is a diagram illustrating the frequency analysis result of the frequency fluctuation time-series by means of the zero-crossing method of the heart-part oscillation wave of the group who slept a little in the second half of the sleep introduction experiment A.
Figure 41:
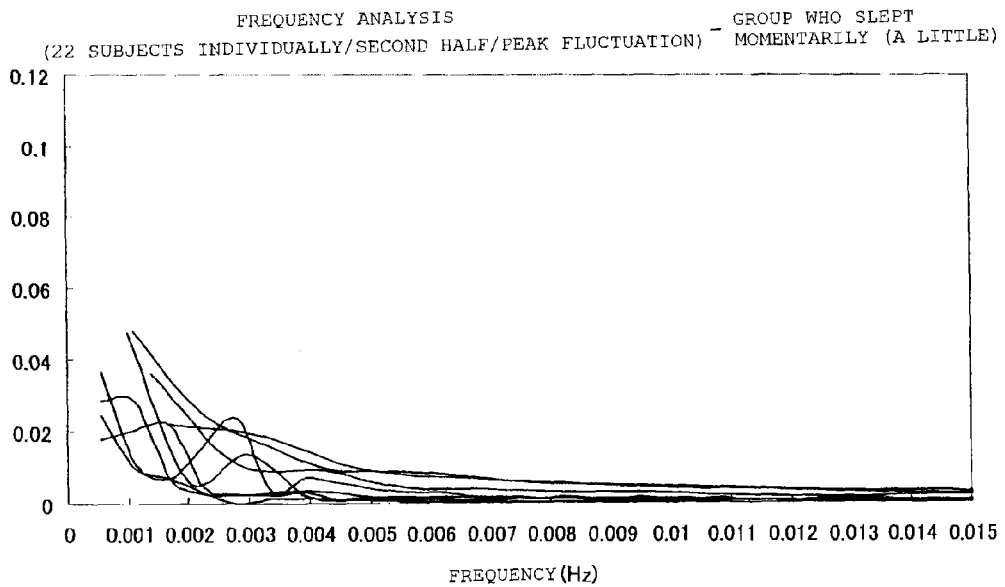
FIG. 41 is a diagram illustrating the frequency analysis result of the frequency fluctuation time-series by means of the peak detection method of the heart-part oscillation wave of the group who slept a little in the second half of the sleep introduction experiment A.

In the frequency analysis result of the frequency fluctuation time-series waveform (FIGS. 40 and 41), the power spectrum at 0.00179 Hz was strong, the components at 0.00358 Hz and 0.00537 Hz rapidly decreased, and the characteristic change in the distribution rate of the power spectrum, which is a rapid descending distribution rate emerged both in the zero-crossing method and the peak detection method.

That is, as illustrated in FIGS. 30 to 41, in the wakeful/active state and a state from sleepiness to sleep, it was suggested that the distribution rates of the power spectrums illustrated by the three frequencies indicated characteristic tendencies, respectively.

Figure 42:
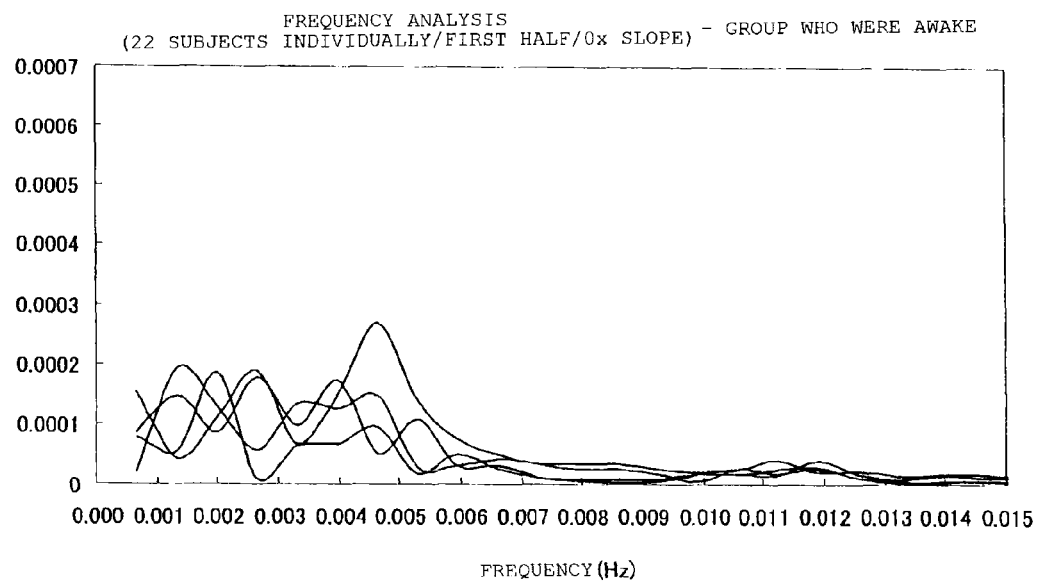
FIG. 42 is a diagram illustrating the frequency analysis result of the frequency slope time-series by means of the zero-crossing method of the heart-part oscillation wave of a group who were awake in the first half of the sleep introduction experiment A.
Figure 43:
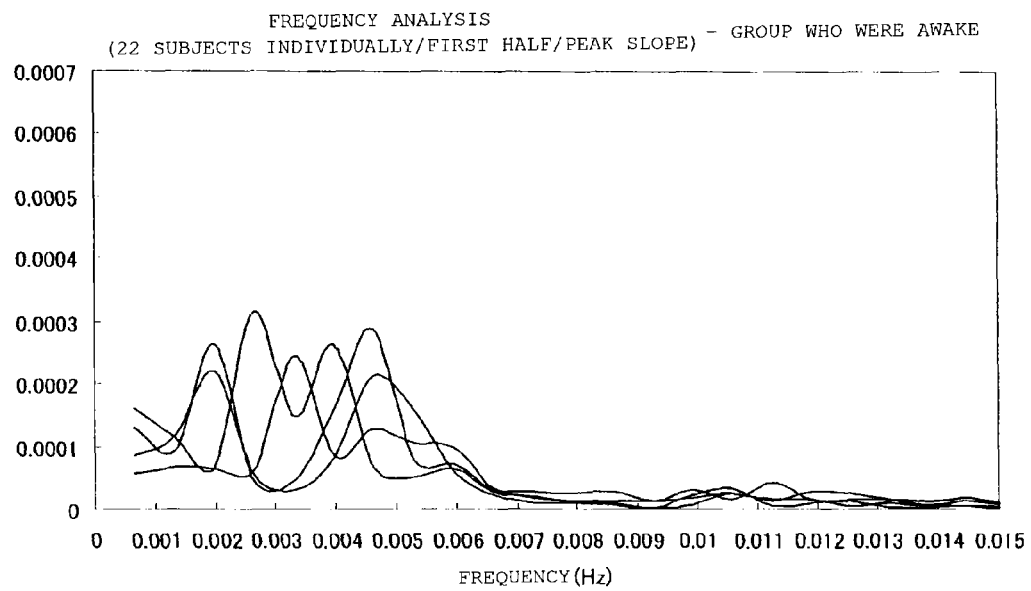
FIG. 43 is a diagram illustrating the frequency analysis result of the frequency slope time-series by means of the peak detection method of the heart-part oscillation wave of the group who were awake in the first half of the sleep introduction experiment A.

Group Who Maintained Wakeful State in the First Half of Sleep Introduction Experiment A Subsequently, a frequency analysis result in the first half of the sleep introduction experiment A in which resistance against sleepiness was forced will be verified. Regarding the group who maintained the wakeful state, in the frequency analysis result of the frequency slope time-series waveform of the heart-part oscillation waves illustrated in FIGS. 42 and 43, the power spectrum fluctuated between 0.0001 and 0.0002 at 0.00179 Hz, 0.00358 Hz, and 0.00537 Hz in the zero-crossing method. This gentle change was considered to be a characteristic of maintenance of homeostasis in the wakeful state. With the peak detection method, too, by applying a filter of 0.00179 Hz, 0.00358 Hz, and 0.00537 Hz, a state in which the power spectrum gently changed between 0.00005 and 0.0002 and maintained homeostasis while fluctuating was suggested.

Figure 44:
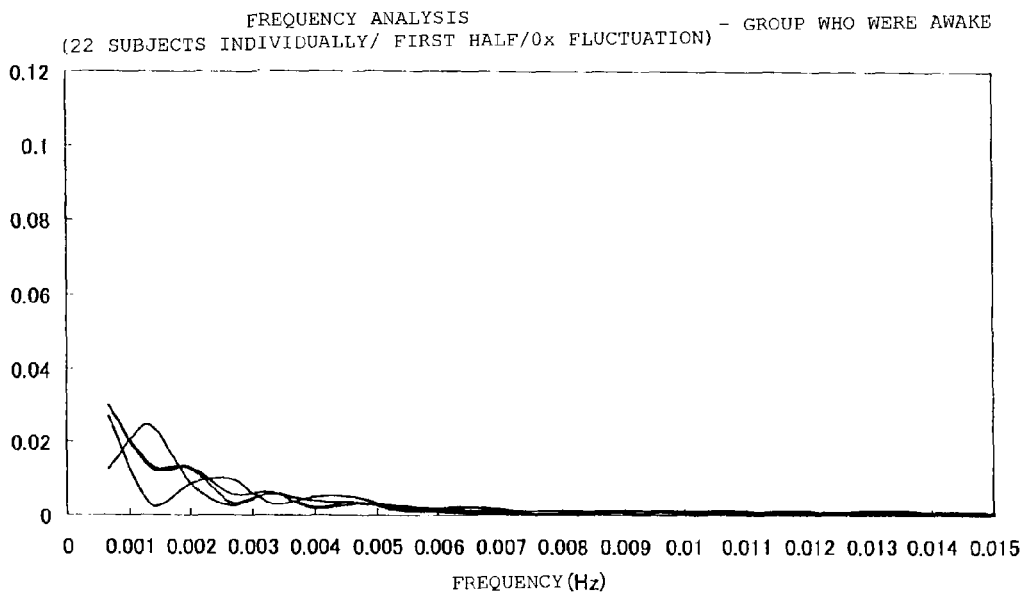
FIG. 44 is a diagram illustrating the frequency analysis result of the frequency fluctuation time-series by means of the zero-crossing method of the heart-part oscillation wave of the group who were awake in the first half of the sleep introduction experiment A.
Figure 45:
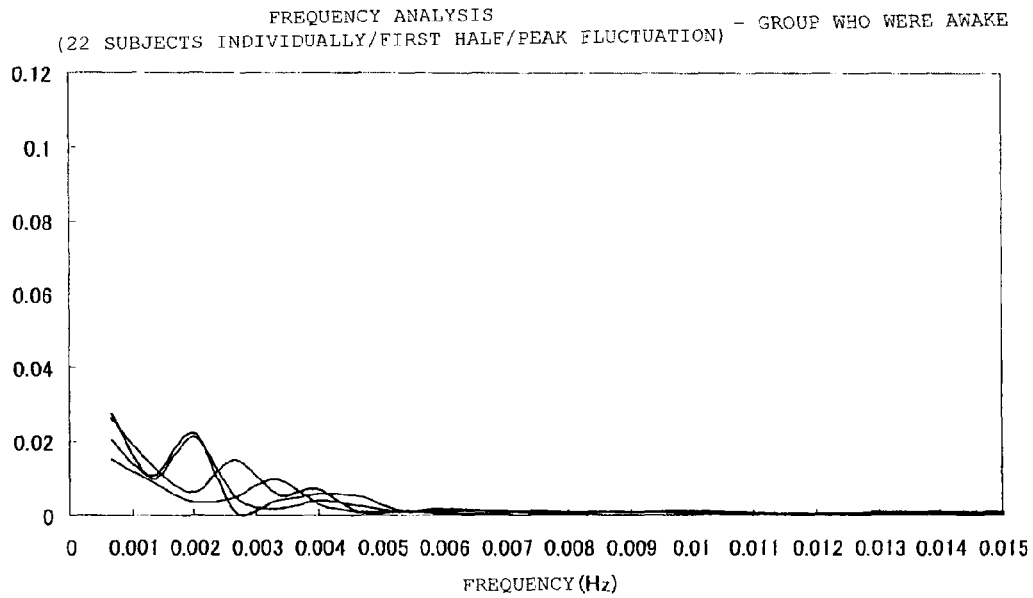
FIG. 45 is a diagram illustrating the frequency analysis result of the frequency fluctuation time-series by means of the peak detection method of the heart-part oscillation wave of the group who were awake in the first half of the sleep introduction experiment A.

In the frequency analysis result of the frequency fluctuation time-series waveform illustrated in FIGS. 44 and 45, the components of 0.00179 Hz, 0.00358 Hz, and 0.00537 Hz became small, and the distribution rate of the power spectrum was smoothed both in the zero-crossing method and the peak detection method. Here, too, the distribution rate of the power value specified by the power spectrum of each frequency component was close to the wakeful/active state.

Group Who were Talking in the First Half of Sleep Introduction Experiment A

Figure 46:
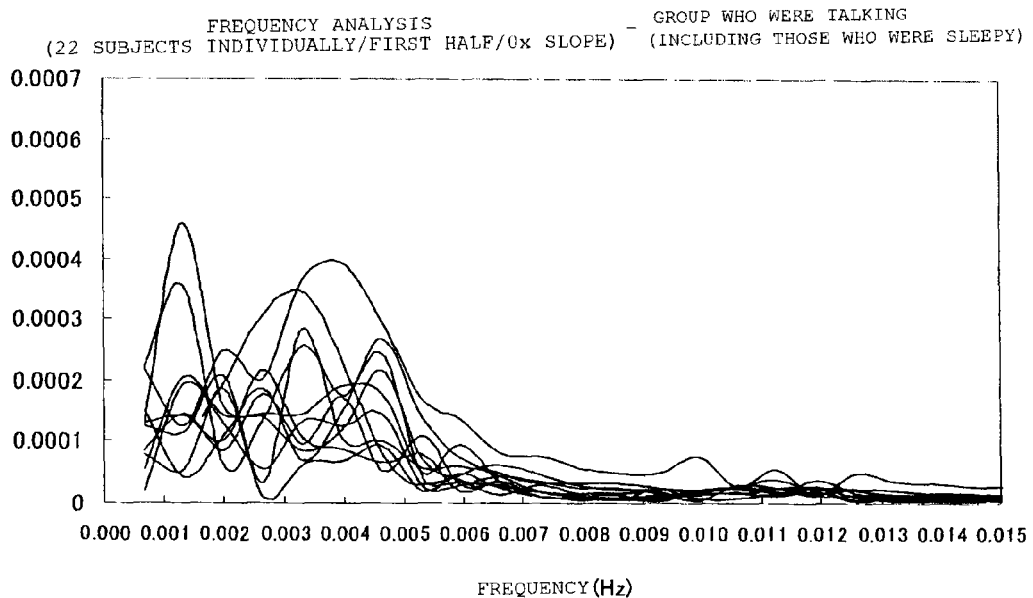
FIG. 46 is a diagram illustrating the frequency analysis result of the frequency slope time-series by means of the zero-crossing method of the heart-part oscillation wave of a group who were talking in the first half of the sleep introduction experiment A.
Figure 47:
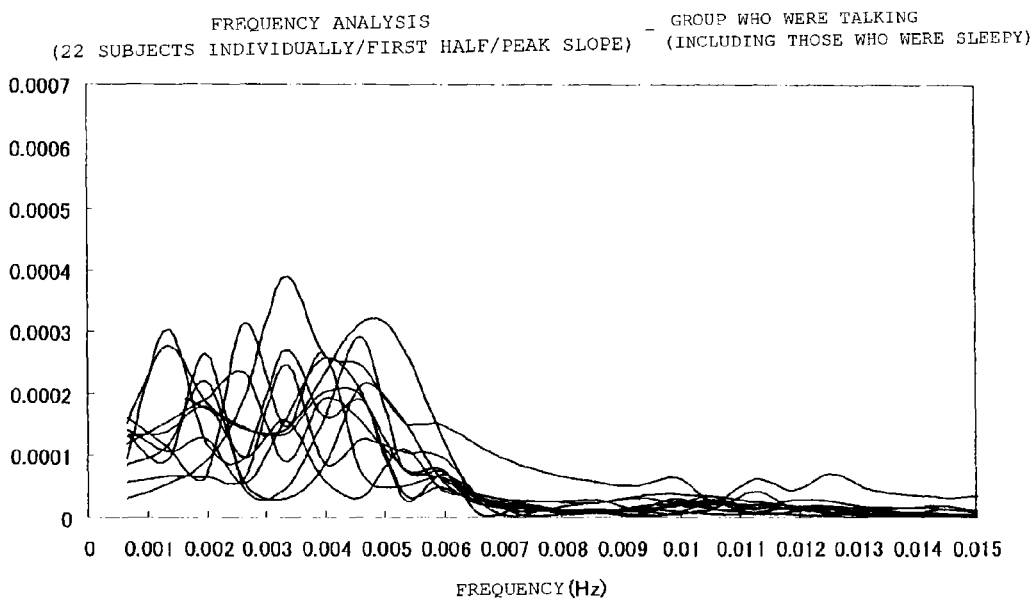
FIG. 47 is a diagram illustrating the frequency analysis result of the frequency slope time-series by means of the peak detection method of the heart-part oscillation wave of the group who were talking in the first half of the sleep introduction experiment A.

The frequency analysis result of the frequency slope time-series waveform of the heart-part oscillation waves of a group who were talking is illustrated in FIGS. 46 and 47. The group who were talking had the power spectrum at 0.00537 Hz at the same level of 0.00005 to 0.0002 or less in the zero-crossing method as compared with the group who maintained the wakeful state, but the power spectrum at 0.00179 Hz and 0.00358 Hz was within a range from 0.00005 to 0.00045, and a width of fluctuation further increased. With the peak detection method, the fluctuation width of the power spectrum of each frequency at 0.00179 Hz, 0.00358 Hz, and 0.00537 Hz showed a similar tendency of 0.00005 to 0.0004 or less as compared with the group who maintained the wakeful state. Those who felt sleepiness for a moment showed a higher power spectrum by approximately 30% probably because they resisted sleepiness.

Figure 48:
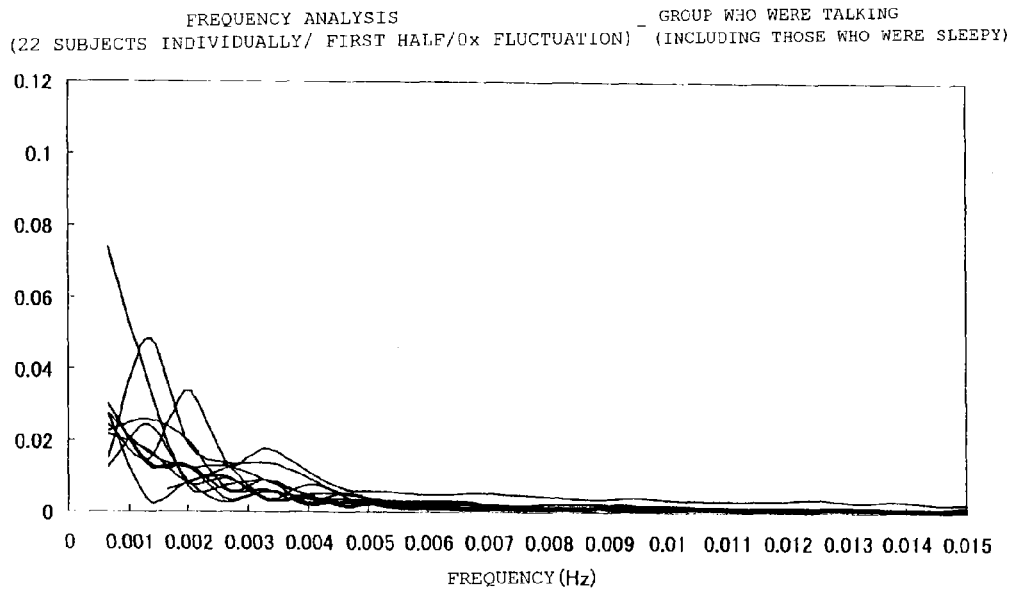
FIG. 48 is a diagram illustrating the frequency analysis result of the frequency fluctuation time-series by means of the zero-crossing method of the heart-part oscillation wave of the group who were talking in the first half of the sleep introduction experiment A.
Figure 49:
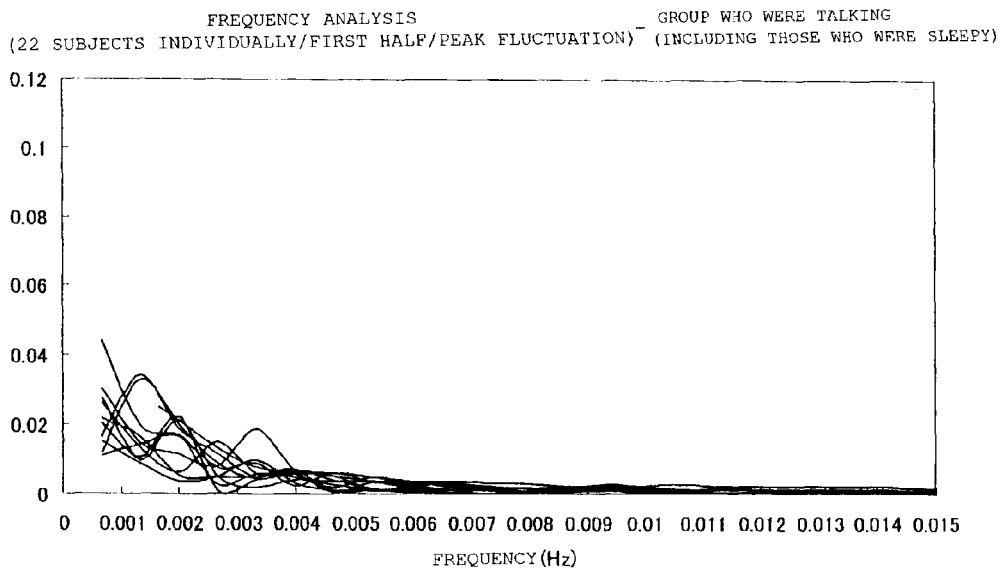
FIG. 49 is a diagram illustrating the frequency analysis result of the frequency fluctuation time-series by means of the peak detection method of the heart-part oscillation wave of the group who were talking in the first half of the sleep introduction experiment A.

In the frequency analysis result of the frequency fluctuation time-series waveform illustrated in FIGS. 48 and 49, the components at 0.00179 Hz, 0.00358 Hz, and 0.00537 Hz became small, and the distribution rate of the power spectrum was smoothed both in the zero-crossing method and the peak detection method. Here, too, the distribution rate of the power value specified by the power spectrum of each frequency component was close to the wakeful/active state.

Figure 50:
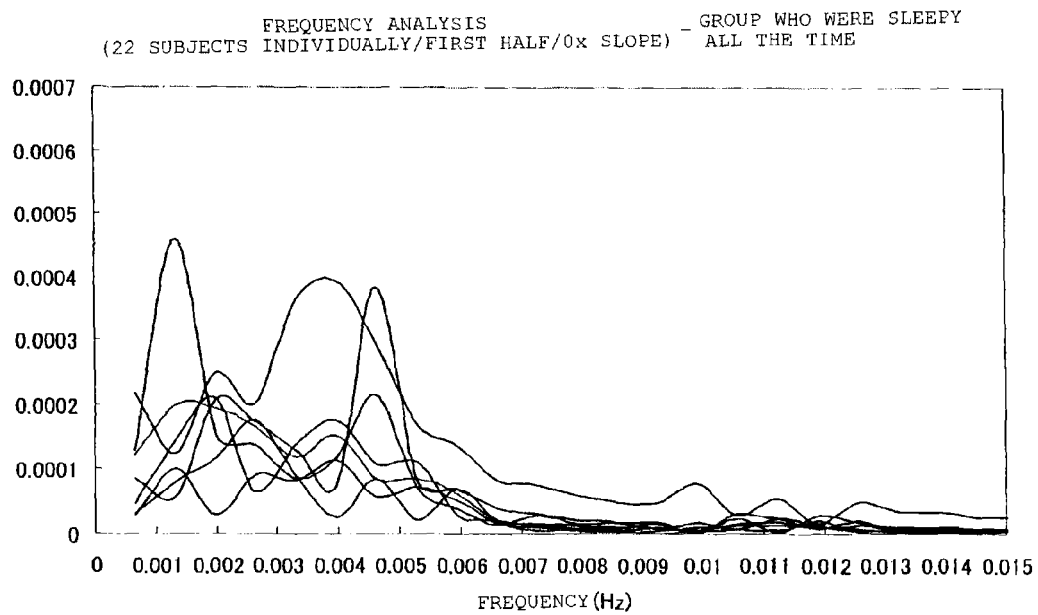
FIG. 50 is a diagram illustrating the frequency analysis result of the frequency slope time-series by means of the zero-crossing method of the heart-part oscillation wave of a group who were sleepy all the time in the first half of the sleep introduction experiment A.
Figure 51:
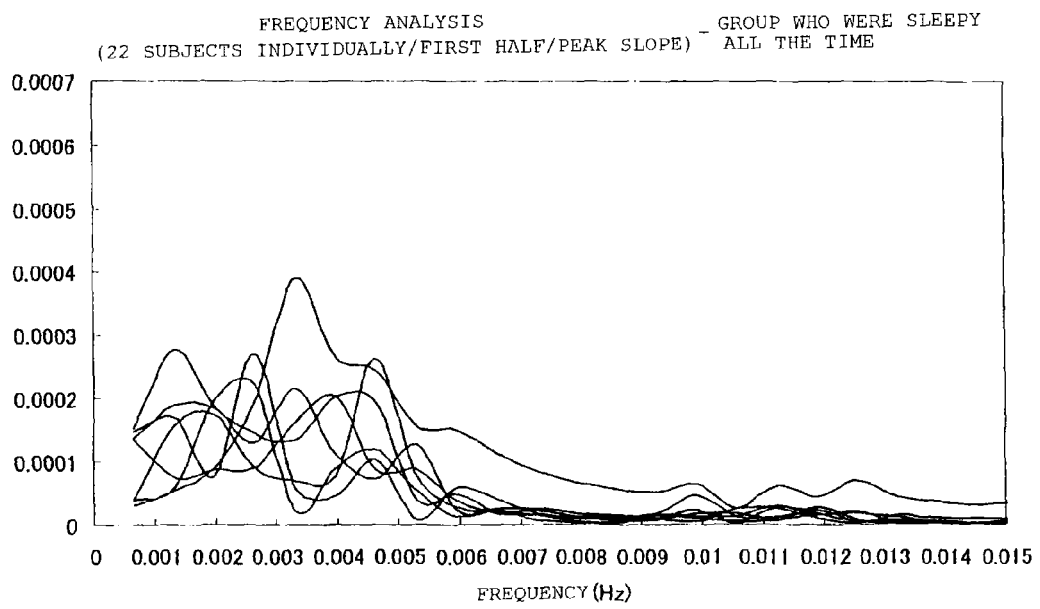
FIG. 51 is a diagram illustrating the frequency analysis result of the frequency slope time-series by means of the peak detection method of the heart-part oscillation wave of the group who were sleepy all the time in the first half of the sleep introduction experiment A.

Group Who were Sleepy all the Time in the First Half of Sleep Introduction Experiment A The frequency analysis result of the frequency slope time-series waveform of the heart-part oscillation waves of a group who were sleepy all the time is illustrated in FIGS. 50 and 51. The group who were sleepy all the time had a large change of the power spectrum at 0.00179 Hz and 0.00358 Hz as 0.00005 to 0.0004, and the power spectrum at 0.00537 Hz had small fluctuation between 0.00005 to 0.00016 in the zero-crossing method, which indicated a state of resistance against falling asleep. On the other hand, in the peak detection method, the fluctuation of the power spectrum was between 0.00005 and 0.00025 at 0.00179 Hz, between 0.00002 and 0.0004 or less at 0.00358 Hz and between 0.00002 to 0.0002 or less at 0.00537 Hz and showed the same tendency as that in the wakeful state except that the values at 0.00179 Hz and 0.00358 Hz became high since sleepiness was felt. That is, if sleepiness occurred, the group was divided into a group who had a high value at 0.00179 Hz and a group who had high values at 0.00358 Hz and 0.00537 Hz in the zero-crossing method. The former are considered to be people who did not resist against falling asleep, while the latter are people who tried to resist against falling asleep. Moreover, with the peak detection method, the values at 0.00179 Hz, 0.00358 Hz, and 0.00537 Hz became high as a whole. Some had the fluctuation width of the power spectrum slightly less than twice of that in a period without sleepiness.

Figure 52:
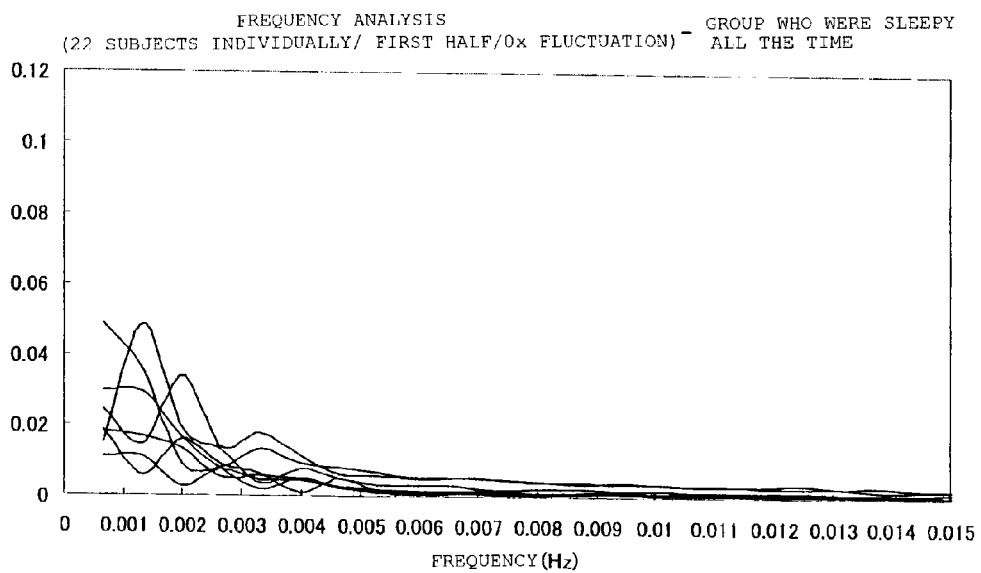
FIG. 52 is a diagram illustrating the frequency analysis result of the frequency fluctuation time-series by means of the zero-crossing method of the heart-part oscillation wave of the group who were sleepy all the time in the first half of the sleep introduction experiment A.
Figure 53:
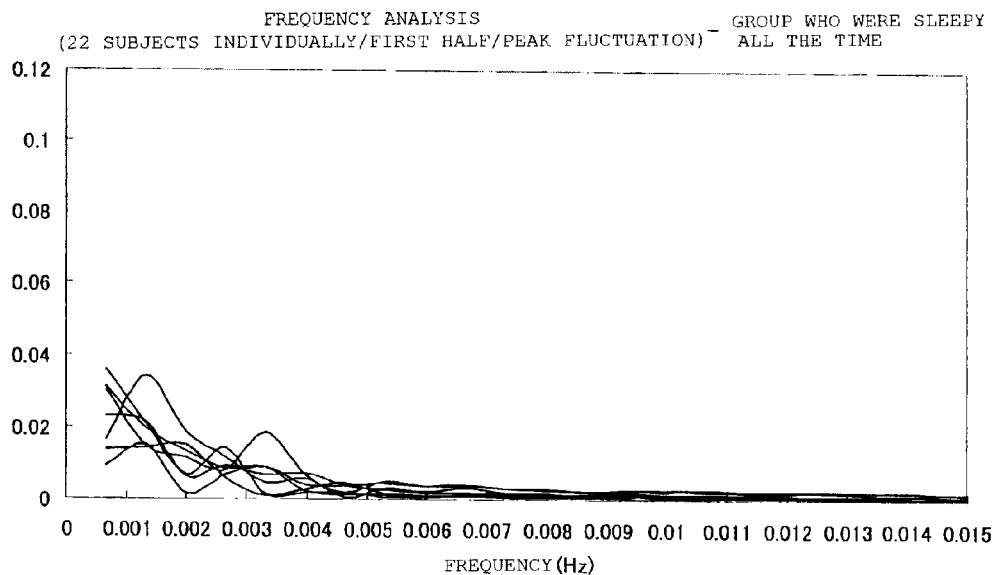
FIG. 53 is a diagram illustrating the frequency analysis result of the frequency fluctuation time-series by means of the peak detection method of the heart-part oscillation wave of the group who were sleepy all the time in the first half of the sleep introduction experiment A.

In the frequency analysis result of the frequency fluctuation time-series waveform illustrated in FIGS. 52 and 53, the power spectrum at 0.00179 Hz became strong, the components at 0.00358 Hz and 0.00537 Hz rapidly decreased, and the characteristic change of the distribution rate of the power spectrum, which is a rapid descending distribution rate emerged both in the zero-crossing method and the peak detection method.

(Consideration of Sleep Introduction Experiment B)

Figure 54:
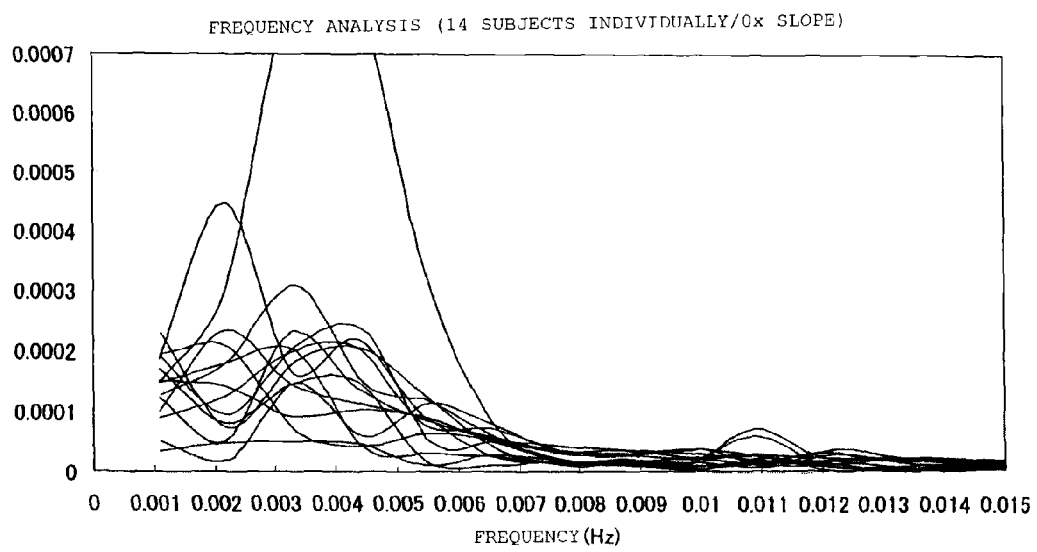
FIG. 54 is a diagram illustrating the frequency analysis result of the frequency slope time-series by means of the zero-crossing method of the heart-part oscillation wave of subjects of a sleep introduction experiment B.
Figure 55:
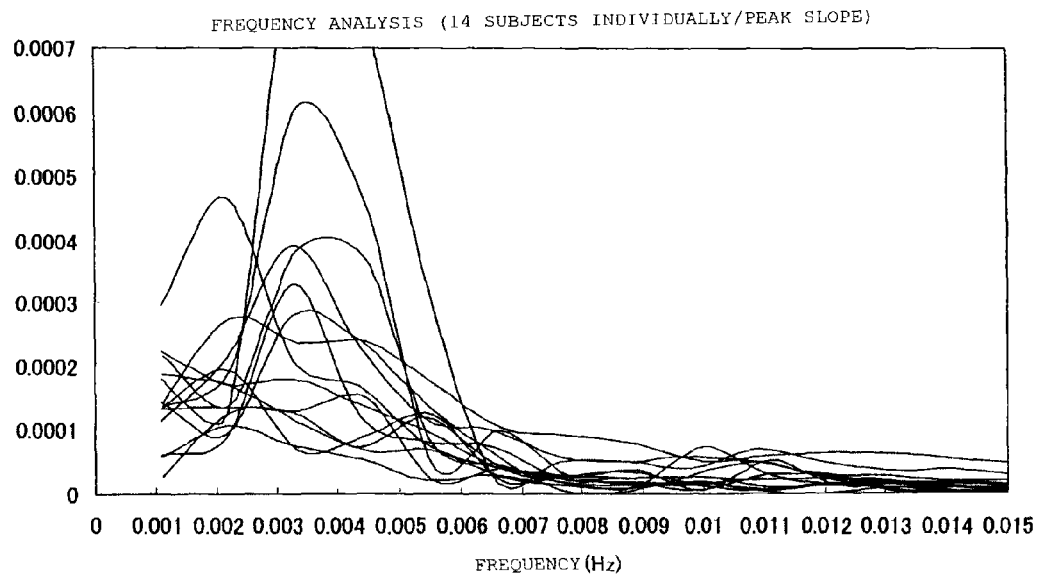
FIG. 55 is a diagram illustrating the frequency analysis result of the frequency slope time-series by means of the peak detection method of the heart-part oscillation wave of the subjects of the sleep introduction experiment B.
Figure 56:
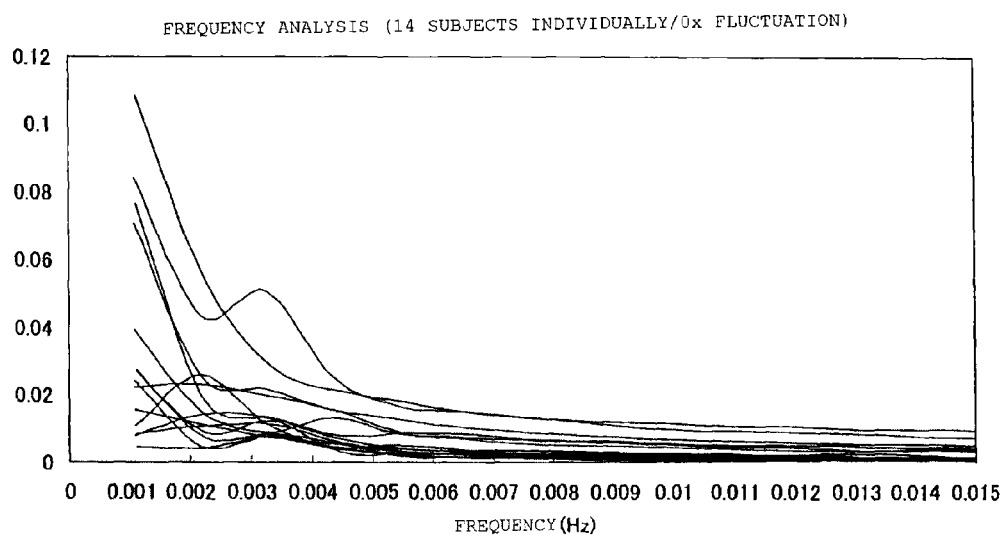
FIG. 56 is a diagram illustrating the frequency analysis result of the frequency fluctuation time-series by means of the zero-crossing method of the heart-part oscillation wave of the subjects of the sleep introduction experiment B.
Figure 57:
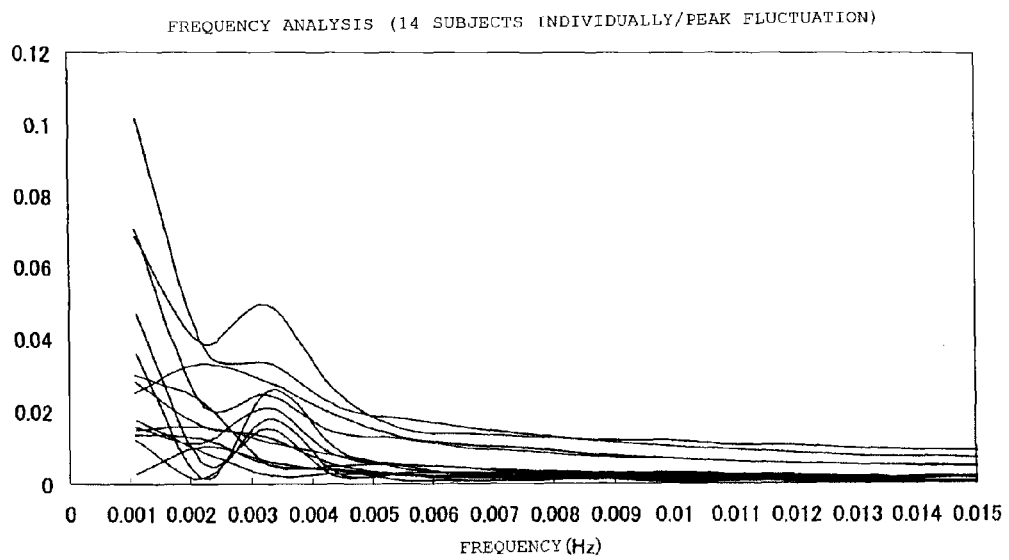
FIG. 57 is a diagram illustrating the frequency analysis result of the frequency fluctuation time-series by means of the peak detection method of the heart-part oscillation wave of the subjects of the sleep introduction experiment B.
Figure 58:
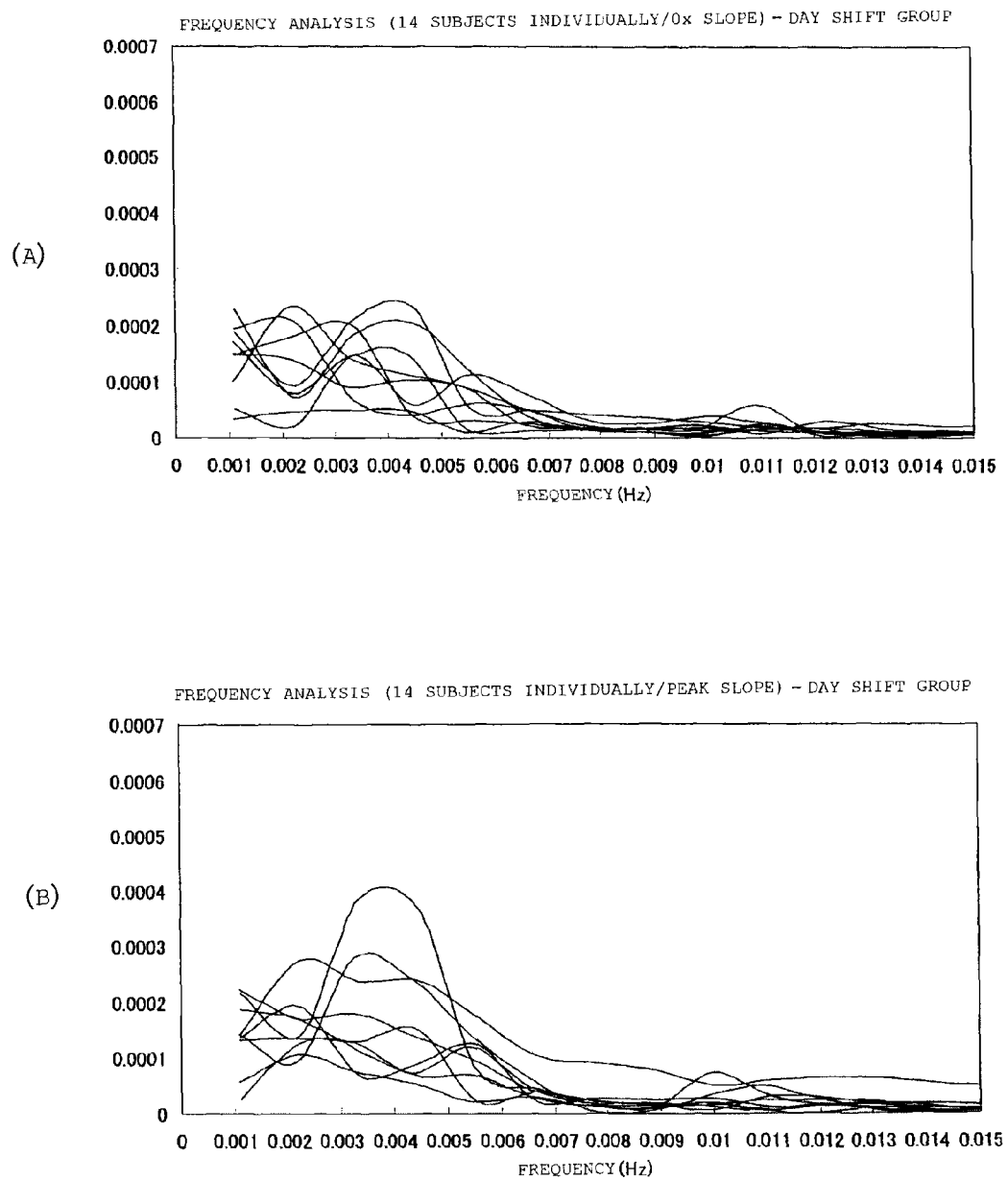
FIGS. 58(A) and 58(B) are diagrams illustrating the frequency analysis results of the frequency slope time-series by the zero-crossing method (A) and the peak detection method (B) of the heart-part oscillation wave of a day shift group of the sleep introduction experiment B.
Figure 59:
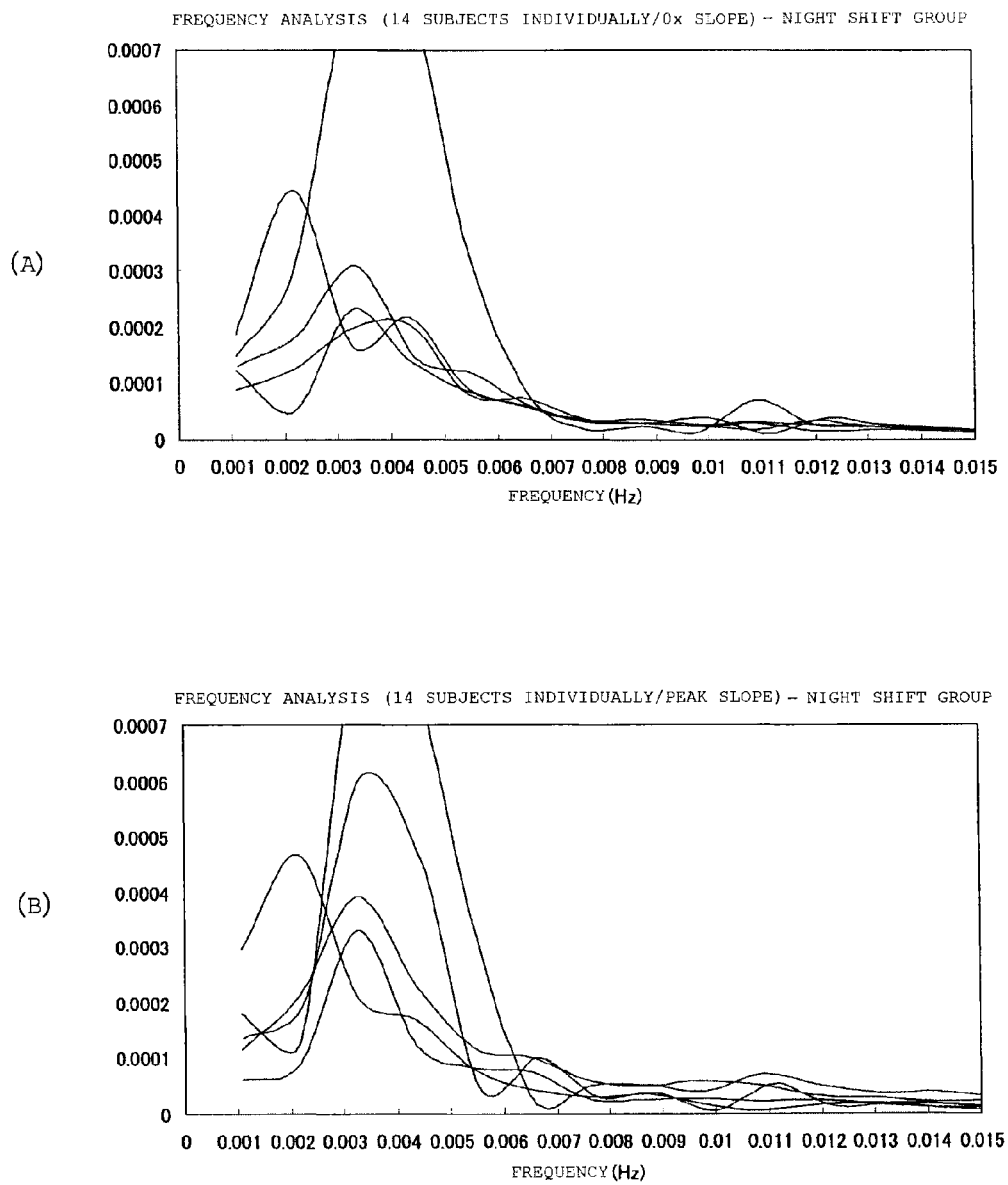
FIGS. 59(A) and 59(B) are diagrams illustrating the frequency analysis results of the frequency slope time-series by the zero-crossing method (A) and the peak detection method (B) of the heart-part oscillation wave of a night shift group of the sleep introduction experiment B.
Figure 60:
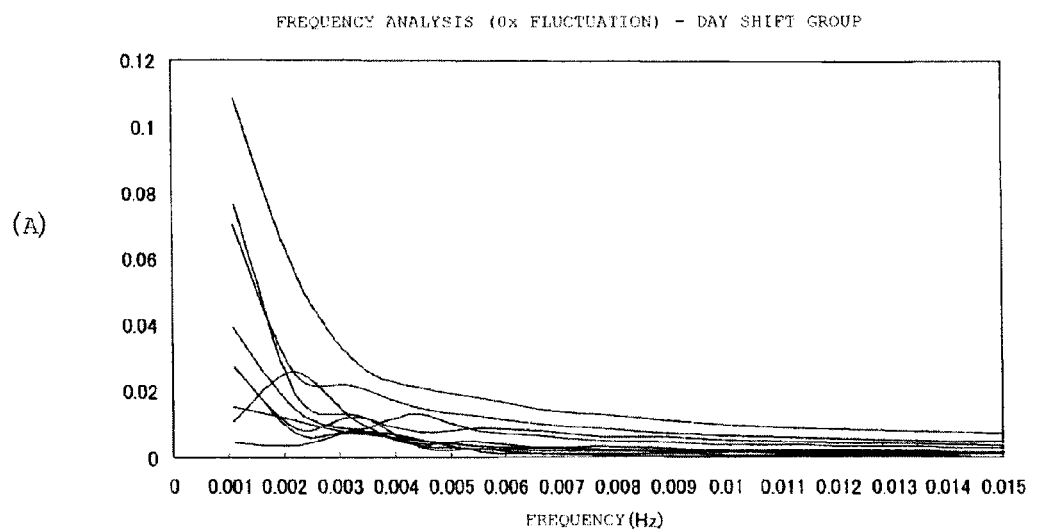
FIGS. 60(A) and 60(B) are diagrams illustrating the frequency analysis results of the frequency fluctuation time-series by the zero-crossing method (A) and the peak detection method (B) of the heart-part oscillation wave of the day shift group of the sleep introduction experiment B.
Figure 60:
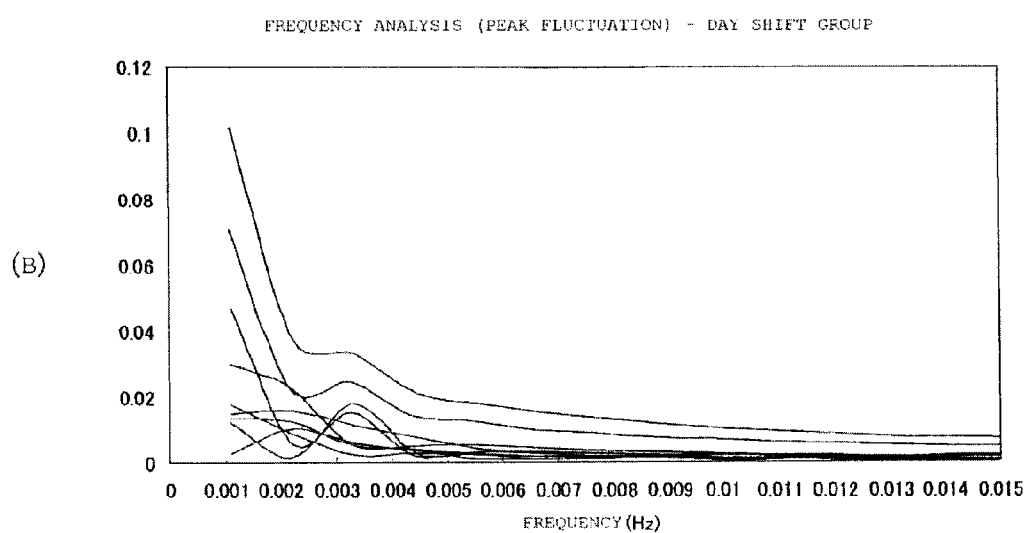
Figure 61:
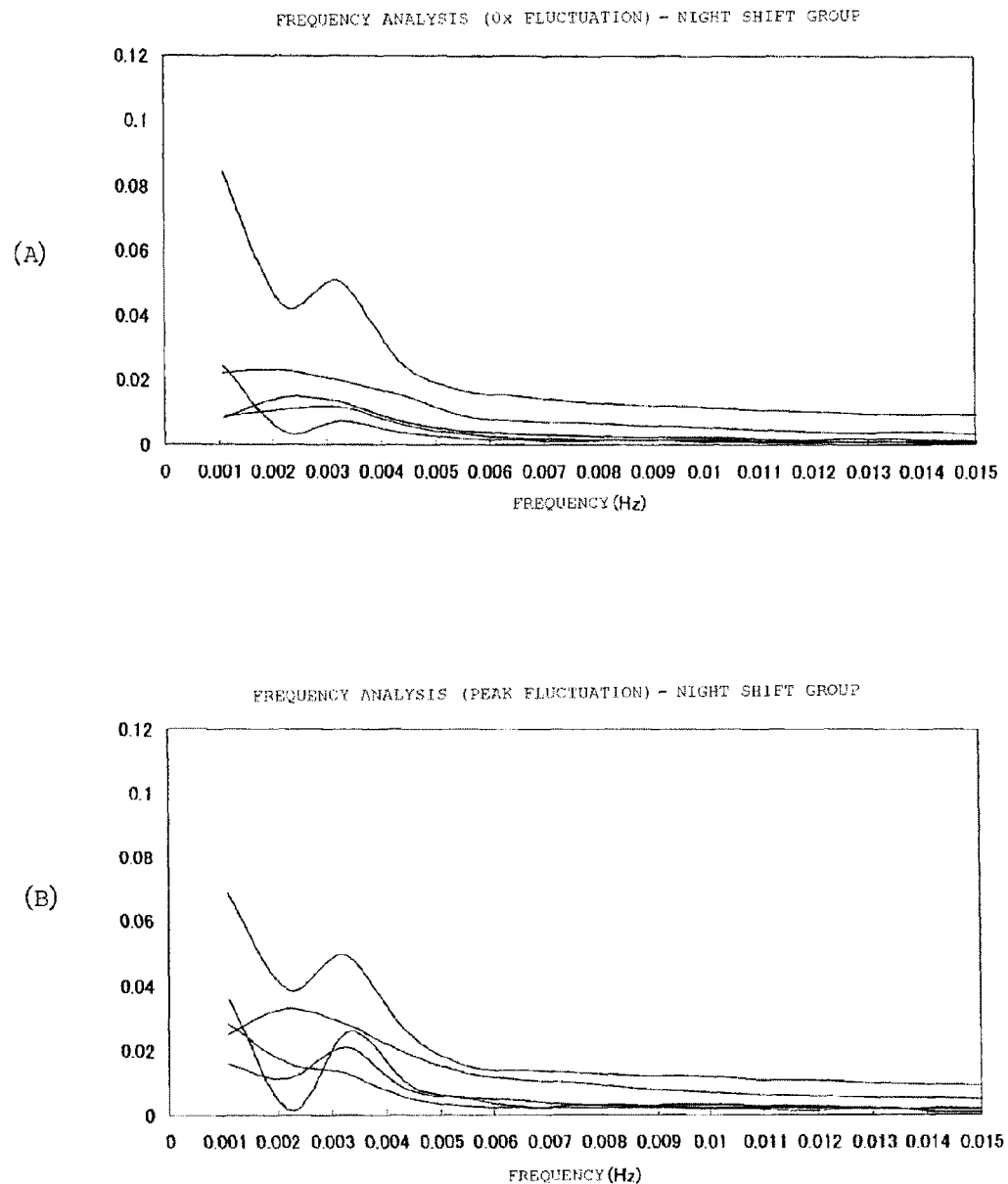
FIGS. 61(A) and 61(B) are diagrams illustrating the frequency analysis results of the frequency fluctuation time-series by the zero-crossing method (A) and the peak detection method (B) of the heart-part oscillation wave of the night shift group of the sleep introduction experiment B.
Figure 62:
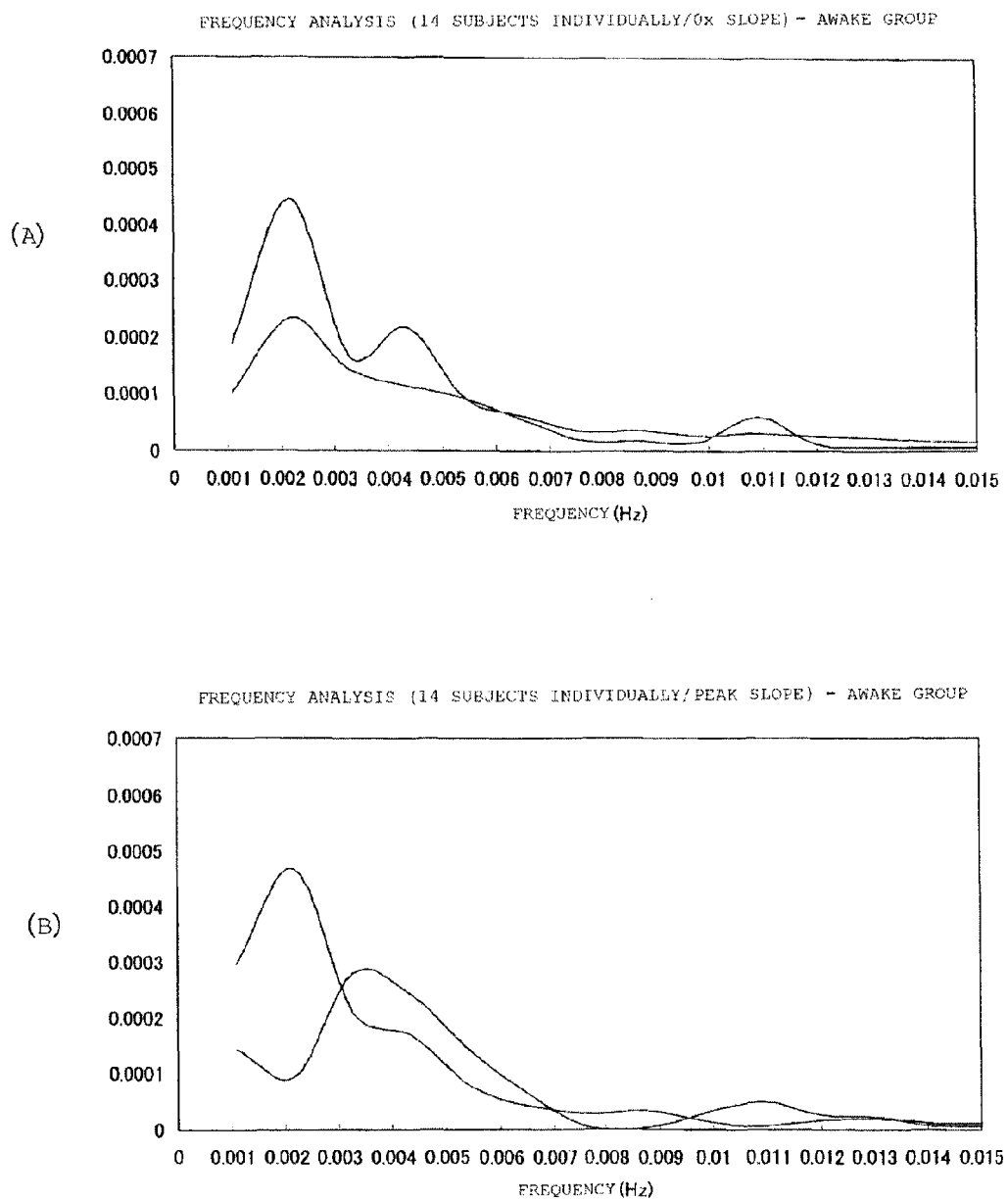
FIGS. 62(A) and 62(B) are diagrams illustrating the frequency analysis results of the frequency slope time-series by the zero-crossing method (A) and the peak detection method (B) of the heart-part oscillation wave of an awake group of the sleep introduction experiment B.
Figure 63:
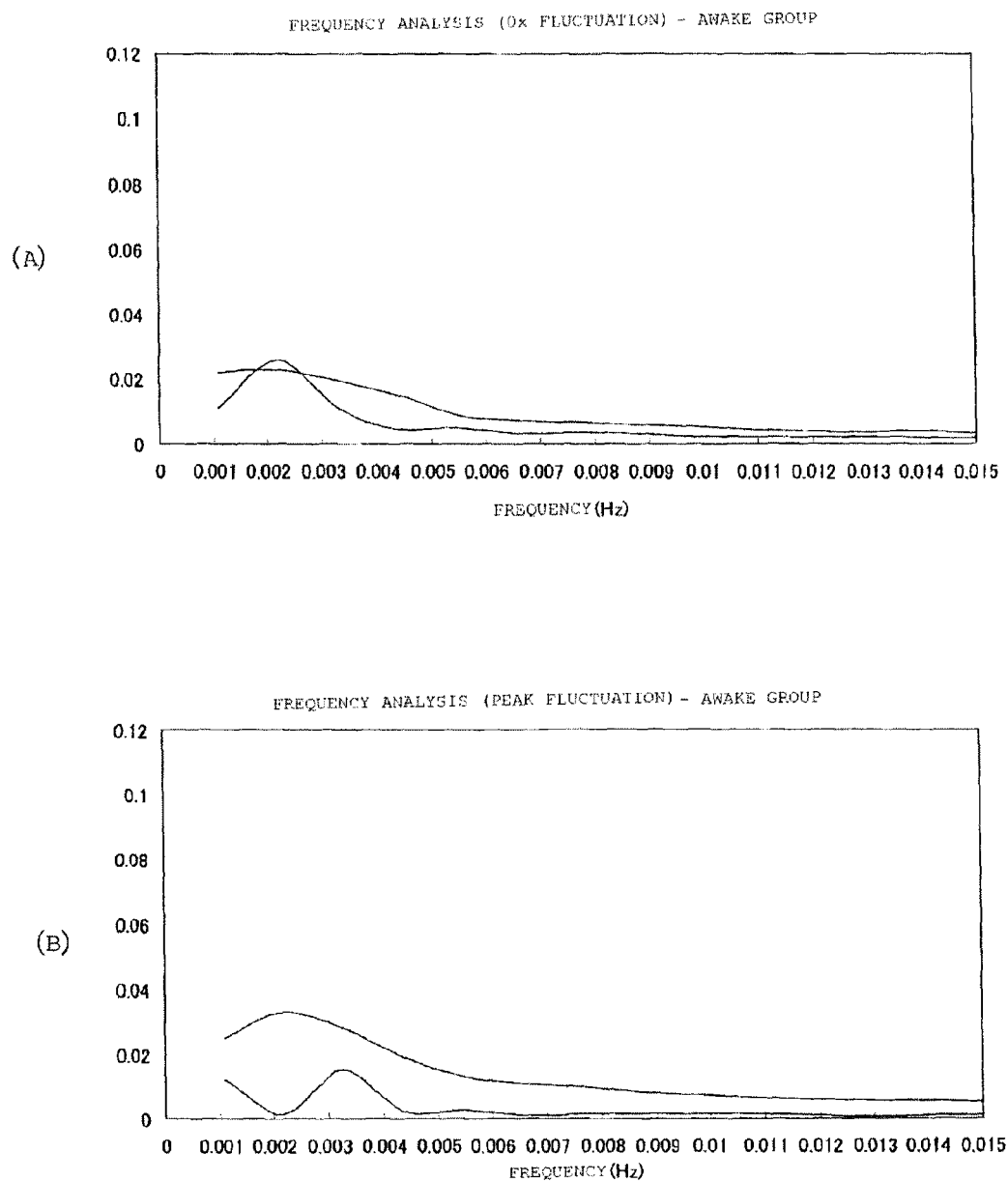
FIGS. 63(A) and 63(B) are diagrams illustrating the frequency analysis results of the frequency fluctuation time-series by the zero-crossing method (A) and the peak detection method (B) of the heart-part oscillation wave of the awake group of the sleep introduction experiment B.
Figure 64:
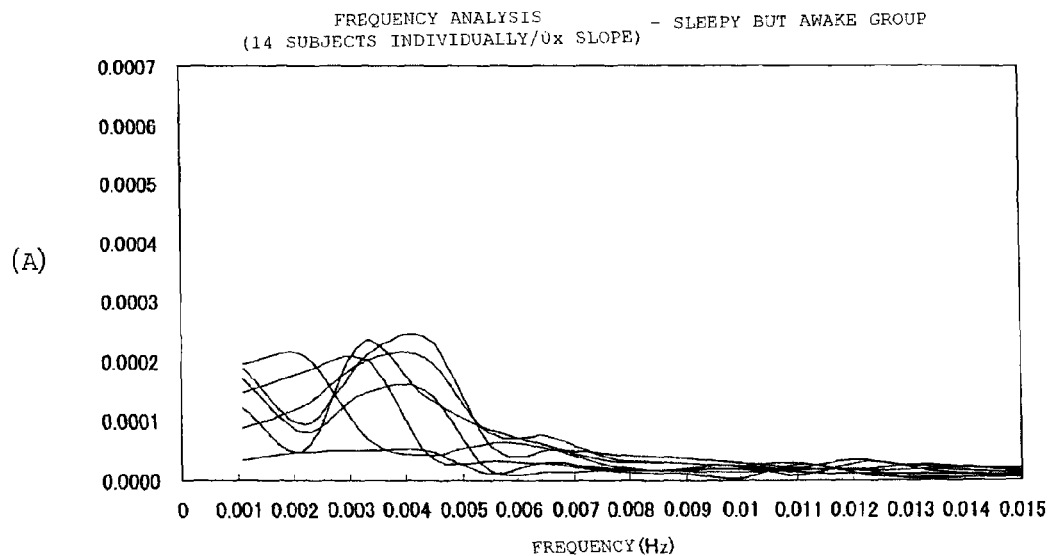
FIGS. 64(A) and 64(B) are diagrams illustrating the frequency analysis results of the frequency slope time-series by the zero-crossing method (A) and the peak detection method (B) of the heart-part oscillation wave of a sleepy but awake group of the sleep introduction experiment B.
Figure 64:
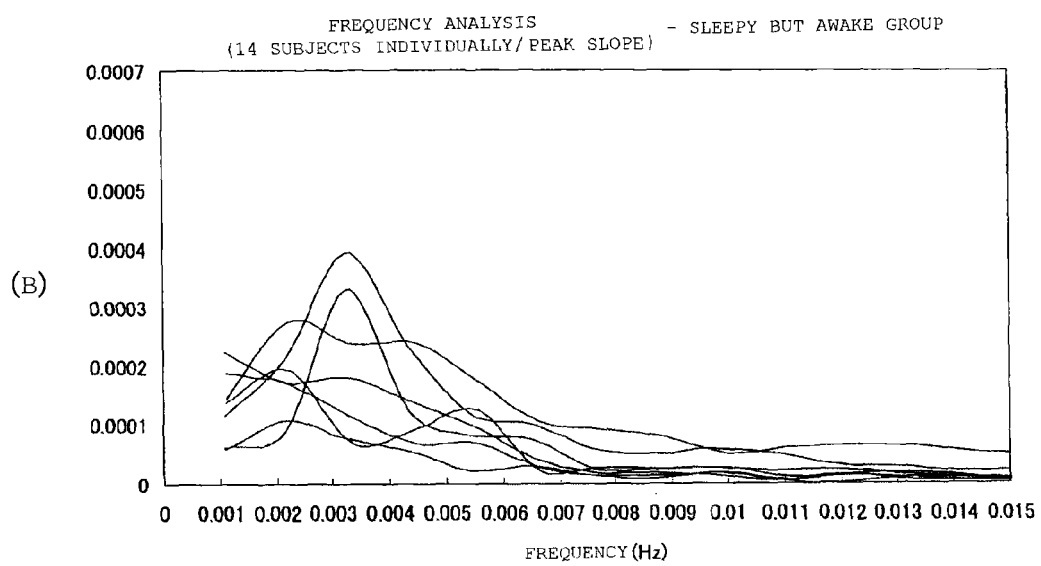
Figure 65:
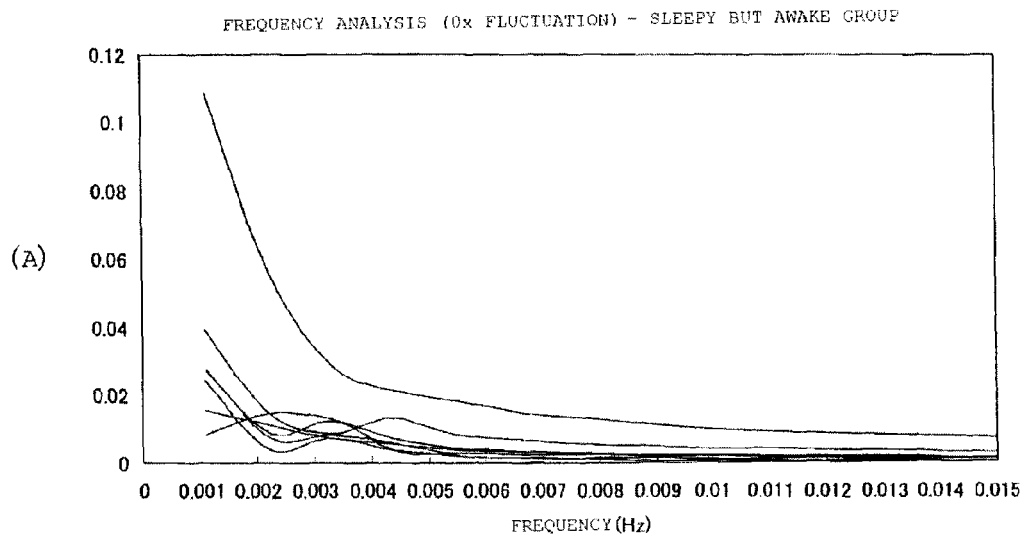
FIGS. 65(A) and 65(B) are diagrams illustrating the frequency analysis results of the frequency fluctuation time-series by the zero-crossing method (A) and the peak detection method (B) of the heart-part oscillation wave of the sleepy but awake group of the sleep introduction experiment B.
Figure 65:
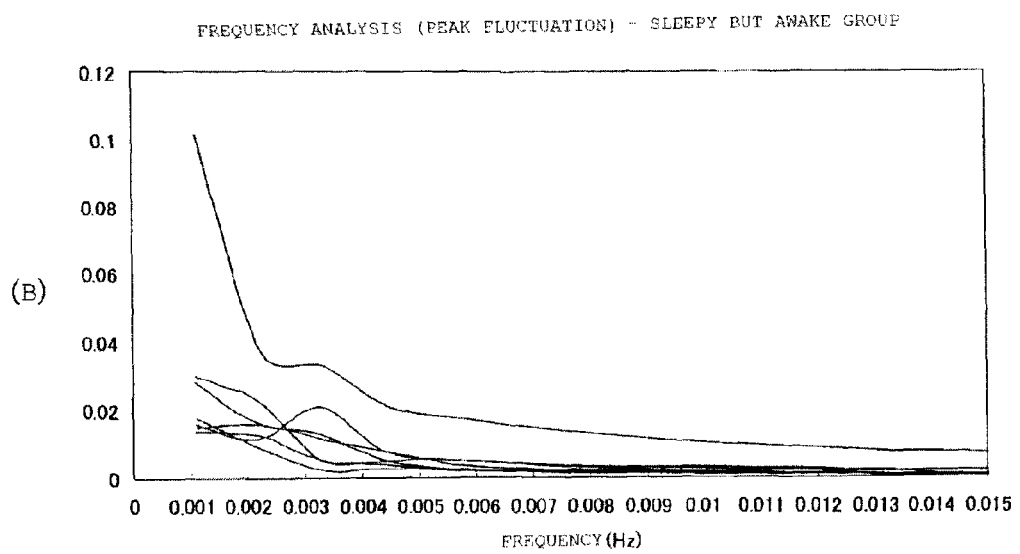
Figure 66:
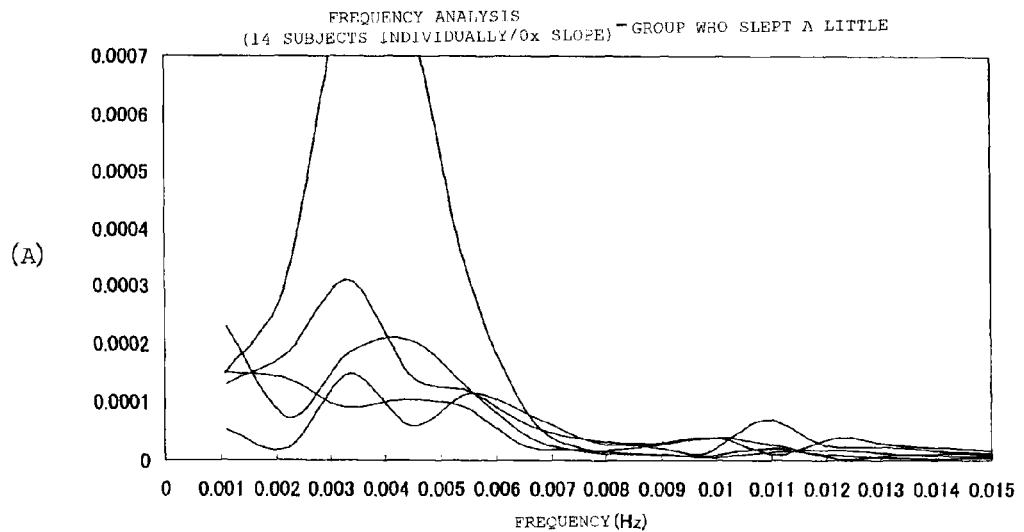
FIGS. 66(A) and 66(B) are diagrams illustrating the frequency analysis results of the frequency slope time-series by the zero-crossing method (A) and the peak detection method (B) of the heart-part oscillation wave of a group who slept a little of the sleep introduction experiment B.
Figure 66:
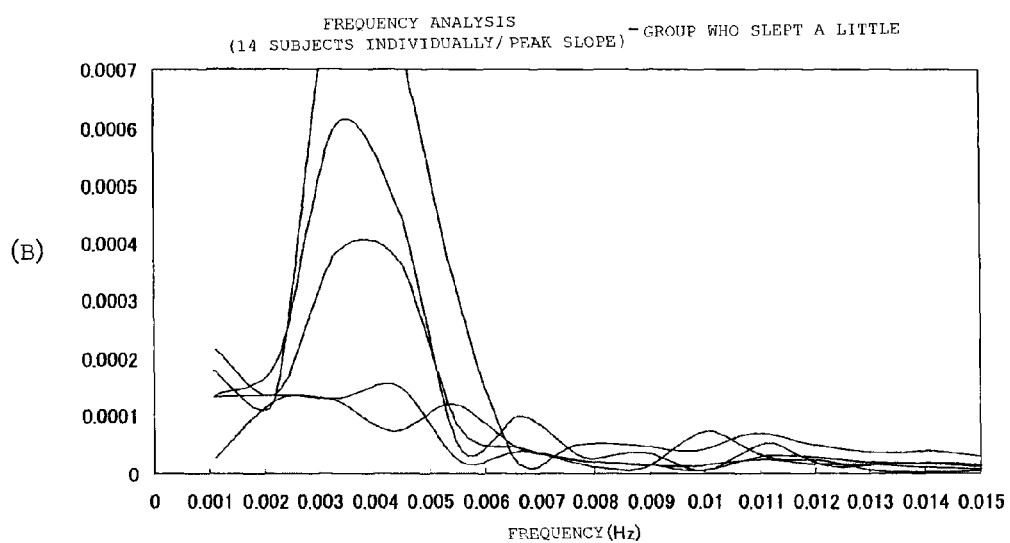
Figure 67:
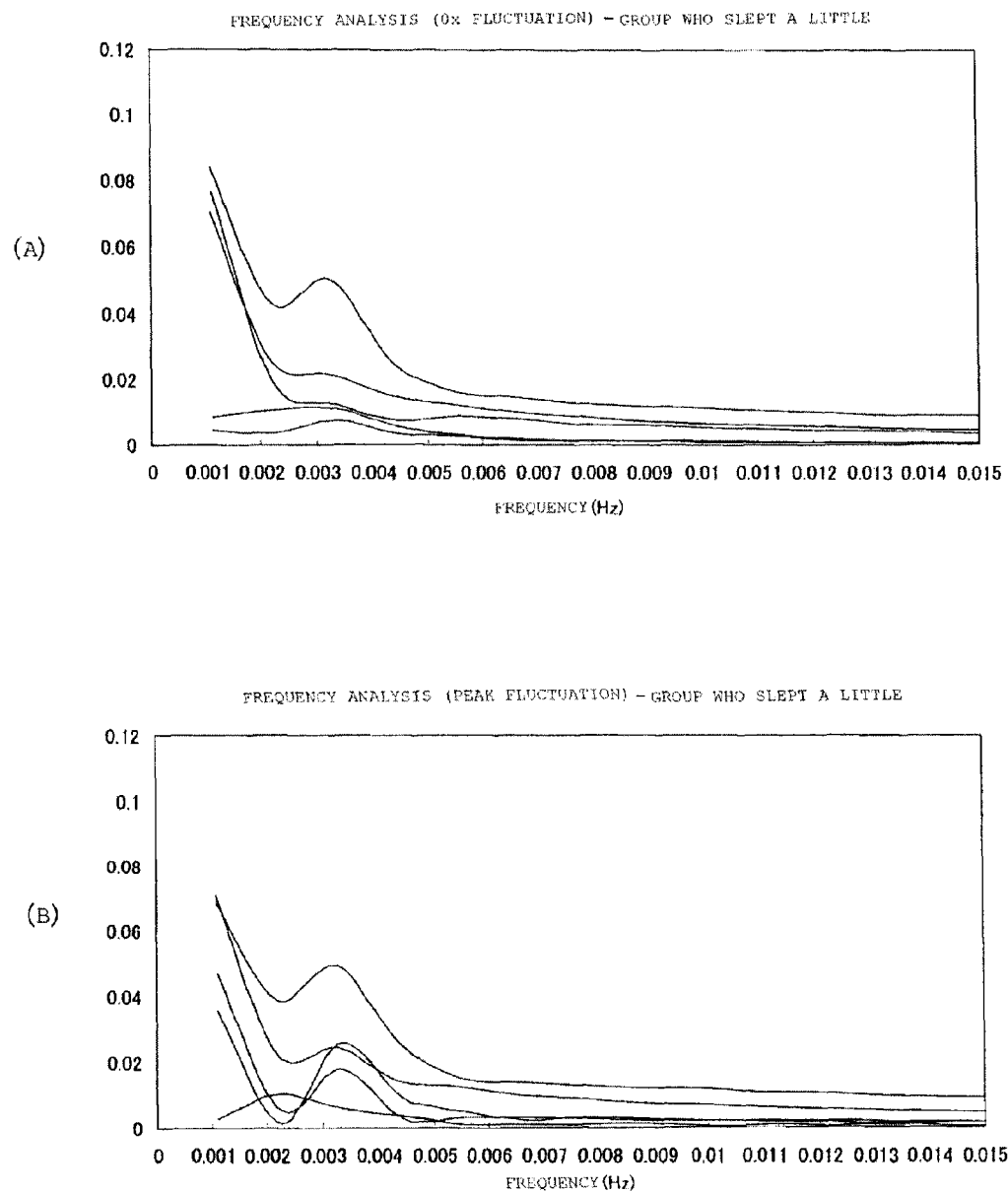
FIGS. 67(A) and 67(B) are diagrams illustrating the frequency analysis results of the frequency fluctuation time-series by the zero-crossing method (A) and the peak detection method (B) of the heart-part oscillation wave of the group who slept a little of the sleep introduction experiment B.

FIGS. 54 and 55 illustrate each frequency analysis result by the zero-crossing method and the peak detection method of the frequency slope time-series waveforms of the heart-part oscillation waves of the subjects of the sleep introduction experiment B. As compared with the subject groups of the sleep introduction experiment A, the width and fluctuation of the power spectrum fluctuation of 0.006 Hz or less are large. FIGS. 56 and 57 illustrate each frequency analysis result by the zero-crossing method and the peak detection method of the frequency fluctuation time-series waveform of the heart-part oscillation waves. Here, too, the width and fluctuation of the power spectrum fluctuation are large. FIGS. 58(A) and 58(B) and FIGS. 59(A) and 59(B) compare the frequency analysis results of the slope time-series waveforms by the zero-crossing method and the peak detection method of the heart-part oscillation waves according to groups of day shift subjects and night shift subjects, respectively. The power spectrum of the day shift subjects by the zero-crossing method is at 0.006 Hz or less and changes at 0.00025 or less, while in the peak detection method, though high mountains are partially found at 0.004 Hz, most of them are at 0.006 Hz or less and the power spectrum changes at 0.0003 or less. On the other hand, regarding the night shift subjects, the emerging frequency band tends to have a power spectrum larger than that of the day shift subjects in the low frequency. FIGS. 60(A) and 60(B) and FIGS. 61(A) and 61(B) illustrate each frequency analysis result by the zero-crossing method and the peak detection method of the frequency fluctuation time-series waveform according to the groups of the day shift subjects and the night shift subjects. Here, too, the night shift subjects tend to have a power spectrum larger than that of the day shift subjects on the whole.

FIGS. 62(A) and 62(B) and FIGS. 63(A) and 63(B) illustrate a frequency analysis result of the slope time-series waveform and frequency fluctuation by the zero-crossing method and the peak detection method of a group who were awake. Examining the slope time-series waveforms in FIGS. 62(A) and 62(B), the fluctuation width of the power spectrum is larger in the vicinity of 0.00179 Hz than the fluctuation in the vicinity of 0.00358 Hz and 0.00537 Hz.

FIGS. 64(A) and 64(B) and FIGS. 65(A) and 65(B) illustrate a frequency analysis result of the slope time-series waveform and the frequency fluctuation by the zero-crossing method and the peak detection method of a group who were sleepy but were awake. Probably due to resistance against sleepiness, the width of power spectrum fluctuation at 0.00179 Hz, 0.00358 Hz, and 0.00537 Hz by the zero-crossing method is small, and an absolute value of the power spectrum in each frequency band is as small as 0.0002 or less (FIG. 64(A)). However, with the peak detection method, the change in the power spectrum at 0.00358 Hz is large (FIG. 64(B)). The fluctuation in this area is considered to be caused by sleepiness.

FIGS. 66(A) and 66(B) and FIGS. 67(A) and 67(B) illustrate a frequency analysis result of the slope time-series waveform and the frequency fluctuation by the zero-crossing method and the peak detection method of a group who slept a little. The fluctuation of the power spectrum in the vicinities of 0.00179 Hz and 0.00537 Hz is small and the fluctuation width in the vicinity of 0.00358 Hz is larger than them, or all the power spectrums at 0.00179 Hz, 0.00358 Hz, and 0.00537 Hz are small (FIGS. 66(A) and 66(B)). These two extreme states of fluctuation are considered to be caused by sleepiness.

Figure 68:
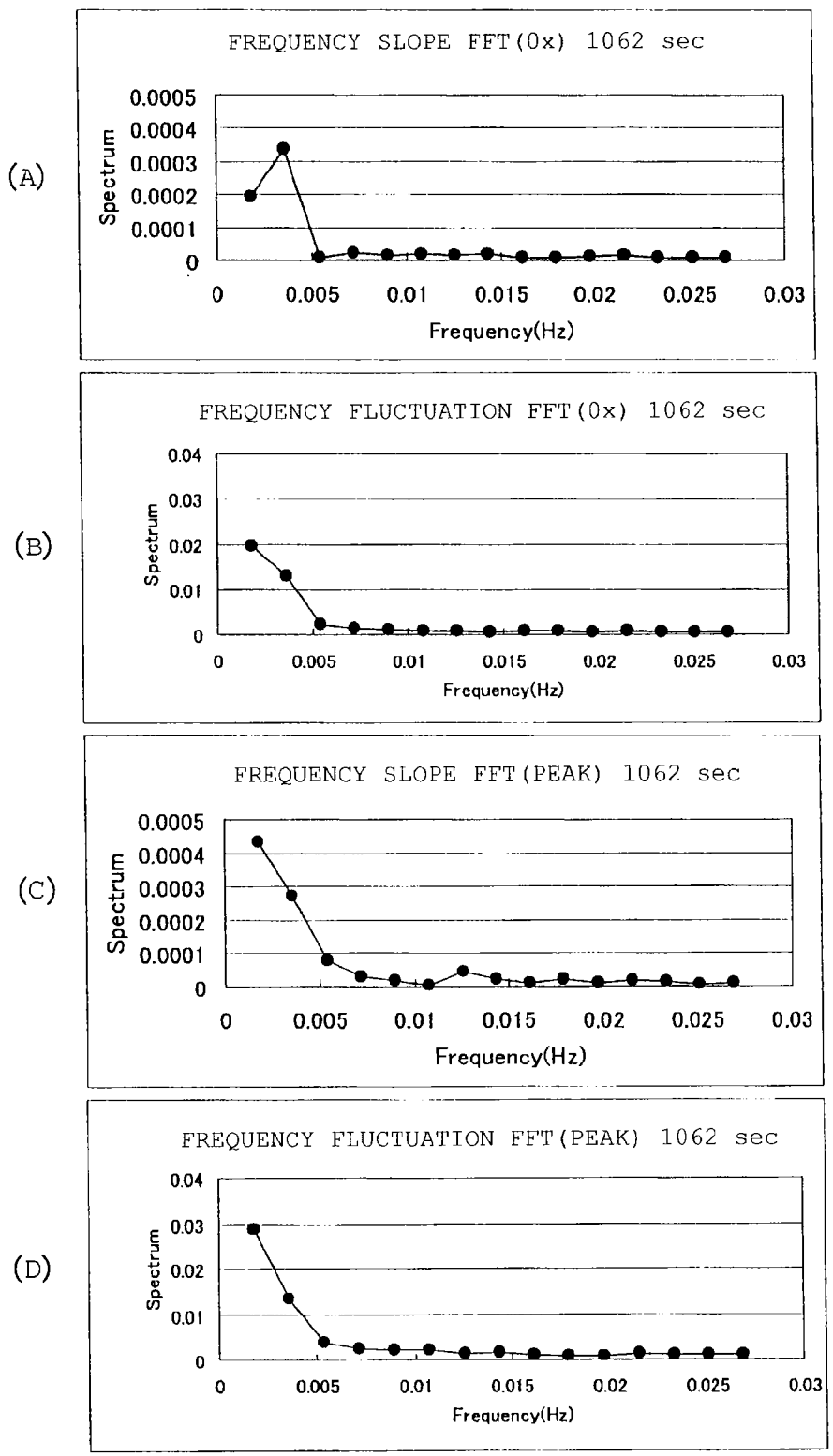
Figure 69:
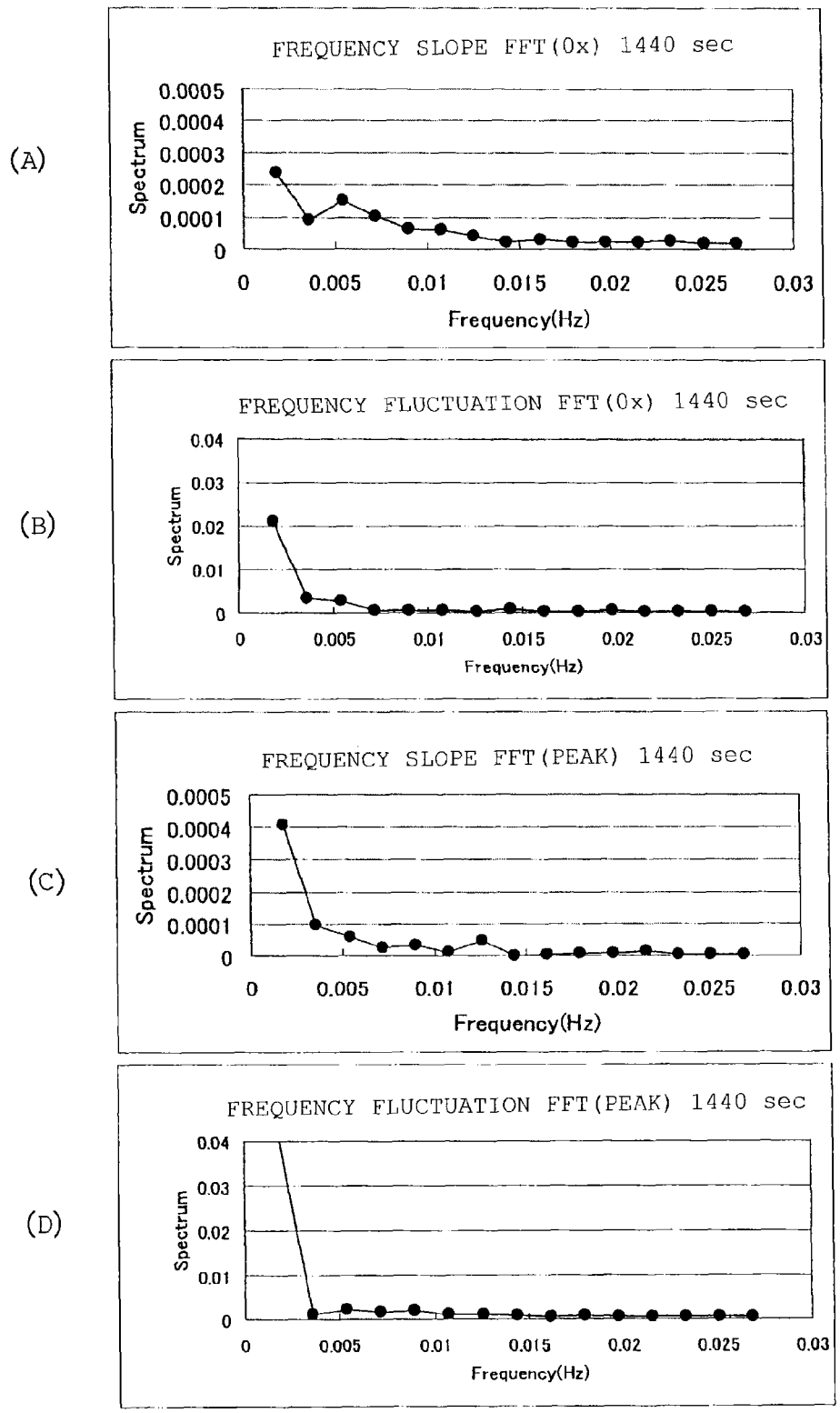
Figure 70:
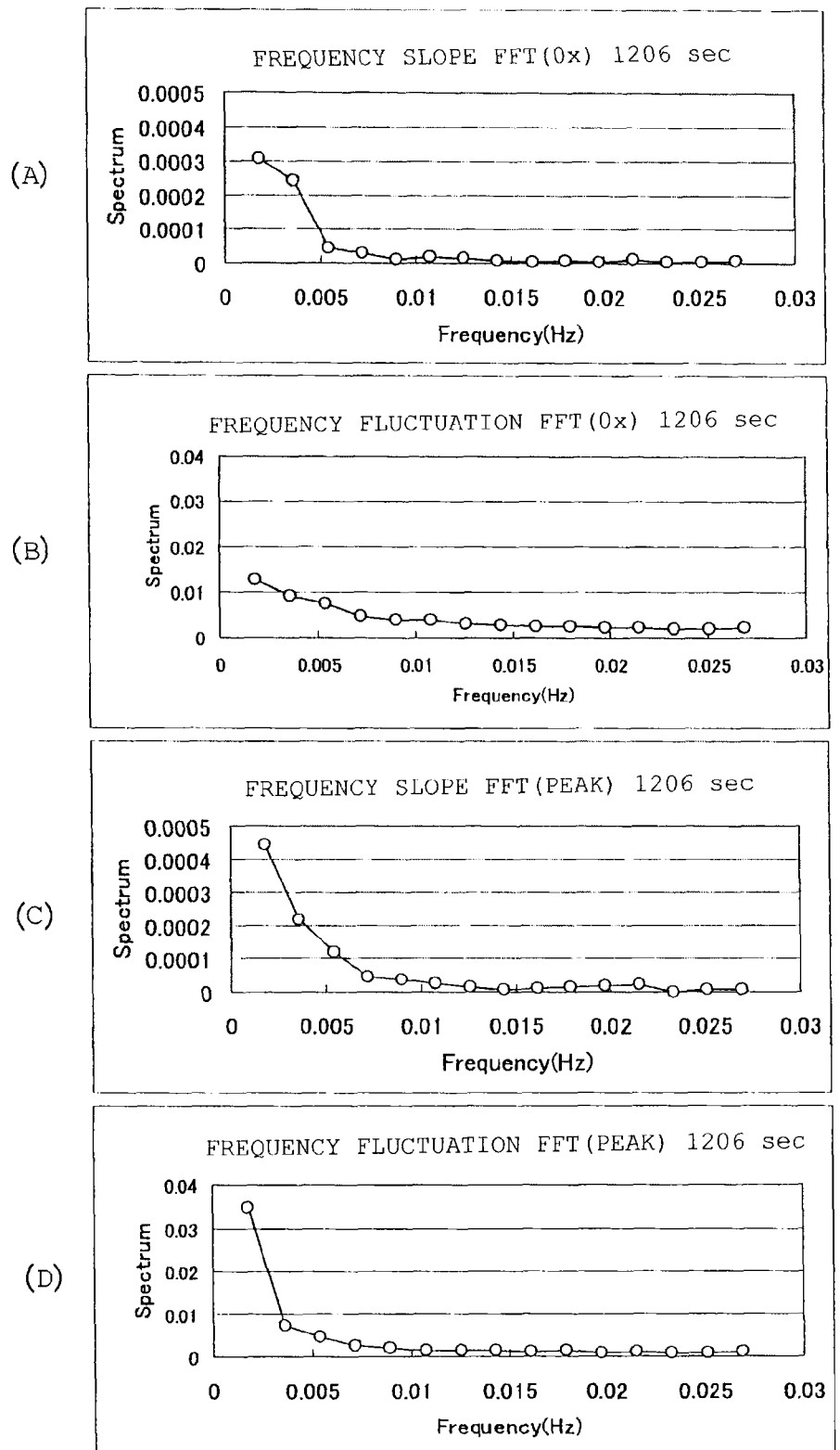
Figure 71:
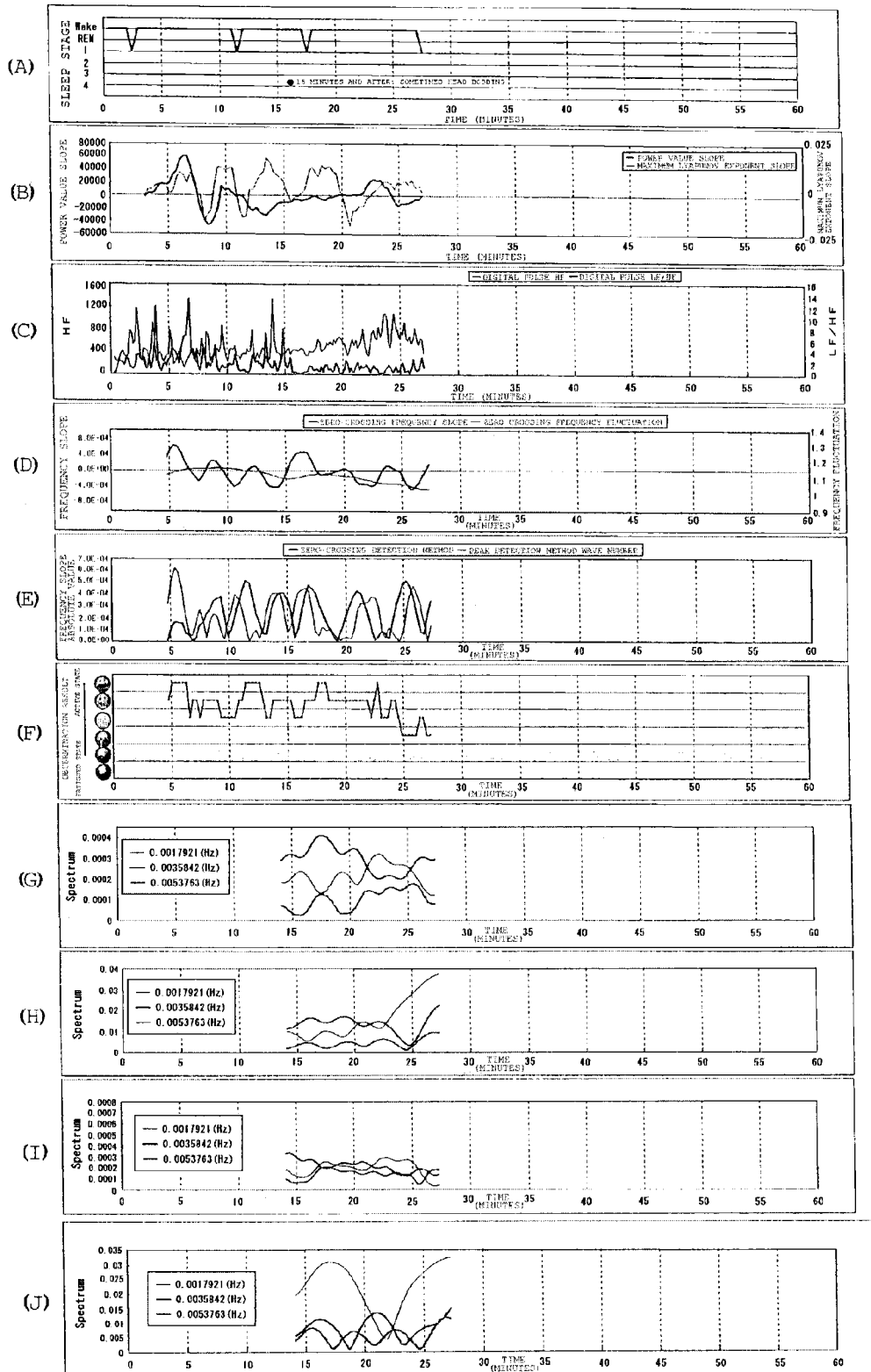
FIGS. 71(A) to 71(J) are diagrams illustrating experiment results of a subject (male in his 20's) in the sleep introduction experiment A.
Figure 72:
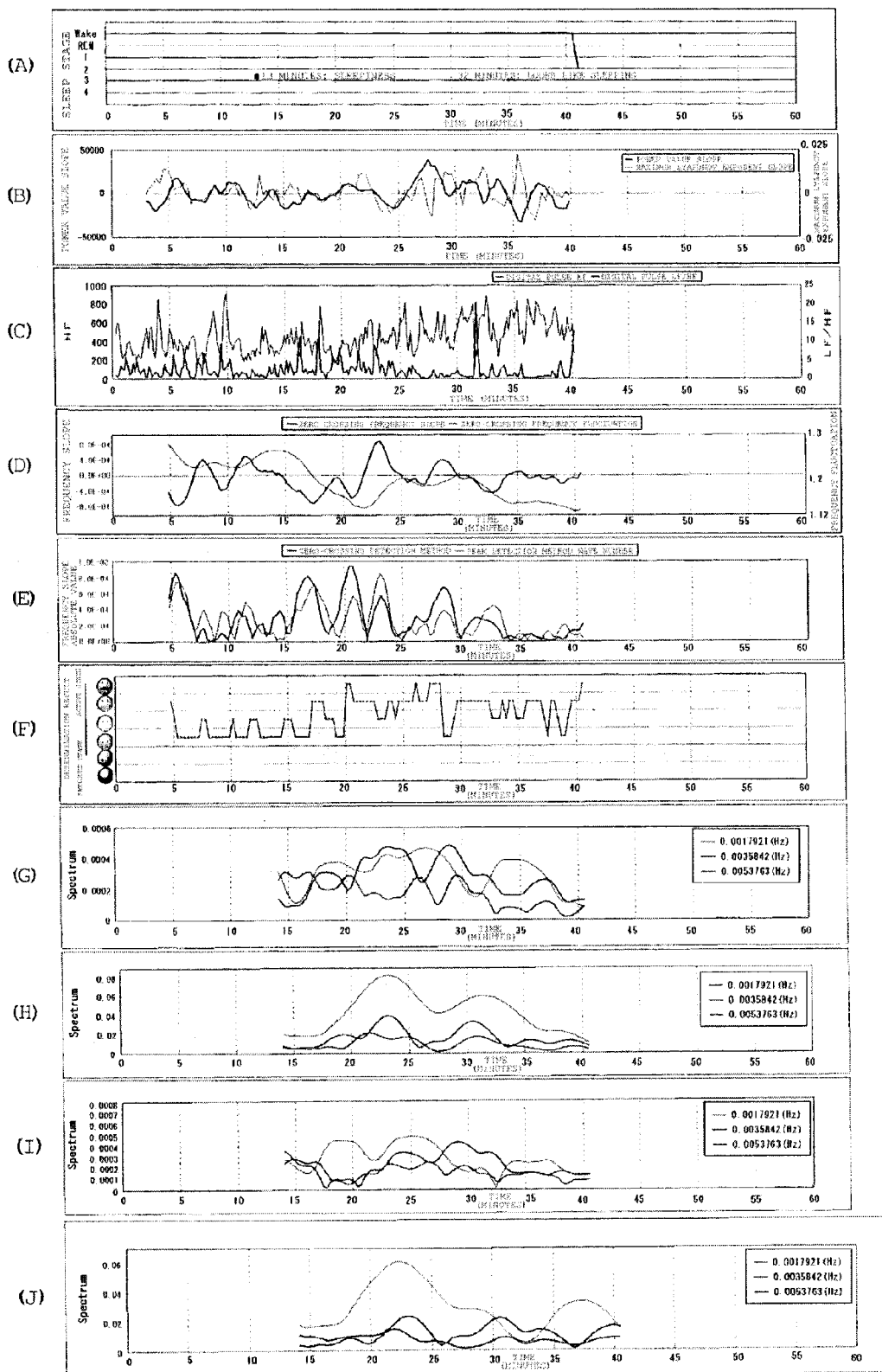
FIGS. 72(A) to 72(J) are diagrams illustrating experiment results of another subject (male in his 30's) in the sleep introduction experiment A.

Therefore, the fluctuation of the power spectrum at 0.00358 Hz of the slope time-series waveform by the zero-crossing method becomes larger if sleepiness occurs. The fluctuations at 0.00179 Hz of the frequency fluctuation time-series waveforms by the zero-crossing method and the peak detection method become larger, while the power spectrums at 0.00358 Hz and 0.00537 Hz become smaller. In the wakeful state, it is considered that the power spectrum stably and actively fluctuates among the three standard frequencies so as to maintain homeostasis. The change at emergence of the sleep prediction phenomenon is considered to have two types of states. By summarizing the experiments above, as illustrated in FIGS. 68 to 70, it is considered that there are a basic pattern at emergence of sleepiness and two types of patterns at emergence of the sleep prediction phenomenon. When the state progresses from emergence of sleepiness to emergence of the sleep prediction phenomenon, one of them is resistance against sleepiness and the other is acceptance of sleepiness. They show different changes. The former has a large power spectrum at 0.00179 Hz and 0.00537 Hz, while the power spectrum at 0.00358 Hz is small (See FIG. 69(A)). The latter has a large power spectrum at 0.00179 Hz and 0.00358 Hz, while the power spectrum at 0.00537 Hz is small (See FIG. 70(A)). Moreover, the power spectrum at 0.00179 Hz of the frequency fluctuation time-series waveform is large both in the zero-crossing method and the peak detection method (See FIGS. 68 to 70). Furthermore, an extreme difference occurs at 0.00179 Hz and 0.00358 Hz for the night shift subjects (See FIG. 59), which suggests a possibility that disturbance in circadian rhythm lowers control capabilities of these two frequency bands.

From the above results, it can be understood that the signal of 0.00179 Hz has a waveform fluctuating when the state largely changes or when the function deteriorates (functional adjustment signal), a signal of 0.00358 Hz is a frequency band fluctuating when fatigue progresses in a usual state (fatigue reception signal), and a signal of 0.00537 Hz is a signal which tends to fluctuate in an active state or when the function is in an activated state (activity adjustment signal). Subsequently, a verification test of identification of sleepiness and the sleep prediction phenomenon will be described by comparing a time-series change of the distribution rate using a ratio of power spectrums of these three standard frequencies and a prior-art medical index.

(Test Result)

FIGS. 71 to 92 are diagrams illustrating results of the 22 subjects in total in the sleep introduction experiment A, in which each of (G) to (I) in FIGS. 71 to 92 is an output result by the biological signal estimation device 60. Each (G) in FIGS. 71 to 92 illustrates a time-series change of the distribution rate corresponding to the functional adjustment signal, the fatigue reception signal, and the activity adjustment signal obtained by the power spectrum calculating means 670 by using the first frequency slope time-series waveform employing the zero-crossing (0×) method, each (H) in FIGS. 71 to 92 illustrates a time-series change of the distribution rate corresponding to the functional adjustment signal, the fatigue reception signal, and the activity adjustment signal obtained by the power spectrum calculating means 670 by using the first frequency fluctuation time-series waveform employing the zero-crossing (0×) method, each (I) in FIGS. 71 to 92 illustrates a time-series change of the distribution rate corresponding to the functional adjustment signal, the fatigue reception signal, and the activity adjustment signal obtained by the power spectrum calculating means 670 by using the second frequency slope time-series waveform employing the peak detection method, and each (J) in FIGS. 71 to 92 illustrates a time-series change of the distribution rate corresponding to the functional adjustment signal, the fatigue reception signal, and the activity adjustment signal obtained by the power spectrum calculating means 670 by using the second frequency fluctuation time-series waveform employing the peak detection method.

Each (A) in FIGS. 71 to 92 illustrates an output result of sleep depth of an electroencephalograph, and the diagram in each (B) illustrates a slope time-series waveform of the power value of the digital volume pulse and a slope time-series waveform of the maximum Lyapunov exponent. The diagram of each (B) is used when determining the sleep prediction phenomenon if the slope time-series waveform of the power value described in Patent Literature 1 proposed by the applicant of this application and the slope time-series waveform of the maximum Lyapunov exponent emerge in the opposite phase state. The diagram in each (C) illustrates a time-series waveform of the power spectrum of LF/HF which is an index of the sympathetic nerve acquired from the digital volume pulse and the time-series waveform of the power spectrum of HF which is an index of the parasympathetic nerve. This is a technology disclosed in Japanese Patent Laid-Open No. 2008-264138 by the applicant of this application, which is used when determining the sleep prediction phenomenon by emergence of a burst wave (a waveform of a temporary rising change) of the sympathetic nerve (LF/HF). The diagram in each (D) illustrates the above-described first frequency slope time-series waveform and the first frequency fluctuation time-series waveform obtained by processing the biological signal obtained by the biological signal measuring means 1 using the zero-crossing method. The diagram in each (E) illustrates a result of absolute value processing of the first frequency slope time-series waveform by using the zero-crossing method and the second frequency slope time-series waveform obtained by using the peak detection method, respectively.

Moreover, the diagram of each (F) in FIGS. 71 to 92 is based on the technology of Japanese Patent Application No. 2009-237802 previously proposed by the applicant of this application and a graph illustrating a comprehensive determination result of a state of a human being by combining the sign of the first frequency slope time-series waveform using the zero-crossing method, the sign of the integral waveform obtained by integrating the first frequency slope time-series waveform, comparison of absolute values of the frequency slope time-series waveforms obtained by absolute-value processing of the first frequency slope time-series waveform using the zero-crossing method and the second frequency slope time-series waveform using the peak detection method, respectively, emergence of an opposite phase if the first frequency slope time-series waveform and the first frequency fluctuation time-series waveform are outputted in a superposed manner (emergence of the opposite phase indicates sleep prediction) and the like. Three stages on the upper side on the vertical axis are states in which fatigue is felt, indicating a tensed state, a neutral state, and a relaxed state (active state), respectively, and three stages on the lower side are states in which a replacement compensation action is functioning, and the stages indicates higher fatigue degree (fatigued state) and lower concentration towards the lower stages. The signs of the positive and negative integral waveforms of the frequency slope time-series waveforms, comparison of the absolute values and the like are set integrally with a functional evaluation of a large number of subjects on a condition under which fatigue is felt or relaxation is felt and the like.

(Consideration)

The diagrams in (A) to (F) in FIGS. 71 to 92 illustrate determination results of a state of a human being by using the electroencephalograph and by the technology previously proposed by the applicant of this application. Whether or not the determination results by them match the determination results using (G) to (I) in FIGS. 71 to 92 which are test results of the present invention will be examined. In the diagram in (A), the state of the subject by an observer is also described.

In the diagram of each (G), it is examined whether the functional adjustment signal (0.00179 Hz) shows a rising tendency or not while the fatigue reception signal (0.00358 Hz) shows a lowering tendency, and if the condition is met, it is determined to be the "sleepiness-related phenomenon emergence period". Moreover, in the diagram of each of (H) to (I), whether or not the functional adjustment signal (0.00179 Hz) shows a rising tendency will be also examined.

FIG. 71

In (G), the fatigue reception signal markedly lowers in the vicinity of 21 to 23 minutes, and since a rising tendency of the functional adjustment signal is found in that time zone, it is determined to be the sleepiness-related phenomenon emergence period. In (H) to (I), a rapid rising tendency of the functional adjustment signal is observed.

On the other hand, the sleep stage 1 was reached at around 17 minutes in (A), but a burst wave of the sympathetic nerve indicating sleep prediction occurred at about 15 minutes in (C). As illustrated in (A), an observation result describes that the head of the subject was sometimes bobbing at 15 minutes and after. Moreover, the subject slept instantaneously at about 27 minutes and a sleep prediction signal is found at about 25 minutes in (B).

Thus, the identification of the sleepiness-related phenomenon emergence period using the method of the present invention from (G) to (J) can be considered to capture the sleep prediction phenomenon which is a sign of instantaneous sleep at about 27 minutes, and the determination is valid.

FIG. 72

In (G), the fatigue reception signal markedly lowers in the vicinity of 29 to 35 minutes, and since a rising tendency of the functional adjustment signal is found at 32 minutes and after, it is determined that sleepiness was felt at around 30 minutes and the subject entered the sleepiness-related phenomenon emergence period. Moreover, in (H) to (J), a rise of the functional adjustment signal is also shown in that time zone.

On the other hand, in (B), a signal indicating the sleep prediction phenomenon of an opposite phase, large amplitude, and a long period emerged at about 25 to 37 minutes, a burst wave occurred at about 32 minutes in (C), and a fall over 2 stages or more of the index indicating a rapid change on an energy level is found at about 28 to 29 minutes in (F). As illustrated in (A), the observation result describes that the subject looked like sleeping at about 32 minutes.

Thus, the determination of the sleepiness-related phenomenon emergence period using the method of the present invention is reasonably valid.

FIG. 73

In (G), the fatigue reception signal markedly lowers in the vicinity of 35 to 40 minutes, and since a rising tendency of the functional adjustment signal is found in that time zone, it is determined that sleepiness was felt at around 35 minutes and the subject entered the sleepiness-related phenomenon emergence period. Moreover, in (H) and (J), too, a rise of the functional adjustment signal is shown in that time zone.

On the other hand, in (B), states of an opposite phase, large amplitude, and a long period of two time-series waveforms indicating the sleep prediction phenomenon emerged at about 27 to 35 minutes, in (C), a burst wave occurred at about 23 to 24 minutes, and in (F), too, a fall over 2 stages or more of the index is found at about 36 minutes. As illustrated in (A), the observation result describes that the subject looked like sleeping at about 32 minutes.

Thus, the determination of the sleepiness-related phenomenon emergence period by using the method of the present invention is reasonably valid.

FIG. 74

In (G), the fatigue reception signal steeply lowers in the vicinity of 25 to 30 minutes, the lowered state is maintained after that, the fatigue reception signal further markedly lowers in the vicinity of 37 to 42 minutes, and since a rising tendency of the functional adjustment signal is found in that time zone, it is determined that sleepiness was felt at around 25 minutes and the subject entered the sleepiness-related phenomenon emergence period. Moreover, in (H) and (J), too, a rise of the functional adjustment signal is shown in that time zone, and thus, the sleep prediction phenomenon is considered to be captured here.

On the other hand, in (A), the subject reaches the sleep stage 2 at 35 minutes and after. As illustrated in (A), the observation result describes that the head was bobbing at about 32 minutes, the head tilted backward at 36 minutes, and the subject looked like sleeping at 39 minutes. It is determined that in (E), the subject was in a state where the parasympathetic nerve was predominant at 25 minutes and after, and the parasympathetic nerve was also still predominant at 30 minutes and after, and in (F), the sleepiness emerged at about 25 minutes, the subject resisted the sleepiness but could not resist any longer at 30 minutes and after.

Thus, the determination of the sleepiness-related phenomenon emergence period by using the method of the present invention is reasonably valid.

FIG. 75

In (G), the marked fall of the fatigue reception signal and the rising tendency of the functional adjustment signal in that period are not found, thus it is determined that the sleepiness-related phenomenon emergence period does not occur. The result matches the observation result that "could not sleep" in (A), and the determination using the method of the present invention is reasonably valid.

FIG. 76

In (G), the fatigue reception signal markedly lowers a number of times in the vicinity of 26 to 42 minutes, and since a rising tendency of the functional adjustment signal is found in that time zone, it can be determined that sleepiness was felt at around 26 minutes and after and the subject entered the sleepiness-related phenomenon emergence period. Moreover, in (H) and (J), too, a rise of the functional adjustment signal is shown in that time zone.

On the other hand, in (A), the sleep stages 2, 3, and 1 intermittently occur at 24 minutes and after, and the observation result describes that the subject fell asleep at about 33 minutes, woke up once at 41 minutes and then, fell asleep again. In (F), too, a fall over 2 stages of the index occurs in the vicinity of 33 minutes and then, at about 39 minutes and 41 minutes and the like, the index rapidly lowers. In (D), states of an opposite phase, large amplitude, and a long period occurred at about 20 minutes, in (C), a burst wave occurred at 16 and 17 minutes, and in (E), the state in which the sympathetic nerve is predominant at 20 minutes after the parasympathetic nerve became predominant at 16 minutes occurs, all of which indicate the sleep prediction phenomenon.

Thus, the determination of the sleepiness-related phenomenon emergence period by using the method of the present invention is reasonably valid.

FIG. 77

In (G), the fatigue reception signal markedly lowers in the vicinity of 24 to 31 minutes and in the vicinity of 33 to 37 minutes, and since a rising tendency of the functional adjustment signal is found in that time zone, it can be determined that the subject entered the sleepiness-related phenomenon emergence period in those time zones. Moreover, in (H) and (J), a rise of the functional adjustment signal is found at 35 minutes and after, while in (J), a rise of the functional adjustment signal is found at 27 to 30 minutes.

On the other hand, in (B), states of an opposite phase, large amplitude, and a long period indicating the sleep prediction phenomenon emerged at about 10 minutes, and in (C), a burst wave indicating the sleep prediction phenomenon emerged at about 10 minutes. In (F), a rapid fall of the index is found in the vicinity of 20 minutes. In (A), the subject intermittently entered the sleep stage 1 in the vicinity of 23 to 30 minutes and in the vicinity of 35 to 42 minutes.

Thus, the determination of the sleepiness-related phenomenon emergence period by using the method of the present invention is reasonably valid.

FIG. 78

In (G), the fatigue reception signal markedly lowers in the vicinity of 28 to 33 minutes, and since a rising tendency of the functional adjustment signal is found in that time zone, it can be determined that the subject entered the sleepiness-related phenomenon emergence period in that time zone. Moreover, in (H) to (J), too, a rise of the functional adjustment signal is found in that time zone.

On the other hand, in (B), it can be identified that the sleep prediction phenomenon occurred in the vicinity of 27 to 30 minutes. In (C), a burst wave occurred at 23 minutes, and in (F), the index rapidly fell at 20 minutes and 24 minutes. The observation result describes that the subject looked sleepy from the start of the experiment to 30 minutes and awakened at 30 minutes. However, the measurement result of the brain wave in (A) does not capture this phenomenon.

Thus, the determination of the sleepiness-related phenomenon emergence period using the method of the present invention is reasonably valid, and the phenomenon that could not be identified by an electroencephalograph due to occurrence of noise can be also captured.

FIG. 79

In (G), the fatigue reception signal markedly lowers in the vicinity of 35 to 44 minutes, and since a rising tendency of the functional adjustment signal is found in that time zone, it can be determined that the subject entered the sleepiness-related phenomenon emergence period in that time zone. Moreover, in (H) to (J), too, a rise of the functional adjustment signal is found in that time zone.

On the other hand, in (B), it can be identified that the sleep prediction phenomenon occurred in the vicinity of 32 to 35 minutes. In (C), a burst wave occurred at 27 minutes, and in (F), the index rapidly fell at 25 minutes. The observation result describes that the subject looked like sleeping at 37 minutes and was dozing at 39 minutes.

Thus, the determination of the sleepiness-related phenomenon emergence period by using the method of the present invention is reasonably valid.

FIG. 80

In (G), the fatigue reception signal markedly lowers in the vicinity of 27 to 32 minutes, and since a rising tendency of the functional adjustment signal is found in that time zone, it can be determined that the subject entered the sleepiness-related phenomenon emergence period in that time zone. Moreover, in (H) and (I), too, a rise of the functional adjustment signal is found in that time zone.

On the other hand, in (B), states of an opposite phase, large amplitude, and a long period indicating the sleep prediction phenomenon emerged in the vicinity of 10 to 20 minutes, and in (C), a burst wave indicating the sleep prediction phenomenon occurred at about 13 minutes. In (F), a rapid fall of the index is found in the vicinity of 27 minutes and 34 minutes. Thus, the determination of the sleepiness-related phenomenon emergence period using the method of the present invention seems to match (F). The observation result describes that the subject closed the eyes at 37 minutes and started to nod-off at about 40 minutes, and the determination of the sleepiness-related phenomenon emergence period is made at timing slightly earlier than the sign of sleepiness found in the observation result.

FIG. 81

In (G), the fatigue reception signal markedly lowers in the vicinity of 21 to 26 minutes and 33 to 36 minutes, and since a rising tendency of the functional adjustment signal is found in that time zone, it can be determined that the subject entered the sleepiness-related phenomenon emergence period in that time zone. Moreover, in (H), too, a rise of the functional adjustment signal is found in that time zone.

On the other hand, in (B), it can be identified that the sleep prediction phenomenon occurred in the vicinity of 20 to 24 minutes. In (C), a burst wave occurred at 12 minutes and 20 minutes. In (F), the index rapidly fell in the vicinities of 15 to 20, 29 and 34 minutes. The observation result describes that the subject momentarily slept at 22 minutes, the head was bobbing at 32 minutes, the head tilted backward at 33 minutes, and snored and slept at 34 minutes.

Thus, the determination of the sleepiness-related phenomenon emergence period by using the method of the present invention is reasonably valid.

FIG. 82

In (G), there is no time zone when a marked fall of the fatigue reception signal and a rise of the functional adjustment signal are both found at the same time. Thus, it is determined that the sleepiness-related phenomenon emergence period did not occur. In (F), a rapid change is found in the energy level at 34, 36, and 42 minutes. This fall in the energy level is an incidental phenomenon emerging when the sleep prediction phenomenon occurs and is not an inevitable phenomenon. This subject is considered to easily develop a state where the parasympathetic nerve is predominant, which does not necessarily match the determination result of (G).

However, the observation result describes that the subject rarely slept during the experiment, and as a result, the determination result using the method of the present invention is reasonably valid.

FIG. 83

In (G), the fatigue reception signal markedly lowers in the vicinity of 30 to 38 minutes, and since a rising tendency of the functional adjustment signal is found in that time zone, it can be determined that the subject entered the sleepiness-related phenomenon emergence period in that time zone. Moreover, in (H) to (J), too, a rise of the functional adjustment signal is found in that time zone.

On the other hand, in (C), a burst wave occurred at 12 minutes and at about 25 minutes. In (F), the index rapidly fell at 16, 17, 32, 36 and 38 minutes. The brain wave in (A) shows that after reaching the sleep stage 1 at 14 minutes, the subject entered the sleep stages 1 to 2 at 32 minutes and after. In (B), the sleep prediction phenomenon is found at about 10 minutes.

Thus, the determination of the sleepiness-related phenomenon emergence period by using the method of the present invention is reasonably valid.

FIG. 84

In (G), the fatigue reception signal markedly lowers in the vicinity of 37 to 42 minutes, and since a rising tendency of the functional adjustment signal is found in that time zone, it can be determined that the subject entered the sleepiness-related phenomenon emergence period in that time zone. In (H), there is a rise of the functional adjustment signal, and in (I) and (J), a rise of the functional adjustment signal is found at 41 to 42 minutes and after.

On the other hand, in (B), the sleep prediction phenomenon emerges at about 26 minutes, and in (F), a rapid fall of the energy level is intermittently found at 24 minutes and after. The subject commented that he lost consciousness at about 40 minutes and dozed off at 45 minutes and after. Therefore, the determination of the sleepiness-related phenomenon emergence period using the method of the present invention is reasonably valid.

FIG. 85

In (G), the fatigue reception signal markedly lowers in the vicinity of 20 to 27 minutes and in the vicinity of 35 to 42 minutes, and since a rising tendency of the functional adjustment signal is found in those time zones, it can be determined that the subject entered the sleepiness-related phenomenon emergence period in those time zones. In (H) and (J), too, a rise of the functional adjustment signal is found in those time zones.

On the other hand, in the brain wave in (A), the sleep stage 1 is intermittently reached until 30 minutes, and the sleep stages 1 and 2 are also reached at 35 minutes and after. In (C), a burst wave emerged in the vicinity of 21 minutes. In (F), a rapid fall of the index occurred in the vicinities of 27, 34, 38 minutes. The subject commented that he felt sleepy from the start of the experiment to 30 minutes, and the observation result describes that the head deeply tilted backward at 37 minutes.

Therefore, the sleepiness-related phenomenon in the first half identified by the method of the present invention can be considered to capture the period in which the subject resisted sleepiness, and the sleepiness-related phenomenon in the second half can be considered to capture the sleep prediction phenomenon before falling asleep.

Thus, the determination of the sleepiness-related phenomenon emergence period by using the method of the present invention is reasonably valid.

FIG. 86

In (G), the fatigue reception signal markedly lowers in the vicinity of 25 to 30 minutes, 37 to 42 minutes, and 48 to 50 minutes, and since a rising tendency of the functional adjustment signal is found in those time zones, it can be determined that the subject entered the sleepiness-related phenomenon emergence period in those time zones. The stable lowered state of the power spectrum in the distribution rate indicates that the subject entered the sleep state, the subject entered a deeper sleep at 40 to 45 minutes, changed to a shallow sleep at 48 to 50 minutes, and is considered to have awakened at 55 minutes. Moreover, in (H) and (J), too, a rise of the functional adjustment signal is found in those time zones.

On the other hand, from (B), it can be determined that the sleep prediction phenomenon occurred in a period from 10 to 35 minutes, and it can be determined that the sleepiness occurred and the subject proceeded into the sleep state at 38 minutes and after. In (C), a burst wave indicating the sleep prediction phenomenon emerged in the vicinity of 24 minutes. In (F), a rapid fall of the index occurred in the vicinities of 21, 23, 27 and 50 minutes. The subject commented that he felt sleepy from the start of the experiment, and the observation result describes that the head swung forward at 38 minutes, the head tilted forward and the subject looked like sleeping at 44 to 54 minutes. The sleep could not be identified by the brain wave measurement in (A) due to mix of noise as a result of swinging of the head during the sleep.

Thus, the determination of the sleepiness-related phenomenon emergence period by using the method of the present invention is reasonably valid.

FIG. 87

In (G), the fatigue reception signal markedly lowers in the vicinity of 35 to 45 minutes, and since a rising tendency of the functional adjustment signal is found in that time zone, it can be determined that the subject entered the sleepiness-related phenomenon emergence period in that time zone. Moreover in (H) to (J), too, a rise of the functional adjustment signal is found in that time zone.

On the other hand, in (B), the sleep prediction phenomenon emerged in the vicinity of 17 to 36 minutes, and in (C), a burst wave emerged in the vicinities of 20, 26, 27, and 34 minutes. Then, in (F), a rapid fall of the index occurred in the vicinities of 16 and 45 minutes. The observation result describes that at 37 minutes, the head was slightly bobbing back and forth and the head bobbing became larger at 41 minutes.

Thus, the determination of the sleepiness-related phenomenon emergence period by using the method of the present invention is reasonably valid.

Here, in (F), after the rapid fall of the index in the vicinity of 45 minutes, the index rises and shows a state of recovery, and thus, the rapid fall at 45 minutes can be considered to indicate a rapid change of the state (in this case, a transition state from sleep to awakening). From this fact, the marked fall of the fatigue reception signal in the vicinity of 45 minutes illustrated in (G) of the present invention can be considered to indicate the emergence period of such a state change of a human being including the sleepiness-related phenomenon emergence period.

FIG. 88

In (G), a rising tendency of the functional adjustment signal and stabilization of the fatigue reception signal are found at 35 minutes and after, and a marked fall of the fatigue reception signal is found in the vicinity of 42 to 50 minutes. And since a rising tendency of the functional adjustment signal is found in these time zones, it can be determined that the subject entered the sleepiness-related phenomenon emergence period in those time zones. In (H) and (J), too, a rise of the functional adjustment signal is found in those time zones.

On the other hand, in (B), a waveform of the sleep prediction phenomenon is found at 0 to 16 minutes and 25 to 37 minutes and after that, it can be determined that the subject resisted falling asleep and felt asleep at 57 minutes. In (C), a burst wave emerges in the vicinities of 5, 10, 20, 32, and 37 minutes. In (F), a rapid fall of the index occurred in the vicinity of 38 minutes. The observation result describes that the head deeply tilted forward at 43 to 50 minutes.

Thus, the determination of the sleepiness-related phenomenon emergence period by using the method of the present invention is reasonably valid.

FIG. 89

In (G), the fatigue reception signal markedly lowered in the vicinity of 33 to 35 minutes, 42 to 45 minutes, and 48 to 55 minutes, and since a rising tendency of the functional adjustment signal is found in those time zones, it can be determined that the subject entered the sleepiness-related phenomenon emergence period in those time zones. Moreover, in (I), too, a rise of the functional adjustment signal is found in those time zones.

On the other hand, in (B), a waveform of the sleep prediction phenomenon is found at 0 to 13 minutes and 19 to 26 minutes and it can be determined that at 26 minutes and after, the subject repeated falling asleep and awakening and then, fell asleep at about 55 minutes. In (C), a burst wave emerged in the vicinities of 27 minutes and 44 minutes. In (F), a rapid fall of the index occurred in the vicinities of 25, 28, 41, 45, 51, 53, and 57 minutes. According to the comments of the subject and the observer, the subject felt sleepy at 15 and 25 minutes, fell asleep at 36 minutes and woke up at 38 minutes and then, fell asleep at 45 minutes and woke up at 49 minutes and fell asleep again at 53 minutes and after.

Moreover, according to the method of the present invention, in (G) to (J), a rise of the functional adjustment signal is found in the time zone when the subject resisted falling asleep from 24 to 34 minutes. Thus, the identification of the sleep-related phenomenon by the present invention is reasonable.

FIG. 90

In (G), fluctuation was small and the subject was resisting falling asleep at 35 to 40 minutes and 50 to 58 minutes, and a marked fall of the fatigue reception signal is found in the vicinity of 21 to 29 minutes and in the vicinity of 42 to 47 minutes, and a rising tendency of the functional adjustment signal is found in those time zones. Thus, it can be determined that the subject entered the sleepiness-related phenomenon emergence period in those time zones. That is, though the sleep prediction phenomenon is indicated before 30 minutes, the subject repeated falling asleep and awakening at 30 minutes and after. In (H) to (J), too, a rise of the functional adjustment signal is found in those time zones.

On the other hand, in (C), a burst wave emerged in the vicinity of 15 minutes and in the vicinity of 22 minutes. In (F), a rapid fall of the index occurred in the vicinities of 16, 21, 24, 26, 39, 46, and 48 minutes. The subject commented that "felt like being forced to be awake" at 28 minutes. At 32 minutes and after, the brain waves indicate the sleep stages 1 to 2 in (A).

Thus, the determination of the sleepiness-related phenomenon emergence period by using the method of the present invention is reasonably valid.

FIG. 91

In (G), the fatigue reception signal markedly lowers in the vicinities of 15 to 25 minutes and 31 to 37 minutes, and since a rising tendency of the functional adjustment signal is found in those time zones, it can be determined that the subject entered the sleepiness-related phenomenon emergence period in those time zones. Moreover, in (H) to (J), too, a rise of the functional adjustment signal is also found in those time zones. Furthermore, in (G), a fall of the fatigue reception signal is found also at 45 to 53 minutes, and the sleepiness-related phenomenon occurs, but in (H) to (J) in that time zone, the signals are all at a low level. However, in the low level state, the functional adjustment signal rose at 53 minutes and after, and the subject is considered to have entered microsleep at 53 minutes and after.

On the other hand, in the brain waves in (A), the subject reaches the sleep stages 1 to 2 in the vicinities of 3, 7, 12, 17, 22, 23, and 25 minutes. In (B), from the start of the experiment to 45 minutes, the waveforms all considered to be sleep prediction signals continue, and it is determined that the subject fell asleep at about 55 minutes. In (C), a burst wave indicating a sleep prediction signal emerged at 30 and 47 minutes. The subject commented that he "felt slightly sleepy" at 20 minutes, and was unsure whether he slept or not throughout the experiment. Thus, the determination of the sleepiness-related phenomenon emergence period using the method of the present invention is reasonably valid.

FIG. 92

In (G), the fatigue reception signal markedly lowers in the vicinities of 15 to 22 minutes, 25 to 30 minutes, and 40 to 45 minutes, and since a rising tendency of the functional adjustment signal is found in those time zones, it can be determined that the subject entered the sleepiness-related phenomenon emergence period in those time zones. Moreover, in (I) and (J), a rise of the functional adjustment signal is found in the vicinity of 15 to 20 minutes, and in (H), a rise of the functional adjustment signal is found in the vicinity of 40 minutes.

On the other hand, in the brain waves in (A), the subject intermittently reaches the sleep stage 1 from 5 to 30 minutes and reaches the sleep stage 2 in the vicinity of 46 minutes. In (F), a rapid fall of the index occurs in the vicinities of 18, 22, 43, 49, 56, and 57 minutes. The subject commented that he felt sleepy from the start to 30 minutes, and the observation result describes that the subject looked like sleeping at about 37 minutes, moved the head and woke up at 48 minutes.

Thus, the determination of the sleepiness-related phenomenon emergence period by using the method of the present invention is reasonably valid.

From the above-described test examples, the determination of the sleepiness-related phenomenon emergence period using the method of the present invention does not match the states of the subjects and comments in some cases. Moreover, the method of determining the sleep prediction phenomenon on the basis of whether the slope time-series waveform of the power value and the slope time-series waveform of the maximum Lyapunov exponent emerge in the opposite phase or not previously proposed by the applicant of this application, the method of determining the sleep prediction phenomenon on the basis of whether a burst wave of the sympathetic nerve emerges or not, and the like capture the sleep prediction phenomenon occurring at about 5 to 10 minutes prior to the sleep-onset point. On the other hand, the sleepiness-related phenomenon emergence period in this application captures temporary sleepiness including the sleep prediction phenomenon as above and a shallow sleep state, too. Therefore, there might be a slight difference between them, but the method of the present invention can capture the biological body information relating to sleepiness substantially reliably. In order to make more accurate determination, the method of determining the sleep prediction phenomenon on the basis of whether the slope time-series waveform of the power value and the slope time-series waveform of the maximum Lyapunov exponent emerge in opposite phase states or not, the method of determining the sleep prediction phenomenon on the basis of whether a burst wave of the sympathetic nerve emerges or not proposed by the applicant of this application and the like may be used at the same time so as to determine the sleepiness-related phenomenon emergence period on the basis of to what degree they match each other.

INDUSTRIAL APPLICABILITY

The present invention can be applied by arranging the biological signal measuring means in a vehicle seat such as of an automobile to not only estimate a state of sleepiness of a passenger but also to estimate a state by arranging the biological signal measuring means in a chair arranged in a household, a desk chair and the like. Moreover, the present invention can be applied to estimate a state of a human being by arranging the biological signal measuring means in beddings such as a bed so as to capture oscillation of an aorta on the back part and to make analysis by the above-described biological signal measuring device. As a result, a health state of a person lying on a bed (particularly, sick people and those requiring care) can be easily grasped on a screen displayed on a monitor of display means.

REFERENCE SIGNS LIST

1 biological signal measuring means
10 three-dimensional knitted material
15 three-dimensional knitted material supporting member
15a through hole for arrangement
16 film
21, 22 plate-shaped foam body
30 vibration sensor
100 seat
110 seatback frame
120 skin
60 biological body state estimation device
610 first frequency calculating means (first frequency calculating step)
620 second frequency calculating means (second frequency calculating step)
630 first frequency slope time-series analysis calculating means (first frequency slope time-series analysis calculating step)
640 second frequency slope time-series analysis calculating means (second frequency slope time-series analysis calculating step)
650 first frequency fluctuation time-series analysis calculating means (first frequency fluctuation time-series analysis calculating step)
660 second frequency fluctuation time-series analysis calculating means (second frequency fluctuation time-series analysis calculating step)
670 power spectrum calculating means (power spectrum calculating step)
680 determining means (determining step)

The invention claimed is:

1. A biological body state estimation device for estimating a state of a human being by using a biological signal sampled from the upper body of a human by biological signal measuring means, the device comprising:

first frequency calculating means for acquiring a zero-crossing point at which a time-series waveform of a biological signal obtained by the biological signal measuring means is changed from positive to negative and for acquiring the time-series waveform of the frequency of the biological signal by using this zero-crossing point;

first frequency slope time-series analysis calculating means for performing movement calculation for acquiring a slope of the frequency at each predetermined time window set with a predetermined overlap time in the time-series waveform of the frequency of the biological signal obtained by the first frequency calculating means and for outputting a time-series change of the slope of the frequency obtained at each time window as a frequency slope time-series waveform;

power spectrum calculating means for applying frequency analysis to the frequency slope time-series waveform obtained by the first frequency slope time-series analysis calculating means and acquiring a power spectrum of each frequency corresponding to a functional adjustment signal, a fatigue reception signal, and an activity adjustment signal determined in advance; and determining means for determining a state of a human being by acquiring a time-series change of the power spectrum of each frequency corresponding to the functional adjustment signal, the fatigue reception signal, and the activity adjustment signal acquired by the power spectrum calculating means and by acquiring a degree of relative predominance of each signal as a distribution rate.

2. The biological body state estimation device according to claim 1, further comprising:

first frequency fluctuation time-series analysis calculating means for performing the movement calculation for acquiring a mean value of the frequency at each predetermined time window set with the predetermined overlap time in the time-series waveform of the frequency of the biological signal obtained by the first frequency calculating means and acquiring a time-series waveform of the mean value of the frequency obtained at each time window as a frequency fluctuation time-series waveform, wherein the power spectrum calculating means further has means for applying frequency analysis to the frequency fluctuation time-series waveform obtained by the first frequency fluctuation time-series analysis calculating means and acquiring a power spectrum of each frequency corresponding to the functional adjustment signal, the fatigue reception signal, and the activity adjustment signal determined in advance.

3. The biological body state estimation device according to claim 1, further comprising:

second frequency calculating means for acquiring a maximum value by applying smoothing differentiation to an original waveform of the biological signal obtained by the biological signal measuring means and acquiring the time-series waveform of the frequency of the biological signal by using this maximum value; and second frequency slope time-series analysis calculating means for performing the movement calculation for acquiring a slope of the frequency at the predetermined time window set with the predetermined overlap time in the time-series waveform of the frequency of the biological signal obtained by the second frequency calculating means and outputting a time-series change of the slope of the frequency obtained at each time window as a frequency slope time-series waveform, wherein the power spectrum calculating means further has means for applying frequency analysis to the frequency slope time-series waveform obtained by the second frequency slope time-series analysis calculating means and acquiring a power spectrum of each frequency corresponding to the functional adjustment signal, the fatigue reception signal, and the activity adjustment signal determined in advance.

4. The biological body state estimation device according to claim 3, further comprising:

second frequency fluctuation time-series analysis calculating means for performing the movement calculation to acquire a mean value of the frequency at each predetermined time window set with the predetermined overlap time in the time-series waveform of the frequency of the biological signal obtained by the second frequency calculating means and acquiring a time-series waveform of a mean value of the frequency obtained at each time window as a frequency fluctuation time-series waveform, wherein the power spectrum calculating means further has means for applying frequency analysis to the frequency fluctuation time-series waveform obtained by the second frequency fluctuation time-series analysis calculating means and acquiring a power spectrum of each frequency corresponding to the functional adjustment signal, the fatigue reception signal, and the activity adjustment signal determined in advance.

5. The biological body state estimation device according to claim 1, wherein the determining means determines the state of a human being by acquiring the time-series change in the power spectrum of each frequency corresponding to the functional adjustment signal, the fatigue reception signal, and the activity adjustment signal acquired from the frequency slope time-series waveform obtained by the first frequency slope time-series analysis calculating means and by acquiring a degree of relative predominance of each signal as a distribution rate; and determines the state of a human being by adding a time-series change of the distribution rate of the power spectrum of each frequency corresponding to the functional adjustment signal, the fatigue reception signal, and the activity adjustment signal acquired from at least one of the frequency fluctuation time-series waveform obtained by the first frequency fluctuation time-series analysis calculating means, the frequency slope time-series waveform obtained by the second frequency slope time-series analysis calculating means, and the frequency fluctuation time-series waveform obtained by the second frequency fluctuation time-series analysis calculating means.

6. The biological body state estimation device according to claim 1, wherein the determining means has means for determining that a time zone in which the power spectrum of the fatigue reception signal acquired from the frequency slope time-series waveform obtained by the first frequency slope time-series analysis calculating means indicates a time-series change having a lowering tendency is an emergence period of a state change of a human being.

7. The biological body state estimation device according to claim 6, wherein the determining means has means for determining a sleepiness-related phenomenon emergence period if the power spectrum of the functional adjustment signal acquired from the frequency slope time-series waveform obtained by the first frequency slope time-series analysis calculating means indicates a time-series change having a rising tendency in a time zone when the power spectrum of the fatigue reception signal acquired from the frequency slope time-series waveform obtained by the first frequency slope time-series analysis calculating means indicates a time-series change having a lowering tendency.

8. The biological body state estimation device according to claim 7, wherein
the determining means further has means for determining the sleepiness-related phenomenon emergence period if the functional adjustment signal acquired from at least one of the frequency fluctuation time-series waveform obtained by the first frequency fluctuation time-series analysis calculating means, the frequency slope time-series waveform obtained by the second frequency slope time-series analysis calculating means, and the frequency fluctuation time-series waveform obtained by the second frequency fluctuation time-series analysis calculating means indicates a time-series change with a rising tendency.

9. The biological body state estimation device according to claim 1, wherein
the functional adjustment signal used by the power spectrum calculating means has a frequency of 0.0027 Hz or less, the fatigue reception signal has a frequency within a range from 0.002 to 0.0052 Hz, and the activity adjustment signal has a frequency within a range from 0.004 to 0.007 Hz.

10. A non-transitory computer readable medium storing thereon a computer program incorporated in a biological body state estimation device that when executed implements a method for estimating a state of a human being by using a biological signal sampled from the upper body of a human being by the biological signal measuring means, the method comprising:
a first frequency calculating step of acquiring a zero-crossing point at which a time-series waveform of a biological signal obtained by the biological signal measuring means is changed from positive to negative and of acquiring the time-series waveform of the frequency of the biological signal by using this zero-crossing point;
first frequency slope time-series analysis calculating step of performing movement calculation for acquiring a slope of the frequency at each predetermined time window set with a predetermined overlap time in the time-series waveform of the frequency of the biological signal obtained by the first frequency calculating step and of outputting a time-series change of the slope of the frequency obtained at each time window as a frequency slope time-series waveform;
power spectrum calculating step of applying frequency analysis to the frequency slope time-series waveform obtained by the first frequency slope time-series analysis calculating step and acquiring a power spectrum of each frequency corresponding to a functional adjustment signal, a fatigue reception signal, and an activity adjustment signal determined in advance; and
determining step of determining a state of a human being by acquiring a time-series change of the power spectrum of each frequency corresponding to the functional adjustment signal, the fatigue reception signal, and the activity adjustment signal acquired by the power spectrum calculating step and by acquiring a degree of relative predominance of each signal as a distribution rate.

11. The non-transitory computer readable medium according to claim 10, further comprising:
a first frequency fluctuation time-series analysis calculating step of performing the movement calculation for acquiring a mean value of the frequency at each predetermined time window set with the predetermined overlap time in the time-series waveform of the frequency of the biological signal obtained by the first frequency calculating step and acquiring a time-series waveform of the mean value of the frequency obtained at each time window as a frequency fluctuation time-series waveform; and
the power spectrum calculating step further has a step of applying frequency analysis to the frequency fluctuation time-series waveform obtained by the first frequency fluctuation time-series analysis calculating step and of acquiring a power spectrum of each frequency corresponding to the functional adjustment signal, the fatigue reception signal, and the activity adjustment signal determined in advance.

12. The non-transitory computer readable medium according to claim 10, further comprising:
a second frequency calculating step of acquiring a maximum value by applying smoothing differentiation to an original waveform of the biological signal obtained by the biological signal measuring means and of acquiring the time-series waveform of the frequency of the biological signal by using this maximum value; and
a second frequency slope time-series analysis calculating step of performing the movement calculation for acquiring a slope of the frequency at each predetermined time window set with the predetermined overlap time in the time-series waveform of the frequency of the biological signal obtained by the second frequency calculating step and of outputting a time-series change of the slope of the frequency obtained at each time window as a frequency slope time-series waveform, wherein
the power spectrum calculating step further has a step of applying frequency analysis to the frequency slope time-series waveform obtained by the second frequency slope time-series analysis calculating step and of acquiring a power spectrum of each frequency corresponding to the functional adjustment signal, the fatigue reception signal, and the activity adjustment signal determined in advance.

13. The non-transitory computer readable medium according to claim 12, further comprising:
a second frequency fluctuation time-series analysis calculating step of performing the movement calculation to acquire a mean value of the frequency at each predetermined time window set with the predetermined overlap time in the time-series waveform of the frequency of the biological signal obtained by the second frequency calculating step and acquiring a time-series waveform of a mean value of the frequency obtained at each time window as a frequency fluctuation time-series waveform, wherein
the power spectrum calculating step further has a step of applying frequency analysis to the frequency fluctuation time-series waveform obtained by the second frequency fluctuation time-series analysis calculating step and acquiring a power spectrum of each frequency corresponding to the functional adjustment signal, the fatigue reception signal, and the activity adjustment signal determined in advance.

14. The non-transitory computer readable medium according to claim 10, wherein
the determining step determines the state of a human being by acquiring the time-series change in the power spectrum of each frequency corresponding to the functional adjustment signal, the fatigue reception signal, and the activity adjustment signal acquired from the frequency slope time-series waveform obtained by the first frequency slope time-series analysis calculating step and by acquiring a degree of relative predominance of each signal as a distribution rate; and determines the state of a human being by adding a time-series change of the distribution rate of the power spectrum of each frequency corresponding to the functional adjustment signal, the fatigue reception signal, and the activity adjustment signal acquired from at least one of the frequency fluctuation time-series waveform obtained by the first frequency fluctuation time-series analysis calculating step, the frequency slope time-series waveform obtained by the second frequency slope time-series analysis calculating step, and the frequency fluctuation time-series waveform obtained by the second frequency fluctuation time-series analysis calculating step.

15. The non-transitory computer readable medium according to claim 10, wherein
the determining step has a step of determining that a time zone in which the power spectrum of the fatigue reception signal acquired from the frequency slope time-series waveform obtained by the first frequency slope time-series analysis calculating step indicates a time-series change having a lowering tendency is an emergence period of a state change of a human being.

16. The non-transitory computer readable medium according to claim 15, wherein
the determining step has a step of determining a sleepiness-related phenomenon emergence period if the power spectrum of the functional adjustment signal acquired from the frequency slope time-series waveform obtained by the first frequency slope time-series analysis calculating step indicates a time-series change having a rising tendency in a time zone when the power spectrum of the fatigue reception signal acquired from the frequency slope time-series waveform obtained by the first frequency slope time-series analysis calculating step indicates a time-series change having a lowering tendency.

17. The non-transitory computer readable medium according to claim 16, wherein
the determining step further has a step of determining the sleepiness-related phenomenon emergence period if the functional adjustment signal acquired from at least one of the frequency fluctuation time-series waveform obtained by the first frequency fluctuation time-series analysis calculating step, the frequency slope time-series waveform obtained by the second frequency slope time-series analysis calculating step, and the frequency fluctuation time-series waveform obtained by the second frequency fluctuation time-series analysis calculating step indicates a time-series change with a rising tendency.

18. The non-transitory computer readable medium according to claim 10, wherein
the functional adjustment signal used by the power spectrum calculating step has a frequency of 0.0027 Hz or less, the fatigue reception signal has a frequency within a range from 0.002 to 0.0052 Hz, and the activity adjustment signal has a frequency within a range from 0.004 to 0.007 Hz.

19. A biological body state estimation device for estimating a state of a human being by using a biological signal sampled from the upper body of a human comprising:
circuitry configured to
acquire a zero-crossing point at which a time-series waveform of an obtained biological signal is changed from positive to negative,
acquire the time-series waveform of the frequency of the biological signal by using this zero-crossing point;
perform movement calculation for acquiring a slope of the frequency at each predetermined time window set with a predetermined overlap time in the time-series waveform of the frequency of the biological signal;
output a time-series change of the slope of the frequency obtained at each time window as a frequency slope time-series waveform;
apply frequency analysis to the frequency slope time-series waveform
acquire a power spectrum of each frequency corresponding to a functional adjustment signal, a fatigue reception signal, and an activity adjustment signal determined in advance; and
determine a state of a human being by acquiring a time-series change of the power spectrum of each frequency corresponding to the functional adjustment signal, the fatigue reception signal, and the activity adjustment signal and by acquiring a degree of relative predominance of each signal as a distribution rate.

* * * * *